US012600702B2

(12) United States Patent
Bullock et al.

(10) Patent No.: US 12,600,702 B2
(45) Date of Patent: Apr. 14, 2026

(54) CRYSTALLINE FORMS OF 4-(7-HYDROXY-2-ISOPROPYL-4-OXO-4H-QUINAZOLIN-3-YL)-BENZONITRILE AND FORMULATIONS THEREOF

(71) Applicant: Bausch + Lomb Ireland Limited, Dublin (IE)

(72) Inventors: Joseph Paul Bullock, Fort Worth, TX (US); Chinmay Maheshwari, Mason, OH (US); Quintus Medley, Wellesley, MA (US); Muneto Mogi, Waltham, MA (US); Michela Montecchi-Palmer, Fort Worth, TX (US); Gregory Morandi, Basel (CH); Michael Mutz, Lörrach (DE); Kalliopi Stasi, Waltham, MA (US); Christopher Stephen Towler, Quincy, MA (US)

(73) Assignee: Bausch + Lomb Ireland Limited, Dublin (IE)

( * ) Notice: Subject to any disclaimer, the term of this patent is extended or adjusted under 35 U.S.C. 154(b) by 915 days.

(21) Appl. No.: 17/430,819

(22) PCT Filed: Feb. 13, 2020

(86) PCT No.: PCT/IB2020/051212
§ 371 (c)(1),
(2) Date: Aug. 13, 2021

(87) PCT Pub. No.: WO2020/165840
PCT Pub. Date: Aug. 20, 2020

(65) Prior Publication Data

US 2022/0162170 A1 May 26, 2022

Related U.S. Application Data

(60) Provisional application No. 62/806,697, filed on Feb. 15, 2019.

(51) Int. Cl.
*C07D 239/91* (2006.01)
*A61P 27/02* (2006.01)

(52) U.S. Cl.
CPC ............ *C07D 239/91* (2013.01); *A61P 27/02* (2018.01); *C07B 2200/13* (2013.01)

(58) Field of Classification Search
CPC .... C07D 239/91; A61P 27/02; C07B 2200/13
See application file for complete search history.

(56) References Cited

U.S. PATENT DOCUMENTS 8,349,852 B2 * 1/2013 Chen ........................ A61P 25/04
514/266.3
2023/0286924 A1 * 9/2023 Mutz ........................ A61P 27/02

FOREIGN PATENT DOCUMENTS

WO WO-2010084050 A2 * 7/2010 ........... A61K 31/517

OTHER PUBLICATIONS

Papadakis, Emmanouil, Anjan K. Tula, and Rafiqul Gani. "Solvent selection methodology for pharmaceutical processes: Solvent swap." Chemical Engineering Research and Design 115 (2016): 443-461 (Year: 2016).*

Gupta, D., Bhatia, D., Dave, V., Sutariya, V. and Varghese Gupta, S., 2018. Salts of therapeutic agents: chemical, physicochemical, and biological considerations. Molecules, 23(7), p. 1719 (Year: 2018).*

Florence, "Polymorph screening in pharmaceutical development," European Pharmaceutical Review, available at <https://www.europeanpharmaceuticalreview.com/article/3659/polymorph-screening-in-pharmaceutical-development/> retrieved Mar. 7, 2018, published Aug. 19, 2010 (14 pages).

International Search Report and Written Opinion for International Publication No. PCT/IB2020/051212, mailed Jul. 6, 2020 (16 pages).

* cited by examiner

*Primary Examiner* — James H Alstrum-Acevedo
*Assistant Examiner* — Carolyn L. Ladd
(74) *Attorney, Agent, or Firm* — Finnegan, Henderson, Farabow, Garrett & Dunner, LLP

(57) ABSTRACT

The present disclosure provides polymorphs and formulations of 4-(7-hydroxy-2-isopropyl-4-oxo-4H-quinazolin-3-yl)-benzonitrile (compound I). The present disclosure further provides methods for treating ocular surface pain by administering 4-(7-hydroxy-2-isopropyl-4-oxo-4H-quinazolin-3-yl)-benzonitrile (compound I). The present invention also provides methods for treating dry eye disease and ocular hyperemia by administering 4-(7-hydroxy-2-isopropyl-4-oxo-4H-quinazolin-3-yl)-benzonitrile.

16 Claims, 15 Drawing Sheets

CRYSTALLINE FORMS OF 4-(7-HYDROXY-2-ISOPROPYL-4-OXO-4H-QUINAZOLIN-3-YL)-BENZONITRILE AND FORMULATIONS THEREOF

REFERENCE TO RELATED APPLICATIONS

The application is a national phase of PCT Application No. PCT/IB2020/051212, which claims priority to U.S. Provisional Application No. 62/806,697, which is incorporated herein in its entirety.

FIELD OF THE INVENTION

The present disclosure relates to crystalline forms of 4-(7-Hydroxy-2-isopropyl-4-oxo-4H-quinazolin-3-yl)-benzonitrile (Formula I) processes and methods for their manufacture. The invention also relates to formulations of compound I and methods for treating ocular surface disorders using same.

BACKGROUND OF THE INVENTION

Patients suffering from ocular surface pain, particularly chronic ocular surface pain have a significant decline in quality of life, and many develop depression, moderate-to-severe angina, dialysis, disabling hip fracture and in some cases become suicidal. In many patients, the ocular surface pain remains unresolved despite treatment of the underlying pathology (e.g., recent trauma or surgery, infection, or inflammation) and other known treatments cannot be used for long term therapy.

The Transient Receptor Potential Vanilloid 1 (TRPV1) receptor is implicated in pain signaling and antagonism of this receptor may be helpful in symptoms of pain. It would be desirable to administer topically to the surface of the eye a formulation of a TRPV1 antagonist to alleviate pain, particularly chronic pain.

Formulating hydrophobic ophthalmic drugs can be particularly troublesome, because they are particularly prone to agglomeration within aqueous topical ophthalmic compositions. Agglomeration may cause stability and potentially other quality issues for the compositions, and may arise from other interactions of drugs and excipients. Accordingly, there is a need for identification of different polymorphic forms that may be formulated in ophthalmic formulations for delivery to the ocular surface.

SUMMARY OF THE INVENTION

In some embodiments, the invention relates to a crystal form A of 4-(7-Hydroxy-2-isopropyl-4-oxo-4H-quinazolin-3-yl)-benzonitrile (compound I) having structure

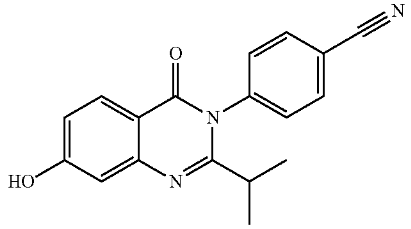 [SMILES: CC(C)c1nc2cc(O)ccc2c(=O)n1-c1ccc(C#N)cc1]

characterized by an X ray diffraction pattern having three or more peaks at 2θ values selected from 7.2, 12.7, and 21.4±0.2 °2θ. In some embodiments, the crystal form A of compound I is characterized by an X ray diffraction pattern having three or more peaks at 2θ values selected from 7.2, 12.7, 13.9, 18.1, 21.4, 25.1, and 26.8±0.2 °2θ. In some embodiments, the present disclosure relates to a method of preparing a crystal form A of compound I, comprising cooling a hot solution of the free base of compound I in methanol and cooling to about 0° C., to crystallize compound I as crystal form A.

In some embodiments, the invention relates to a crystal form C of 4-(7-Hydroxy-2-isopropyl-4-oxo-4H-quinazolin-3-yl)-benzonitrile (compound I) having structure

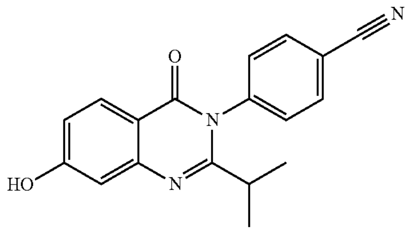 [SMILES: CC(C)c1nc2cc(O)ccc2c(=O)n1-c1ccc(C#N)cc1]

characterized by an X ray diffraction pattern having three or more peaks at 2θ values selected from 7.4, 14.9, 19.1±0.2 °2θ. In some embodiments, the crystal form C of compound I is characterized by an X ray diffraction pattern having three or more peaks at 2θ values selected from 7.4, 14.1, 14.9, 16.4, 19.1, 26.1, 31.2±0.2 °2θ. In some embodiments, the invention relates to a method of preparing a crystal form C of compound I, comprising heating compound I in crystal form A to a temperature of at least about 250° C., or at least about 270° C., or about 280° C.

In some embodiments, the invention relates to a crystal form E of 4-(7-Hydroxy-2-isopropyl-4-oxo-4H-quinazolin-3-yl)-benzonitrile (compound I) having structure

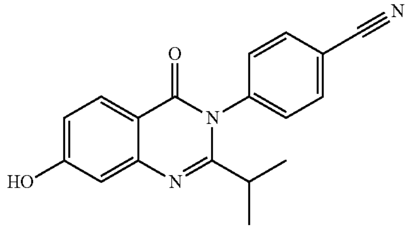 [SMILES: CC(C)c1nc2cc(O)ccc2c(=O)n1-c1ccc(C#N)cc1]

characterized by an X ray diffraction pattern having three or more peaks at 2θ values selected from 12.7, 16.7, 22.6±0.2 °2θ. In some embodiments, the crystal form E of compound I is characterized by an X ray diffraction pattern having three or more peaks at 2θ values selected from 12.7, 15.1, 16.7, 22.6, 27.1, 27.7, 28.5±0.2 °2θ. In some embodiments, the invention relates to a method of preparing a crystal form E of compound I, comprising heating a hydrate form of compound I to temperatures greater than about 250° C. or about 260° C. to provide compound I as crystal form E.

In some embodiments, the invention relates to a crystalline hydrate of 4-(7-Hydroxy-2-isopropyl-4-oxo-4H-quinazolin-3-yl)-benzonitrile (compound I) having structure compound I

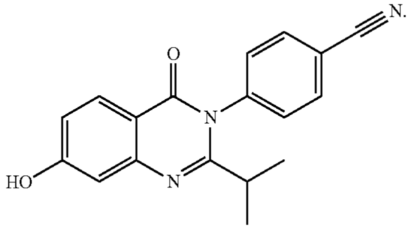

In some embodiments, the crystalline hydrate of compound I is characterized by an X ray diffraction pattern having three or more peaks at 2θ values selected from 6.6, 14.4, 18.3±0.2 °2θ. In some embodiments, the crystalline hydrate of compound I is characterized by an X ray diffraction pattern having three or more peaks at 2θ values selected from 6.6, 11.9, 14.4, 18.3, 23.9, 26.5, 29.2±0.2 °2θ. In some embodiments, the invention relates to a method of preparing the crystalline hydrate of compound I, comprising equilibrating a slurry of compound I in a mixture of water and a water miscible solvent, to crystallize compound I as the crystalline hydrate. In some embodiments, the water miscible solvent is acetone. IN some embodiments, the equilibration is carried out for about 12 hours, about 18 hours, or about 24 hours, or about 48 hours.

In some embodiments, the invention relates to a crystalline methanol solvate of 4-(7-Hydroxy-2-isopropyl-4-oxo-4H-quinazolin-3-yl)-benzonitrile (compound I) having structure compound I

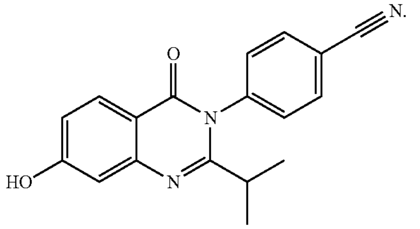

In some embodiments, the crystalline methanol solvate of compound I is characterized by an X ray diffraction pattern having three or more peaks at 2θ values selected from 6.1, 14.5, 22.7±0.2 °2θ. In some embodiments, the crystalline methanol solvate of compound I is characterized by an X ray diffraction pattern having three or more peaks at 2θ values selected from 6.1, 12.2, 14.5, 18.0, 22.7, 24.6±0.2 °2θ. In some embodiments, the invention relates to a method of preparing a crystalline methanol solvate of compound I, comprising equilibrating a slurry of compound I in methanol, to obtain compound I as polymorphic form G to provide compound I as the crystalline methanol solvate. In some embodiments, the equilibration is carried out for at least about 24 hours at room temperature.

In some embodiments, the invention relates to a crystalline acetonitrile solvate (form J) of 4-(7-Hydroxy-2-isopropyl-4-oxo-4H-quinazolin-3-yl)-benzonitrile (compound I) having structure compound I

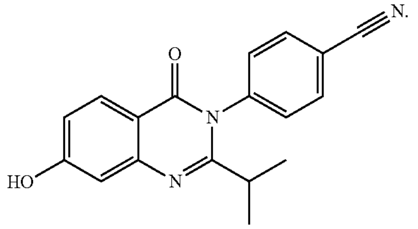

In some embodiments, the crystalline acetonitrile solvate of compound I is characterized by an X ray diffraction pattern having three or more peaks at 2θ values selected from 8.2, 17.0, 23.8±0.2 °2θ. In some embodiments, the crystalline acetonitrile solvate of compound I is characterized by an X ray diffraction pattern having three or more peaks at 2θ values selected from 8.2, 11.8, 17.0, 22.8, 23.8, 27.6±0.2 °2θ. In some embodiments, the invention relates to a method of preparing crystalline acetonitrile solvate of compound I, comprising equilibrating a slurry of compound I in acetonitrile to provide compound I as the crystalline acetonitrile solvate. In some embodiments, the equilibration is carried out for at least about 24 hours at room temperature.

In some embodiments, the invention relates to a crystal form K of 4-(7-Hydroxy-2-isopropyl-4-oxo-4H-quinazolin-3-yl)-benzonitrile (compound I) having structure

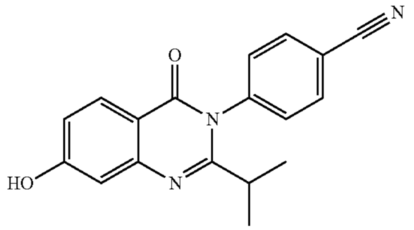 [SMILES: CC(C)c1nc2cc(O)ccc2c(=O)n1-c1ccc(C#N)cc1]

characterized by an X ray diffraction pattern having three or more peaks at 2θ values selected from 5.3, 12.3, 22.4±0.2 °2θ. In some embodiments, the crystal form K of compound I is characterized by an X ray diffraction pattern having three or more peaks at 20 values selected from 5.3, 6.5, 10.5, 12.3, 17.2, 19.3, 22.4±0.2 °2θ. In some embodiments, the invention relates to a method of preparing a crystal form K of compound I, comprising crystallizing by evaporation a solution of compound I in acetone to provide compound I as crystal form K.

In some embodiments, the invention relates to a crystal form L of 4-(7-Hydroxy-2-isopropyl-4-oxo-4H-quinazolin-3-yl)-benzonitrile (compound I) having structure

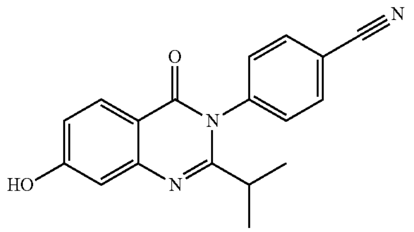 [SMILES: CC(C)c1nc2cc(O)ccc2c(=O)n1-c1ccc(C#N)cc1]

characterized by an X ray diffraction pattern having three or more peaks at 2θ values selected from 7.1, 8.7, 10.6±0.2 °2θ. In some embodiments, the crystal form L of compound I is characterized by an X ray diffraction pattern having three or more peaks at 2θ values selected from 3.5, 7.1, 8.7, 10.6, 12.2, 19.1, 22.4±0.2 °2θ. In some embodiments, the invention relates to a method of preparing a crystal form L of compound I, comprising adding a hydrocarbon solvent to a solution of compound I in acetone to provide compound I as crystal form L. In some embodiments, the hydrocarbon solvent is hexane.

In some embodiments, the present disclosure provides a pharmaceutical formulation, comprising an effective amount of a crystal form of compound I according to any crystal forms selected from the group consisting of: crystal form A, crystal form C, crystal form D, crystal form E, crystal form F, crystal form L, crystal form K, and combinations thereof, and a pharmaceutically acceptable excipient.

In some embodiments, the present disclosure provides a pharmaceutical formulation for ocular use (e.g., topical application to the ocular surface), comprising an effective amount of compound I in crystal form B, and an additional crystal form selected from the group consisting of: crystal form A, crystal form C, crystal form D, crystal form E, crystal form F, crystal form L, crystal form K, and combinations thereof, and a pharmaceutically acceptable excipient.

In some embodiments, the disclosure provides a pharmaceutical formulation, comprising the crystal form A in substantially pure form.

In some embodiments, the disclosure provides a pharmaceutical formulation, comprising the crystal form C in substantially pure form.

In some embodiments, the disclosure provides a pharmaceutical formulation, comprising the crystal form E in substantially pure form.

In some embodiments, the disclosure provides a pharmaceutical formulation, comprising the crystal form F in substantially pure form.

In some embodiments, the disclosure provides a pharmaceutical formulation, comprising the crystal form K in substantially pure form.

In some embodiments, the disclosure provides a pharmaceutical formulation, comprising the crystal form L in substantially pure form.

In some embodiments, the disclosure provides a pharmaceutical formulation, comprising a mixture of two or more crystal forms of compound I.

In some embodiments, the disclosure provides a pharmaceutical formulation, comprising a mixture of mixture of crystal forms B and E, crystal forms B and F, crystal forms B and C, crystal forms A and C, crystal forms A and F, in ratios of from about 1:99 to about 99:1.

In some embodiments, the pharmaceutical formulation, comprising any of the crystal forms disclosed herein is formulated for ocular use (e.g., topical application to the ocular surface).

In some embodiments, described herein is an aqueous formulation that includes:

4-(7-Hydroxy-2-isopropyl-4-oxo-4H-quinazolin-3-yl)-benzonitrile (compound I) or a salt, co-crystal, or polymorph thereof, and one or more excipients selected from the group consisting of a surfactant, a suspending agent, a tonicity agent, a buffer, a preservative, a salt, and a preservative.

In some embodiments, the 4-(7-Hydroxy-2-isopropyl-4-oxo-4H-quinazolin-3-yl)-benzonitrile (compound I) or a salt, co-crystal, or polymorph thereof is present in the formulation as a suspension. In alternative or additional embodiments, the 4-(7-Hydroxy-2-isopropyl-4-oxo-4H-quinazolin-3-yl)-benzonitrile (compound I) or a salt, co-crystal, or polymorph thereof is present in the formulation in an amount of about 0.5% w/v to about 3.5% w/v.

In some embodiments, described herein is an aqueous formulation that includes:

4-(7-Hydroxy-2-isopropyl-4-oxo-4H-quinazolin-3-yl)-benzonitrile (compound I) or a salt, co-crystal, or polymorph thereof, in an amount of about 0.5% w/v to about 3.5% w/v, present as a suspension in the formulation, a surfactant, a suspending agent, and one or more excipients selected from the group consisting of a tonicity agent, a buffer, a preservative, a salt, and a preservative.

In some embodiments, the invention described herein is a formulation that includes:

a suspension of 4-(7-Hydroxy-2-isopropyl-4-oxo-4H-quinazolin-3-yl)-benzonitrile (compound I) or a salt, co-crystal, or polymorph thereof, in an amount of about 0.5% w/v to about 3.5% w/v, a non-ionic surfactant;

a suspending agent;

a tonicity agent;

a buffer;

a salt; and optionally, a preservative.

In some embodiments, the present disclosure relates to a formulation, comprising:

a suspension of 4-(7-Hydroxy-2-isopropyl-4-oxo-4H-quinazolin-3-yl)-benzonitrile (compound I) or a salt, co-crystal, or polymorph thereof, in an amount of about 0.5% w/v to about 3.5% w/v, a surfactant selected from the group consisting of non-ionic, anionic, cationic surfactants, and combinations thereof;

a suspending agent;

a tonicity agent;

a buffer;

optionally, a salt;

optionally, a preservative; and water in quantity sufficient (qs) to 100%.

In some embodiments, the formulation includes a non-ionic surfactant. In some embodiments of the formulations described herein, the non-ionic surfactant is selected from the group consisting of a polysorbate surfactant, a block copolymer of ethylene oxide, propylene oxide surfactant, poloxamer, tyloxapol, and combinations thereof.

In some embodiments of the formulations described herein, the non-ionic surfactant is tyloxapol, which is present in an amount of at least about 0.001% w/v, at least about 0.01% w/v, at least about 0.02% w/v, least about 0.03% w/v, or at least about 0.04% w/v, and no more than about 1% w/v, no more than about 0.5% w/v, no more than about 0.3% w/v, or no more than about 0.2% w/v, no more than about 0.1% w/v, or no more than about 0.08% w/v. In some embodiments, the tyloxapol is present in an amount of about 0.03% w/v to 0.08% w/v, or about 0.05% w/v.

In some embodiments of the formulations described herein, the non-ionic surfactant is poloxamer in an amount of about 15 to about 20% w/v of the formulation.

In some embodiments of the formulations described herein, the suspending agent is selected from the group consisting of carbomer, hydroxypropyl methyl cellulose (hypromellose), polyethylene glycol, and combinations thereof. In some embodiments, the suspending agent is carbomer, present in the formulation in an amount of at least about 0.05% w/v, at least about 0.1% w/v, or at least about 0.2% w/v, and no greater than about 1.0% w/v, no greater than about 0.6% w/v, or no greater than about 0.5%. In some embodiments, the carbomer is present in the formulation in an amount of 0.1% w/v to about 0.3% w/v, or about 0.2% w/v.

In some embodiments of the formulations described herein, the suspending agent is hydroxypropyl methyl cellulose present in the formulation in an amount of at least about 0.05% w/v, at least about 0.1% w/v, or at least about 0.25% w/v, and less than about 1.8% w/v, less than about 1.0% w/v, less than about 0.8% w/v, or less than about 0.6% w/v. In some embodiments, the suspending agent is a polyethylene glycol (PEG) having molecular weight of from about 200 to about 20,000 Da. In some embodiments, the suspending agent is PEG400, at a concentration of from about 4% w/v to about 9% w/v, about 5% w/v to about 8% w/v, or about 7% w/v, or PEG6000 at a concentration of from about 1% w/v to about 4% w/v, about 1% w/v to about 3% w/v, or about 2% w/v.

In some embodiments of the formulations described herein, the suspending agent is substantially all carbomer homopolymer Type B.

In some embodiments of the formulations described herein, the tonicity agent is selected from the group consisting of polyols.

In some embodiments of the formulations described herein, the polyol is selected from the group selected from mannitol, glycerin, xylitol, sorbitol and propylene glycol, and combinations thereof. In some embodiments, the polyol is present in an amount from about 0.05% w/v to about 10% w/v, from about 0.1% to about 8% w/v, from about 0.1% to about 7% w/v, from about 0.1% to about 5% w/v. In particular embodiments, the polyol is mannitol or glycerin, present in the formulation in an amount of from 0.1% w/v to about 5% w/v, or about 0.2% w/v, about 0.3% w/v, about 0.4% w/v, about 0.5% w/v, about 1% w/v, about 2% w/v, about 2.5% w/v, about 3.0% w/v, about 3.5% w/v, about 4.0% w/v, about 4.5% w/v, or about 5% w/v.

In some embodiments of the formulations described herein, the buffer is selected from the group consisting of acetate, ascorbate, borate, hydrogen carbonate, carbonate, citrate, edetate (EDTA) gluconate, lactate, phosphate, propionate and TRIS (tromethamine). In particular embodiments, the buffer is phosphate or TRIS.

In some embodiments of the formulations described herein, the salt is sodium chloride or potassium chloride.

In some embodiments of the formulations described herein, the suspending agent is carbopol (carbomer homopolymer Type B) and amount of sodium chloride is adjusted to an amount to provide a viscosity of the formulation of about 20 cP to about 200 cP, when using spindle CP-42 at 60 rpm at about 25° C. In some embodiments, the sodium chloride is present in an amount from about 0.01% w/v to about 0.5% w/v, from about 0.02% w/v to about 0.4% w/v, from about 0.03% w/v to about 0.3% w/v, from about 0.04% w/v to about 0.2% w/v, from about 0.05% w/v to about 0.1% w/v, or about 0.05% w/v.

In some embodiments of the formulations described herein, the pH of the formulation is about 5.5 to about 8.0. In some embodiments, the pH of the formulation is from about 6.0 to about 8.0, about 6.0, or about 7.4.

In some embodiments the formulations described herein further include an additional agent selected from the group consisting of cyclodextrins in an amount of at least about 1.5 w/v %, at least about 3.0 w/v %, at least about 3.5 w/v % or at least about 4.5 w/v, but no greater than about 10.0 w/v %, no greater than about 8.0% w/v, no greater than about 6.5 w/v %, or no greater than about 5.5 w/v. In some embodiments, the cyclodextrin is hydroxypropyl β-cyclodextrin or sulfoalkylether β-cyclodextrin in an amount of about 5% w/v of the formulation.

In some embodiments, the present disclosure is related to a formulation, comprising:

the compound I or a salt, co-crystal, or polymorph thereof, is in an amount of about 0.5% w/v to about 2.5% w/v, the a non-ionic surfactant is tyloxapol, poloxamer, or combinations thereof, in an amount of from about 0.01 to 0.2% w/v;

the a suspending agent is hydroxypropyl methyl cellulose, polyethylene glycol or carbomer homopolymer Type B;

the a tonicity agent is at least one polyol in an amount of from about 0.05% w/v to about 10% w/v;

the buffer is edetate, phosphate, borate, or combinations thereof a salt; and water qs to 100%; and the pH is in the range of from about 5.5 to about 8.0.

In some embodiments, the present disclosure is related to a formulation, comprising: compound I or a salt, co-crystal, or polymorph thereof, is present in an amount of about 0.5% w/v, about 1.0% w/v, about 1.5% w/v, about 2.0% w/v, or about 2.5% w/v, a non-ionic surfactant, which is tyloxapol in an amount of about 0.04 w/v to about 0.06% w/v, poloxamer in an amount of about 0.005-0.12% w/v, or combinations thereof;

a suspending agent, which is hydroxypropyl methyl cellulose in an amount of from about 0.1% w/v to about 0.8 w/v %, polyethylene glycol in an amount of from about 2% w/v to about 8% w/v, carbomer homopolymer Type B in an amount from about 0.05% w/v to about 0.5% w/v, or combinations thereof;

a tonicity agent which is mannitol or glycerin in an amount of from about 0.1% w/v to about 5% w/v;

a buffer which is edetate, phosphate, borate, tromethamine, or combinations thereof;

sodium chloride in an amount of from 0.01% w/v to about 1% w/v; and water qs to 100%; and having a pH is in the range of from about 5.5 to about 8.0.

In some embodiments, the present disclosure is related to a formulation, comprising:

a suspension of 4-(7-Hydroxy-2-isopropyl-4-oxo-4H-quinazolin-3-yl)-benzonitrile (compound I) or a salt, co-crystal, or polymorph thereof, in an amount of about 0.5% w/v, about 1.0% w/v, about 1.5% w/v, about 2.0% w/v, or about 2.5% w/v, tyloxapol in an amount of about 0.04 w/v to about 0.06% w/v;

carbomer homopolymer Type B in an amount from about 0.05% w/v to about 0.4% w/v;

glycerin in an amount of from about 0.5% w/v to about 5% w/v;

a buffer selected from the group consisting of edetate, phosphate, borate, tomethamine, and combinations thereof;

sodium chloride in an amount of from 0.01% w/v to about 1% w/v; and water qs to 100%;

wherein the formulation has a pH in the range of from about 5.5 to about 8.0.

In some embodiments of the formulations described herein, compound I is in polymorphic form B.

In some embodiments, the present disclosure is related to a formulation, comprising:

a suspension of polymorphic form B of 4-(7-Hydroxy-2-isopropyl-4-oxo-4H-quinazolin-3-yl)-benzonitrile (compound I), in an amount of about 0.5% w/v, about 1.0% w/v, about 1.5% w/v, about 2.0% w/v, or about 2.5% w/v, tyloxapol in an amount of about 0.04 w/v to about 0.06% w/v;

carbomer homopolymer Type B in an amount from about 0.05% w/v to about 0.4% w/v;

glycerin in an amount of from about 0.5% w/v to about 5% w/v;

a buffer selected from edetate, phosphate, borate, tometh-amine, or combinations thereof;

sodium chloride in an amount of from 0.01% w/v to about 1% w/v; and water qs to 100%;

wherein the formulation has a pH in the range of from about 5.5 to about 8.0.

In some embodiments, the formulation comprises:

compound I in an amount of about 0.5% w/v, about 1.0% w/v, about 1.5% w/v, about 2.0% w/v, or about 2.5% w/v, about 0.05% w/v of tyloxapol;

about 0.2% w/v of carbomer homopolymer Type B;

about 2.0% of glycerin;

a tromethamine buffer; and hydrochloric acid to adjust pH to about 6.4 to about 8.4;

about 0.05% w/v of sodium chloride; and water qs to 100%;

wherein the formulation does not include a preservative.

In some embodiments of the formulations described herein, the polymorphic form B of compound I is characterized by an X-ray diffraction pattern having three or more peaks at 2θ values selected from 9.3, 10.6 and 14.4.+−0.0.2 °2θ.

In some embodiments, the formulations described herein have a viscosity of about 20 cP to about 200 cP.

In some embodiments, the formulations described herein have an osmolality of about 200 to about 450 milliosmoles per kilogram (mOsm/kg).

In some embodiments of the formulations described herein, the $D_{90}$ of compound I (diameter at which 90% of compound I is comprised of smaller particles) is below about 10 μm, below about 8 μm, below about 6 μm, below about 4 μm, below about 3 μm, or about 2 μm. In some embodiments, the $D_{50}$ of compound I in the formulation (diameter at which 50% of compound I is comprised of smaller particles) is below about 10 μm, below about 8 μm, below about 6 μm, below about 4 μm, below about 3 μm, below about 2 μm, or about 1 μm. In some embodiments, the $D_{10}$ of compound I in the formulation (diameter at which 10% of compound I is comprised of smaller particles) is below about 5 μm, below about 4 μm, below about 3 μm, below about 2 μm, below about 1 μm, or about 0.3 μm.

In some embodiments of the formulations described herein the formulation exhibits settling of less than about 10%, less than about 8%, less than about 7%, less than about 6%, less than about 5%, less than about 4%, less than about 3%, or less than about 2% after storage at room temperature for six months.

In some embodiments of the formulations described herein, the amount of compound I in the formulation is at least 90% of the initial amount after about 6 months, after about 8 months, about 10 months, about 12 months, about 15 months, or about 18 months of storage under refrigeration.

In some embodiments of the formulations described herein, the amount of compound I in the formulation at least about 91%, at least about 92%, at least about 93%, at least about 94%, at least about 95%, at least 96%, at least about 97% or at least about 98% of the initial amount after about 18 months of storage under refrigeration.

In some embodiments of the formulations described herein, the formulation comprises no more than about 10% of a degradation product after 6 months under refrigeration, wherein the degradation product has a relative retention time of 1.23, compared to compound I, when analyzed by HPMC using a gradient 0.1% trifluoroacetic acid (TFA) water/acetonitrile mobile phase.

In some embodiments of the formulations described herein, no more than about 10% of compound I in the formulation degrades upon storage for 12 weeks at 40° C.

In some embodiments of the formulations described herein, the compound I is in a crystal form selected from the group consisting of crystal form A, crystal form B, crystal form C, crystal form E, crystal form F, crystal form G, crystal form J, crystal form K, crystal form L, and combinations thereof.

In some embodiments of the formulations described herein, compound I is in a crystal form selected from the group consisting of crystal form A, crystal form B, crystal form C, crystal form E, crystal form F, crystal form K, crystal form L, and combinations thereof.

In some embodiments, the present disclosure is related to a method of making a formulation, comprising mixing an amount of 4-(7-Hydroxy-2-isopropyl-4-oxo-4H-quinazolin-3-yl)-benzonitrile (compound I) or a salt, co-crystal, or polymorph thereof, a non-ionic surfactant;

a suspending agent;

a tonicity agent;

a buffer;

a salt;

optionally, a preservative; and water qs to 100%, and adjusting the pH to a range of from about 5.5 to about 8.0.

In some embodiments, the method of making the formulations disclosed herein include the addition of compound I as a stock suspension. In some embodiments, the stock suspension is milled to achieve a desired particle size of compound I. In some embodiments, the $D_{90}$ of compound I in the formulation (diameter at which 90% of compound I is comprised of smaller particles) is below about 10 μm, below about 8 μm, below about 6 μm, below about 4 μm, below about 3 μm, or about 2 μm. In some embodiments, the $D_{50}$ of compound I in the formulation (diameter at which 50% of compound I is comprised of smaller particles) is below about 10 μm, below about 8 μm, below about 6 μm, below about 4 μm, below about 3 μm, below about 2 μm, or about 1 μm. In some embodiments, the $D_{10}$ of compound I in the formulation (diameter at which 10% of compound I is comprised of smaller particles) is below about 5 μm, below about 4 μm, below about 3 μm, below about 2 μm, below about 1 μm, or about 0.3 μm.

In some embodiments, the present disclosure is related to a method of treating ocular surface pain in a subject in need thereof, comprising ocularly administering an effective amount of 4-(7-Hydroxy-2-isopropyl-4-oxo-4H-quinazolin-3-yl)-benzonitrile (compound of formula I) having structure:

formula I

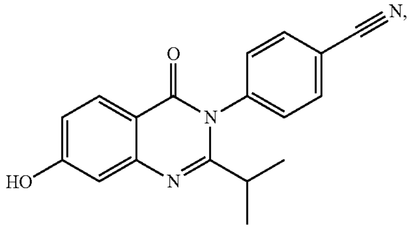

or a salt, solvate, polymorph, or co-crystal thereof to the subject.

In some embodiments, the ocular surface pain is acute or episodic ocular surface pain. In some embodiments, the ocular surface pain is chronic ocular surface pain lasting for at least 1 month, at least 2 months, or at least 3 months. In some embodiments, the compound of Formula I is administered to the cornea of the subject.

In some embodiments, the COSP is associated with dry eye disease. In some embodiments, the administration results in a decrease in the symptoms of dry eye disease. In some embodiments, the administration results in a decrease in the pain associated with dry eye disease. In some embodiments, the administration results in reduced incidence of at least about 10% in one or more of ocular dryness, ocular discomfort, ocular hyperemia, ocular burning or stinging, grittiness or foreign body sensation, or photophobia.

In some embodiments, the subject suffers from one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, patients recovering from neurotrophic keratitis, or ocular pain persisting for at least three months after photorefractive keratectomy (PRK) surgery or laser-assisted in situ keratomileusis (LASIK) surgery.

In some embodiments, the method comprises administering an additional therapeutic agent to the subject.

In some embodiments, the administration results in a reduction in a pain score on the visual acuity scale (VAS) of at least about 3, at least about 4, at least about 5, at least about 6, at least about 7, at least about 8, at least about 9 or at least about 10, compared to a placebo. In some embodiments, the reduction in VAS score arises from the difference in VAS scores prior to and after administration of compound I to the subject. In some embodiments, the reduction in VAS score occurs within about half hour, about one hour, within about 2 hours, within about 4 hours, or about 2-4 hours after administration of compound I to the subject.

In some embodiments, the administration of compound I results in a reduction in hyperemia in the subject of at least about 1, at least about 2, at least about 3, at least about 4, or at least about 5, on the McMonnies scale.

In some embodiments, the administration does not result in a change in one or more of best corrected visual acuity, intraocular pressure, slit-lamp biomicroscopy, dilated eye exam, blink rate, tear production, corneal staining, compared to a placebo.

In some embodiments, the compound of formula I is administered in the form of a formulation as described herein. In some embodiments, the formulation is administered for at least about one, about two, or about three months. In some embodiments, the formulation is administered one to four times daily.

In some embodiments, the disclosure provides a formulation as described herein, for use in the treatment of ocular surface pain. In some embodiments of the described uses, the ocular surface pain is episodic (e.g., acute) ocular surface pain or chronic ocular surface pain lasting for at least 1 month, at least 2 months, or at least 3 months.

In some embodiments, the disclosure provides a method of reducing ocular surface pain in a subject in need thereof, comprising ocularly administering 4-(7-Hydroxy-2-isopropyl-4-oxo-4H-quinazolin-3-yl)-benzonitrile (Formula I) having structure:

Formula I

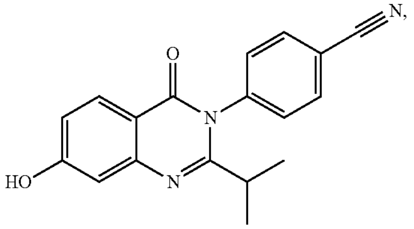

or a salt, solvate, polymorph, or co-crystal thereof to the subject.

In some embodiments, the ocular surface pain is episodic (e.g., acute) ocular surface pain the ocular surface pain is chronic ocular surface pain (COSP). In some embodiments, the COSP is associated with dry eye disease.

In some embodiments, the administration results in a decrease in the symptoms of dry eye disease. In some embodiments, the administration results in a decrease in the pain associated with dry eye disease. In some embodiments, the administration results in reduced incidence of at least about 10% in one or more of ocular dryness, ocular discomfort, ocular hyperemia, ocular burning or stinging, grittiness or foreign body sensation, or photophobia.

In some embodiments, the subject suffers from one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis. In some embodiments, the subject suffers from ocular pain persisting for at least three months after photorefractive keratectomy (PRK) surgery or laser-assisted in situ keratomileusis (LASIK) surgery.

In some embodiments, the method comprises administering an additional therapeutic agent to the subject.

In some embodiments, the administration results in a reduction in a pain score on the visual acuity scale (VAS) of at least about 3, at least about 4, at least about 5, at least about 6, at least about 7, at least about 8, at least about 9 or at least about 10, compared to a placebo. In some embodiments, the administration results in a reduction in a VAS pain score of at least about 6, at least about 7, at least about 8, at least about 9 or at least about 10, compared to a placebo. In some embodiments, the reduction in the pain score arises from the difference in pain scores prior to and after administration of compound I to the subject. In other embodiments, the reduction in pain score occurs after about 7 days of administration of compound I to the subject. In some embodiments, the reduction in pain score occurs after about 14 days of administration of compound I to the subject.

In some embodiments, the administration results in a reduction in hyperemia in the subject of least about 1, at least about 2, at least about 3, at least about 4, or at least about 5, on the McMonnies scale.

In some embodiments, the administration results in a reduction in a pain score on the visual acuity scale (VAS) of at least about 3 as compared to a VAS score prior to administration of the compound.

In some embodiments of the recited methods, the compound of formula I is administered in the form of a formulation as described herein.

In some embodiments, the present disclosure relates to a method of treating or reducing ocular surface pain in a subject in need thereof, comprising administering to the subject a formulation comprising a compound 4-(7-hydroxy-2-isopropyl-4-oxo-4H-quinazolin-3-yl)-benzonitrile (compound I) having structure:

compound I

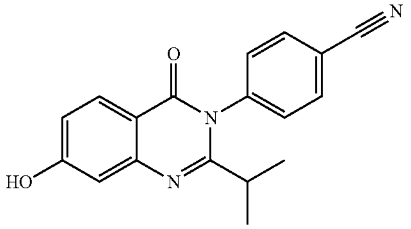 [SMILES: CC(C)c1nc2cc(O)ccc2c(=O)n1-c1ccc(C#N)cc1]

wherein the formulation results in a rabbit corneal Cmax compound I of about 1.5 to about 3 times conjunctival Cmax, wherein Cmax is the maximum concentration of compound I in the specified tissue after administration of a single dose. In some embodiments, the compound I is administered as a formulation as described herein.

In some embodiments, the present disclosure relates to a method of treating or reducing ocular surface pain in a subject in need thereof, comprising administering to the subject a formulation comprising a compound 4-(7-hydroxy-2-isopropyl-4-oxo-4H-quinazolin-3-yl)-benzonitrile (compound I) having structure:

compound I

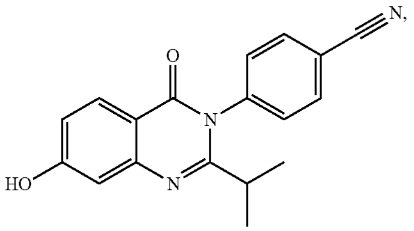

wherein the formulation results in a Cmax of compound I in a rabbit cornea of about 500 times the Cmax of compound I in plasma, wherein Cmax is the maximum concentration of compound I in the specified tissue after administration of a single dose. In some embodiments, the compound I is administered as a formulation as described herein.

Specific preferred embodiments of the invention will become evident from the following more detailed description of certain preferred embodiments and the claims.

BRIEF DESCRIPTION OF THE DRAWINGS

In FIG. 14A, the formulation with percent of compound I at about 75% of original at 12 weeks is the formulation of compound I as a solution. FIG. 1B shows the percent of compound I in the exploratory formulations after 12 weeks at 40° C.

DETAILED DESCRIPTION

Figure 1:
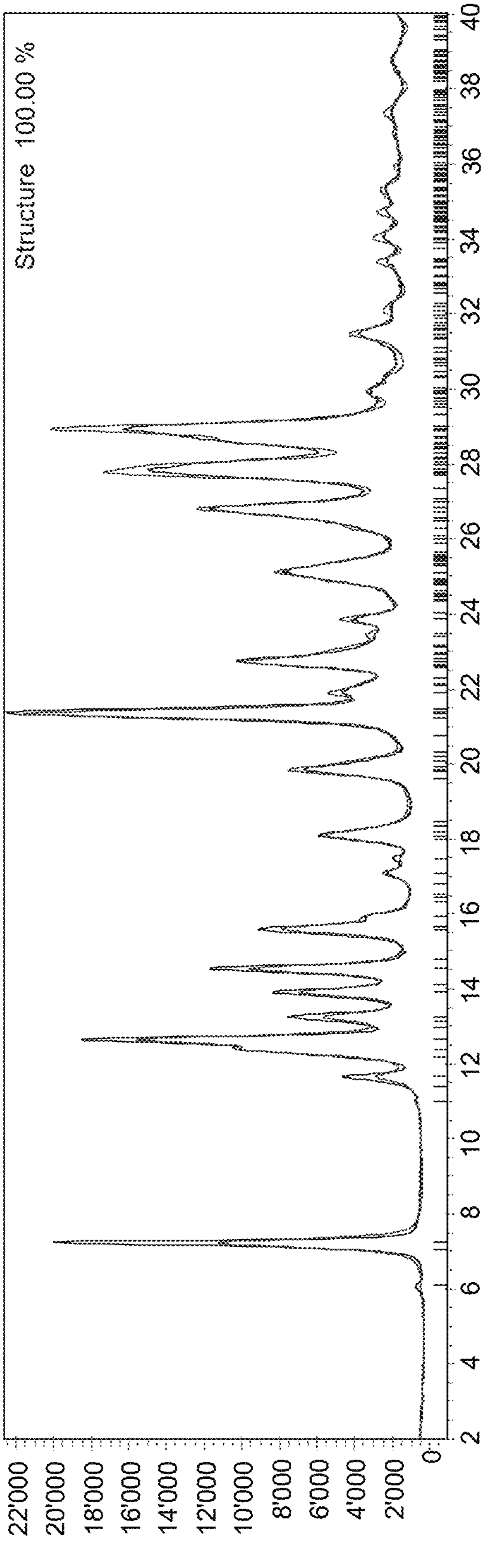
FIG. 1 provides a superposition of experimental and calculated XRPD patterns of crystal form A of compound I.

"TRPV1 receptor" refers to the Transient Receptor Potential Vanilloid 1 that has been characterized through molecular cloning and pharmacology. See e.g., Caterina M J, et al., *Nature* 1997; 389:816-824. TRPV1 receptor activity is measured as described in WO2005/120510, hereby incorporated by reference in its entirety.

The language "effective amount" of the compounds described herein, refers to that amount of a therapeutic compound necessary or sufficient to perform its intended function within a mammal. An effective amount of the therapeutic compound can vary according to factors such as the amount of the causative agent already present in the mammal, the age, sex, and weight of the mammal, and the ability of the therapeutic compounds of the present disclosure to treat the ocular surface disorder and/or symptoms thereof in the mammal.

The phrase "ophthalmically compatible" refers to formulations, polymers and other materials and/or dosage forms which are suitable for use in contact with the ocular tissues of human beings and animals without excessive toxicity, irritation, allergic response, or other problem or complication, commensurate with a reasonable benefit/risk ratio.

As used herein, the term "treat", "treating" or "treatment" in connection to a disease or disorder refers in some embodiments, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder or symptom thereof.

As used herein, the term "subject" or "patient" refers to human and non-human mammals, including but, not limited to, primates, rabbits, pigs, horses, dogs, cats, sheep, and cows. In particular embodiments, a subject or patient is a human. In some embodiments, the term "patient" or "subject" refers to a human being who is diseased with the condition (i.e., disease or disorder) described herein and who would benefit from the treatment. As used herein, a subject is "in need of" a treatment if such subject (patient) would benefit biologically, medically or in quality of life from such treatment. In particular embodiments, the subject is an adult human of at least about 18 years of age. In some embodiments, the subject is an adult human from about 18 years of age to about 75 years of age. In some embodiments, the subject is a child of up to about 18 years of age.

As used herein, "ocular surface" refers to the outer surface of the eye, which anatomically comprises the cornea (with epithelium, bowman layer, stroma, descement membrane, endothelium), conjunctiva, cul de sac, and the corneo-scleral junction, i.e. limbus.

As used herein, "pain" refers to constant or intermittent sensation of actual pain described as but not limited to stabbing, dull, sharp, or ache. Pain may also refer to similar related descriptors such as but not limited to burning, stinging, grittiness, foreign body sensation, dryness, sandy, tired, itchy, irritated, sensitivity to light.

As used herein, ocular administration includes administration to all parts of the eye including all parts of the ocular surface such as the cornea, conjunctiva, the cul de sac and the corneo-scleral junction, i.e., limbus.

As used herein, "ocular surface pain" refers to pain on the surface of the eye, e.g., cornea. Ocular pain may be nociceptic pain, which is generally caused by external physical or chemical damaging stimuli such as corneal surgery, inflammation, or other damage to the corneal surface. Ocular pain may also result from neuropathic pain, which may occur due to direct damage to the neurons of the body, resulting in messages of pain being sent to the central nervous system and brain regardless of the presence of noxious stimuli. As used herein "ocular surface pain" includes both nociceptic pain and neuropathic pain.

As used herein, the term "visual analog scale" (VAS) is a measure of pain intensity where a subject typically marks a place on a scale that aligns with their level of pain. The pain is marked in a range of "no pain" (score of 0) and "pain as bad as it could be" or "worst imaginable pain" (score of 100). See e.g., Hawker, et al., *Arthritis Care & Research* 63(11), pp. S240-S252 (November 2011). There are several other well-designed pain scales that may be used to help assess the extent of pain. The numerical rating scale (NRS) is often used, in which subjects use numbers to rate pain. The number scale may be from 1-10, or 1-100. The Wong-Baker FACES Pain Scale combines pictures and numbers for pain ratings. It can be used in children over the age of 3 and in adults. Six faces depict different expressions, ranging from happy to extremely upset. Each is assigned a numerical rating between 0 (smiling) and 10 (crying). The Verbal Pain Intensity Scale uses wordings on a scale to rate pain intensity: No Pain/Mild Pain/Moderate Pain/Severe Pain Very Severe Pain/Worst Possible Pain.

The Eye Sensation Scale is a specific pain scale was developed to measure ophthalmic pain severity. See Caudle L. E. et al., *Optom Vis Sci.* 2007 August; 84(8):752-62. In this scale, pain, discomfort or light sensitivity is typically measured by 5 category labels of "extreme," "severe," "moderate," "mild," or "none."

The Ocular Pain Assessment Survey (OPAS) is a quantitative, multidimensional questionnaire, specifically designed for assessment of corneal and ocular surface pain and Quality of Life (QoL) changes. The OPAS assesses pain intensity, frequency of eye and non-eye pain, QoL changes, aggravating factors, associated factors, and symptomatic relief quantitative, allowing for monitoring of treatment responses. See Qazi et al., *Ophthalmology* July 123(7):1458-1468 (2016).

As used herein, the term "Visual Tasking Questionnaire" refers to a questionnaire that asks the subject to subjectively rate how much difficulty they have conducting certain activities that require a fixed or prolonged stare that may exacerbate ocular pain. The questionnaire also asks about coping mechanisms associated with the difficulties they experience during visual tasking activities.

As used herein, ocular hyperemia refers to redness of the ocular surface. Ocular hyperemia may be a clinical marker for inflammation and/or ocular irritation. Ocular hyperemia is typically measured using the McMonnies scale, at values from 0 to 5, based on standard photographs.

As used herein, "placebo" refers to an ophthalmic formulation that includes all the components of the administered drug composition without the drug.

As used herein, the term "about" refers to a range of values+10% of a specified value.

As used herein "polymorph" refers to crystalline forms having the same chemical composition but different spatial arrangements of the molecules, atoms, and/or ions forming the crystal.

As used herein "solvate" refers to a crystalline form of a molecule, atom, and/or ions that further comprises molecules of a solvent or solvents incorporated into the crystalline lattice structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate. Solvates may occur as dimers or oligomers comprising more than one molecule of compound I within the crystalline lattice structure.

As used herein "amorphous" refers to a solid form of a molecule, atom, and/or ions that is not crystalline. An amorphous solid does not display a definitive X-ray diffraction pattern.

As used herein, "substantially pure," when used in reference to a form, means a compound having a purity greater than 90 weight %, including greater than 90, 91, 92, 93, 94, 95, 96, 97, 98, and 99 weight %, and also including equal to about 100 weight % of compound I, based on the weight of the compound. The remaining material comprises other form(s) of the compound, and/or reaction impurities and/or processing impurities arising from its preparation. For example, a crystalline form of compound I may be deemed substantially pure in that it has a purity greater than 90 weight %, as measured by means that are at this time known and generally accepted in the art, where the remaining less than 10 weight % of material comprises other form(s) of compound I and/or reaction impurities and/or processing impurities.

As used herein, "Compound of formula I," "Compound I," "Formula I," and "compound I" are used interchangeably and mean a compound that has the name 4-(7-hydroxy-2-isopropyl-4-oxo-4H-quinazolin-3-yl)-benzonitrile, the structure shown below, and can be synthesized using procedures known in the art and described in WO2005/120510 and U.S. Pat. No. 8,349,852 ("Quinazolinone derivatives useful as vanilloid antagonists") to Chen et al., both of which are hereby incorporated by reference in their entireties.

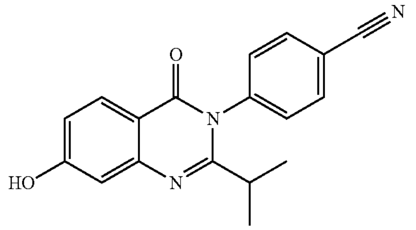 [SMILES: CC(C)c1nc2cc(O)ccc2c(=O)n1-c1ccc(C#N)cc1]

As used herein, "crystal form," "crystalline form," "modification," or "polymorph," or "polymorphic form" in upper or lower case are used interchangeably and refer to the crystalline or polymorphic form of compound I. Compound I may be used in amorphous or crystalline forms. Additionally or alternatively, various crystalline and polymorphic forms of Compound (I) may be used. As used herein, "polymorphic forms" or "polymorphs" of compound (I) is intended to encompass crystalline hydrates or other crystalline solvates of compound (I).

Any chemical formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the disclosure include, for example, isotopes of hydrogen, carbon, nitrogen, and oxygen, such as $^{3}H$, $^{11}C$, $^{13}C$, $^{14}C$, and $^{15}N$. Accordingly, it should be understood that methods of the present invention can or may involve compounds that incorporate one or more of any of the aforementioned isotopes, including for example, radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. Isotopically-labeled compounds can generally be prepared by conventional techniques known to those skilled in the art, e.g., using an appropriate isotopically-labeled reagents in place of the non-labeled reagent previously employed.

The present invention encompasses embodiments that include all pharmaceutically acceptable salts of the compounds useful according to the invention provided herein. As used herein, "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts of the parent compound formed, for example, from non-toxic inorganic or organic acids. The pharmaceutically acceptable salts can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* $17^{th}$ ed., Mack Publishing Company, Easton, Pa., 1985, p. 1418 and *Journal of Pharmaceutical Science,* 66, 2 (1977), each of which is incorporated herein by reference in its entirety. For example, preferred pharmaceutically acceptable salts include, but are not limited to, mineral or organic acid salts of basic residues such as amines. For example, the salt can be a hydrochloride salt. Other examples of suitable salts can be found in U.S. Pat. No. 8,349,852, the content of which is hereby incorporated by its entirety.

The phrase "pharmaceutically acceptable" as employed herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Unless indicated otherwise, all ingredient concentrations are presented in units of % weight/volume (% w/v). As is commonly understood, the % w/v value refers to the amount of the particular component or ingredient in the formulation. It is commonly understood that equivalent concentrations can be expressed in different units. For example, a concentration of 0.1% w/v can also be expressed as a 1 mg/ml solution.

Unless otherwise specified, the weight or dosage referred to herein for the compound of formula I is the weight or dosage of the compound itself, not that of a salt or prodrug thereof, which can be different to achieve the intended therapeutic effect. For example, the weight or dosage of a corresponding salt of a compound suitable for the methods, compositions, or combinations disclosed herein may be calculated based on the ratio of the molecular weights of the salt and compound itself.

Crystal form B of compound I is described in U.S. Pat. No. 8,349,852, incorporated by reference herein. Polymorph B is characterized by an X-ray diffraction pattern having three or more peaks at 2θ values selected from 9.3, 10.6 and 14.4.+−0.0.2 °2θ. In some embodiments, polymorph B is characterized by an X-ray diffraction pattern having three or more peaks at 2θ values selected from 9.3, 10.6, 14.4, 15.5, 17.9, 19.9, 23.4±0.2 °2θ.

Crystal Forms of Compound I

In one aspect, the present invention relates to crystal form A of compound I, characterized by an X-ray diffraction pattern having 3 or more peaks at 2θ values selected from 7.2, 12.7, and 21.4±0.2 °2θ. In some embodiments, crystal form A is characterized by an X-ray diffraction pattern having 3 or more peaks at 2θ values selected from 7.2, 12.7, 13.9, 18.1, 21.4, 25.1, and 26.8±0.2 °2θ. In some embodiments, crystal form A is characterized by an X-ray diffraction pattern having 3 or more, 4 or more, 5 or more, 6 or more, or 7 or more peaks at 2θ values selected from 7.2, 12.7, 13.3, 13.9, 14.5, 15.6, 18.1, 19.9, 21.4, 22.8, 25.1, 26.8, 27.8, 29.0±0.2 °2θ.

Crystal form A may be prepared by cooling a hot solution of the free base of compound I in methanol and cooling to about 0° C., to crystallize compound I as crystal form A.

In one embodiment, a crystal form A of compound I is provided in substantially pure form. This crystal form A of compound I in substantially pure form may be employed in pharmaceutical compositions, e.g., ophthalmic formulations as described herein. In some embodiments, the disclosure provides for pharmaceutical formulations including compound I in crystal form A. In some embodiments, the present disclosure provides ophthalmic suspensions of compound I, wherein at least 10%, at least about 20%, at least about 30%, at least about 40%, at least about 50%, at least about 60%, at least about 70%, at least about 80%, or at least 90% of compound I is present as crystal form A.

In one aspect, the present invention relates to crystal form C of compound I, characterized by an X-ray diffraction pattern having 3 or more peaks at 2θ values selected from 7.4, 14.9, 19.1±0.2 °2θ. In some embodiments, crystal form C is characterized by an X-ray diffraction pattern having 3 or more peaks at 2θ values selected from 7.4, 14.1, 14.9, 16.4, 19.1, 26.1, 31.2±0.2 °2θ. In some embodiments, crystal form C is characterized by an X-ray diffraction pattern having 3 or more, 4 or more, 5 or more, 6 or more, or 7 or more peaks at 2θ values selected from 7.4, 14.1, 14.9, 16.4, 19.1, 24.8, 26.1, 28.4, 31.2±0.2 °2θ.

Crystal form C may be prepared by heating crystal form A.

In one embodiment, a crystal form C of compound I is provided in substantially pure form. This crystal form C of compound I in substantially pure form may be employed in pharmaceutical compositions, e.g., ophthalmic formulations as described herein. In some embodiments, the disclosure provides for pharmaceutical formulations including compound I in crystal form C. In some embodiments, the present disclosure provides ophthalmic suspensions of compound I, wherein at least 10%, at least about 20%, at least about 30%, at least about 40%, at least about 50%, at least about 60%, at least about 70%, at least about 80%, or at least 90% of compound I is present as crystal form C.

In one aspect, the present invention relates to crystal form E of compound I, characterized by an X-ray diffraction pattern having 3 or more peaks at 2θ values selected from 12.7, 16.7, 22.6±0.2 °2θ. In some embodiments, crystal form E is characterized by an X-ray diffraction pattern having 3 or more peaks at 2θ values selected from 12.7, 15.1, 16.7, 22.6, 27.1, 27.7, 28.5±0.2 °2θ. In some embodiments, polymorph E of compound I has a melting onset temperature of about 281° C. In some embodiments, crystal form E is characterized by an X-ray diffraction pattern having 3 or more, 4 or more, 5 or more, 6 or more, or 7 or more peaks at 2θ values selected from 9.1, 11.9, 12.7, 13.8, 15.1, 16.7, 18.3, 21.3, 22.6, 24.4, 27.1, 27.7, 28.5, 37.8±0.2 °2θ.

Crystal form E may be prepared by heating a hydrate form of compound I to temperatures greater than about 250° C. or about 260° C. to provide compound I as crystal form E. In some embodiments, the heating is carried out in an oven.

In one embodiment, a crystal form E of compound I is provided in substantially pure form. This crystal form E of compound I in substantially pure form may be employed in pharmaceutical compositions, e.g., ophthalmic formulations as described herein. In some embodiments, the disclosure provides for pharmaceutical formulations including compound I in crystal form E. In some embodiments, the present disclosure provides ophthalmic suspensions of compound I, wherein at least 10%, at least about 20%, at least about 30%, at least about 40%, at least about 50%, at least about 60%, at least about 70%, at least about 80%, or at least 90% of compound I is present as crystal form E.

In one aspect, the present invention relates to a crystalline hydrate of compound I (polymorph F). In some embodiments, the crystalline hydrate of compound I is characterized by an X-ray diffraction pattern having 3 or more peaks at 2θ values selected from 6.6, 14.4, 18.3±0.2 °2θ. In some embodiments, the crystalline hydrate is characterized by an X-ray diffraction pattern having 3 or more peaks at 2θ values selected from 6.6, 11.9, 14.4, 18.3, 23.9, 26.5, 29.2±0.2 °2θ.

In some embodiments, the crystalline hydrate is characterized by an X-ray diffraction pattern having 3 or more, 4 or more, 5 or more, 6 or more, or 7 or more peaks at 2θ values selected from 6.7, 11.9, 12.8, 14.4, 15.6, 16.3, 18.3, 19.5, 22.7, 23.9, 24.7, 25.6, 26.5, 29.2±0.2 °2θ.

Crystal form F may be prepared by equilibration of a slurry of compound I in a mixture of water and a water miscible solvent, to crystallize compound I as crystal form F. In particular embodiments, the water miscible solvent is acetone. In some embodiments, the equilibration is carried out for about 12 hours, about 18 hours, or about 24 hours, or about 48 hours. In some embodiments, the equilibration is carried out at room temperature, i.e., about 25° C.

In one embodiment, a crystal form F of compound I is provided in substantially pure form. This crystal form F of compound I in substantially pure form may be employed in pharmaceutical compositions, e.g., ophthalmic formulations as described herein. In some embodiments, the disclosure provides for pharmaceutical formulations including compound I as the crystalline hydrate form (polymorph F). In some embodiments, the present disclosure provides ophthalmic suspensions of compound I, wherein at least 10%, at least about 20%, at least about 30%, at least about 40%, at least about 50%, at least about 60%, at least about 70%, at least about 80%, or at least 90% of compound I is present as the crystalline hydrate (polymorph F).

In one aspect, the present invention relates to a crystalline methanol solvate form (polymorph G) of compound I. In some embodiments, the crystalline methanol solvate of compound I is characterized by an X-ray diffraction pattern having 3 or more peaks at 2θ values selected from 6.1, 14.5, 22.7±0.2 °2θ. In some embodiments, the crystalline methanol solvate is characterized by an X-ray diffraction pattern having 3 or more peaks at 2θ values selected from 6.1, 12.2, 14.5, 18.0, 22.7, 24.6±0.2 °2θ.

Polymorphic form G may be prepared by equilibrating a slurry of compound I in methanol, to obtain compound I as crystal form G. In some embodiments, the equilibration is carried out for about 12 hours, about 18 hours, or about 24 hours, or about 48 hours. In some embodiments, the equilibration is carried out at room temperature, i.e., about 25° C.

In one embodiment, a crystal form G of compound I is provided in substantially pure form. This crystal form G of compound I in substantially pure form may be employed in pharmaceutical compositions, e.g., ophthalmic formulations as described herein. In some embodiments, the disclosure provides for pharmaceutical formulations including compound I as the crystalline methanol form (polymorph G). In some embodiments, the present disclosure provides ophthalmic suspensions of compound I, wherein at least 10%, at least about 20%, at least about 30%, at least about 40%, at least about 50%, at least about 60%, at least about 70%, at least about 80%, or at least 90% of compound I is present as the crystalline methanol solvate (polymorph G).

In one aspect, the present invention relates to a crystalline acetonitrile solvate (crystal form J). In some embodiments, the crystalline acetonitrile solvate of compound I is characterized by an X-ray diffraction pattern having 3 or more peaks at 2θ values selected from 8.2, 17.0, 23.8±0.2 °2θ. In some embodiments, the crystalline acetonitrile solvate is characterized by an X-ray diffraction pattern having 3 or more peaks at 2θ values selected from 8.2, 11.8, 17.0, 22.8, 23.8, 27.6±0.2 °2θ. In some embodiments, the crystalline acetonitrile solvate is characterized by an X-ray diffraction pattern having 3 or more, 4 or more, 5 or more, 6 or more, or 7 or more peaks at 2θ values selected from 8.2, 11.8, 17.0, 22.8, 23.8, 27.6, 31.4±0.2 °2θ.

The crystalline acetonitrile solvate may be prepared by equilibrating a slurry of compound I in acetonitrile. In some embodiments, the compound I n the slurry is in crystal form A. In some embodiments, the equilibration is carried out for about 12 hours, about 18 hours, or about 24 hours, or about 48 hours. In some embodiments, the equilibration is carried out at room temperature, i.e., about 25° C.

In one embodiment, the crystalline acetonitrile solvate of compound I is provided in substantially pure form. This crystalline acetonitrile solvate of compound I in substantially pure form may be employed in pharmaceutical compositions, e.g., ophthalmic formulations as described herein. In some embodiments, the disclosure provides for pharmaceutical formulations including compound I as the crystalline acetonitrile solvate (polymorph J). In some embodiments, the present disclosure provides ophthalmic suspensions of compound I, wherein at least 10%, at least about 20%, at least about 30%, at least about 40%, at least about 50%, at least about 60%, at least about 70%, at least about 80%, or at least 90% of compound I is present as the crystalline acetonitrile solvate (polymorph J).

In one aspect, the present invention relates to crystal form K of compound I, characterized by an X-ray diffraction pattern having 3 or more peaks at 2θ values selected from 5.3, 12.3, 22.4±0.2 °2θ. In some embodiments, crystal form K is characterized by an X-ray diffraction pattern having 3 or more, 4 or more, 5 or more, or 6 or more peaks at 2θ values selected from 5.3, 6.5, 10.5, 12.3, 17.2, 19.3, 22.4±0.2 °2θ.

Crystal form K may be prepared by evaporation crystallization of compound I in acetone, to crystallize compound I as crystal form K.

In one embodiment, a crystal form K of compound I is provided in substantially pure form. This crystal form K of compound I in substantially pure form may be employed in pharmaceutical compositions, e.g., ophthalmic formulations as described herein. In some embodiments, the disclosure provides for pharmaceutical formulations including compound I as the polymorph K. In some embodiments, the present disclosure provides ophthalmic suspensions of compound I, wherein at least 10%, at least about 20%, at least about 30%, at least about 40%, at least about 50%, at least about 60%, at least about 70%, at least about 80%, or at least 90% of compound I is present as the polymorph K.

In one aspect, the present invention relates to crystal form L of compound I, characterized by an X-ray diffraction pattern having 3 or more peaks at 2θ values selected from 7.1, 8.7, 10.6±0.2 °2θ. In some embodiments, crystal form L is characterized by an X-ray diffraction pattern having 3 or more peaks at 2θ values selected from 3.5, 7.1, 8.7, 10.6, 12.2, 19.1, 22.4±0.2 °2θ. In some embodiments, crystal form L is characterized by an X-ray diffraction pattern having 3 or more, 4 or more, 5 or more, 6 or more, or 7 or more peaks at 20 values selected from 3.5, 7.1, 8.7, 10.6, 11.1, 12.2, 19.1, 21.1, 22.4, 23.4±0.2 °2θ.

Crystal form L may be prepared by precipitation of a solution of compound I in acetone by the adding a hydrocarbon solvent, to crystallize compound I as crystal form L. In some embodiments, the hydrocarbon solvent is pentane, hexane, or heptane. In particular embodiments, the hydrocarbon solvent is hexane.

In one embodiment, a crystal form L of compound I is provided in substantially pure form. This crystal form L of compound I in substantially pure form may be employed in pharmaceutical compositions, e.g., ophthalmic formulations as described herein. In some embodiments, the disclosure provides for pharmaceutical formulations including compound I as the polymorph L. In some embodiments, the present disclosure provides ophthalmic suspensions of compound I, wherein at least 10%, at least about 20%, at least about 30%, at least about 40%, at least about 50%, at least about 60%, at least about 70%, at least about 80%, or at least 90% of compound I is present as the polymorph L.

In some embodiments, the present invention provides formulations of the compound of formula I. In some embodiments, the formulations are aqueous suspensions of a compound of formula I. In some embodiments, the suspension includes the compound of formula I at a concentration of from about 0.5% to about 1.5% w/v, about 0.5% to about 2.5% w/v, about 0.5% to about 3.5% w/v, about 0.5% to about 3.0% w/v, about 1.0% to about 2.5% w/v, about 1.5% to about 3.0% w/v, about 0.5% to about 2.5% w/v. In some embodiments, the concentration of the compound of formula I in a formulation for topical ocular use is at least about 0.5% w/v, at least about 1.0% w/v, at least about 1.5% w/v, at least about 2.0% w/v, or at least about 2.5% w/v. In some embodiments, the concentration of the compound of formula I in a formulation for topical use is no more than about 5.0% w/v, no more than about 4.5% w/v, no more than about 4.0% w/v, no more than about 3.5% w/v, or no more than about 3.0% w/v. In particular embodiments, the concentration of the compound of formula I in a formulation for topical use is about 0.5% w/v, about 1.0% w/v, about 1.5% w/v, about 2.0% w/v, about 2.5% w/v, about 3.0% w/v, or about 3.5% w/v. Expressed in units of mg/ml, in some embodiments, compound of formula I is administered to the subject at a concentration of about 5 mg/ml to about 35 mg/ml, about 5 mg/ml to about 25 mg/ml, or about 5 mg/ml to about 15 mg/ml, about 5 mg/ml to about 30 mg/ml, about 10 mg/ml to about 25 mg/ml, about 15 mg/ml to about 30 mg/ml, or about 5 mg/ml to about 25 mg/ml. In some embodiments, the concentration of the compound of formula I in a formulation for topical use is at least about 5 mg/ml, at least about 10 mg/ml, at least about 15 mg/ml, at least about 20 mg/ml, or at least about 25 mg/ml. In some embodiments, the concentration of the compound of formula I in a formulation for topical use is no more than about 50 mg/ml, no more than about 45 mg/ml, no more than about 40 mg/ml, no more than about 35 mg/ml, or no more than about 30 mg/ml. In particular embodiments, the compound of formula I is administered at a concentration of about 5 mg/ml, about 10 mg/ml, about 15 mg/ml, about 20 mg/ml, about 25 mg/ml, about 30 mg/ml, or about 35 mg/ml. In some embodiments, the compound of formula I is present in the form of polymorph A, polymorph B, polymorph C, polymorph E, polymorph F (hydrate $H_A$), polymorph J (acetonitrile solvate $S_A$), polymorph G (methanol solvate $S_B$), polymorph K, polymorph L, or combinations thereof. In particular embodiments, compound I is present as polymorph B in substantially pure form in the ophthalmic formulations described herein. In some embodiments, compound I is present as polymorph A in substantially pure form in the ophthalmic formulations described herein. In some embodiments, compound I is present as substantially pure form as polymorph C in the ophthalmic formulations described herein. In some embodiments, compound I is present as polymorph E in substantially pure form in the ophthalmic formulations described herein. In some embodiments, compound I is present as polymorph F in substantially pure form in the ophthalmic formulations described herein. In some embodiments, compound I is present as polymorph K in substantially pure form in the ophthalmic formulations described herein. In some embodiments, compound I is present as polymorph L in substantially pure form in the ophthalmic formulations described herein. In particular embodiments, compound I is present in the formulation as a mixture of two or more polymorphic forms in different ratios. In some embodiments, compound I is present as a mixture of polymorphs B and E, polymorphs B and F, polymorphs B and C, polymorphs A and C, polymorphs A and F, in ratios of from about 1:99 to about 99:1.

In some embodiments, the formulation further includes at least one ophthalmically acceptable excipient.

In some embodiments, the formulations include an ophthalmically acceptable surfactant. In some embodiments, the surfactant is an anionic surfactant. In specific embodiments, the anionic surfactant is selected from $C_{10}$-$C_{22}$ alkylsulfates, $C_{10}$-$C_{22}$alkyl(oligooxyalkylene)sulfates, $C_4$-$C_{22}$ alkyl sulfosuccinate esters, $C_{10}$-$C_{22}$acylsarcosinatesand $C_{10}$-$C_{22}$ alkylcarboxylates; wherein oligooxyalkylene moieties have from one to five oxy-$C_1$-$C_6$ alkylene moieties, e.g., oxyethylene moieties. The anionic surfactants may have a countercation is selected from alkali metal, e.g., sodium, $C_1$-$C_3$ alkylammonium, tri($C_1$-$C_3$ alkanol)ammonium, e.g., triethanolammonium, di($C_1$-$C_3$ alkanol)ammonium and ammonium cations. The concentration of anionic surfactant in the formulation is from about 0.005 to 0.1 g/L, or 0.005 to 0.05 g/L. In some embodiments, the surfactant is a cationic surfactant. Non-limiting examples of cationic surfactants include alkylamine salts, alkylamine polyoxyethylene adduct, a fatty acid triethanolamine monoester salt, acyl aminoethyl diethylamine salts, fatty acid polyamine condensates, alkyl imidazolines, 1-acyl aminoethyl-2-alkyl imidazoline, 1-hydroxyethyl-2-alkyl imidazoline, include chlorhexidine or the like salts thereof, chlorhexidine or a salt thereof, e.g., chlorhexidine gluconate. In some embodiments, the cationic surfactant is present in the formulation in an amount of from about 0.001 to about 5% w/v, or about 0.001 to about 1% w/v, or about 0.001 to about 0.1% w/v, or about 0.001 to about 0.01% w/v, or about 0.001 to about 0.005% w/v.

In specific embodiments, the surfactant is a non-ionic surfactant. In some embodiments, the non-ionic surfactant is a polysorbate surfactant, a block copolymer of ethylene oxide and propylene oxide surfactant (e.g., a pluronic or tetronic surfactant), poloxamer, tyloxapol, or combinations thereof. Tyloxapol is a nonionic liquid polymer of the alkyl aryl polyether alcohol type. Poloxamers are nonionic triblock copolymers composed of a central hydrophobic chain of polyoxypropylene (poly(propylene oxide)) flanked by two hydrophilic chains of polyoxyethylene (poly(ethylene oxide)). In particular embodiments, the non-ionic surfactant is tyloxapol. In some embodiments, the tyloxapol is present in an amount at least about 0.001% w/v, at least about 0.01% w/v, at least about 0.02% w/v, at least about 0.03% w/v, at least about 0.04% w/v, and no more than about 1% w/v, no more than about 0.5% w/v, no more than about 0.3% w/v, or no more than about 0.2% w/v, no more than about 0.1% w/v, or no more than about 0.08% w/v. In particular embodiments, the non-ionic surfactant is tyloxapol, present in an amount of about 0.03% w/v to 0.08% w/v, or about 0.05% w/v.

In some embodiments, the formulations include about 15-20% w/v of a poloxamer surfactant. In some embodiments, the formulations include about 15, about 15.5%, about 16%, about 16.5%, about 17%, about 17.5%, about 18%, about 18.5%, about 19%, about 19.5%, or about 20% w/v of poloxamer. In particular embodiments, the formulations include about 17.5% w/v poloxamer. In yet particular embodiments, the poloxamer is Poloxamer 407. In particular embodiments, the surfactant is substantially all tyloxapol.

In some embodiments, the formulations include a suspending agent. In some embodiments, the suspending agent is a carbomer, hydroxypropyl methyl cellulose (hypromellose), polyethylene glycol, or combinations thereof. Carbomers are carboxyvinyl polymers that have a network of cross-linked polymer chains. The polymers are often characterized as having carboxylic acid functional groups and may contain from 2 to 7 carbon atoms per functional group. Carbomers, i.e. synthetic high-molecular-weight polymers of acrylic acid that are crosslinked e.g. with allyl sucrose or allyl ethers of pentaerythritol, particularly water-soluble and water-swellable carbomers. Carbomers are available under the trade name CARBOPOL® from various suppliers In particular embodiments, the carbomer is carbomer homopolymer Type B. In particular embodiments, the carbomer is CARBOPOL® 934P (Carbomer 934P), 940 or 974P. In some embodiments, the suspending agent is carbomer and is present in the formulation in an amount of at least about 0.05% w/v, at least about 0.1% w/v, or at least about 0.2% w/v, and no greater than about 1.0% w/v, no greater than about 0.6% w/v, or no greater than about 0.5%. In particular embodiments, the suspending agent is carbomer, and is present in the formulation in an amount of 0.1% w/v to about 0.3% w/v, or about 0.2% w/v.

In some embodiments, the suspending agent is hydroxypropyl methyl cellulose. In particular embodiments, the hydroxypropyl methyl cellulose is present in the formulation in an amount of at least about 0.05% w/v, at least about 0.1% w/v, or at least about 0.25% w/v, and less than about 1.8% w/v, less than about 1.0% w/v, less than about 0.8% w/v, or less than about 0.6% w/v. In some embodiments, the hydroxypropyl methyl cellulose is present in the formulation in an amount of from about 0.1% w/v to about 0.8 w/v %; from about 0.1% w/v to about 0.6% w/v; from about 0.25% w/v to about 0.8% w/v; from about 0.4% w/v to about 0.6% w/v.

In some embodiments, the suspending agent is a polyethylene glycol (PEG) having molecular weight of at least about 200 Da. In some embodiments, the PEG has a molecular weight of at least about 400, 1,000, 2,000, 3,000, 4,000, 6,000, or about 10,000 Da. In some embodiments, the suspending agent is a polyethylene glycol (PEG) having molecular weight of from about 200 to about 20,000 Da. In some embodiments, the PEG has a molecular weight of about 400, 1,000, 2,000, 3,000, 4,000, 6,000, or about 10,000 Da. In some embodiments, the PEG is present in the formulation in an amount of at least 1% w/v, at least about 2% w/v, at least about 3% w/v, and less than about 10% w/v, less than about 9% w/v, or less than about 8% w/v. In particular embodiments, the suspending agent is PEG400 at a concentration of from about 4% w/v to about 9% w/v, about 5% w/v to about 8% w/v, or about 7% w/v. In particular embodiments, the suspending agent is PEG6000 at a concentration of from about 1% w/v to about 4% w/v, about 1% w/v to about 3% w/v, or about 2% w/v.

In particular embodiments, the suspending agent is a combination of more than one suspending agent. In other embodiments, the suspending agent is substantially all carbomer.

In some embodiments, the suspending agent can provide the desired viscosity of the formulation. Without being bound by theory, it is believed that the appropriate viscosity is beneficial in maintaining compound I in a suspended state in the formulation without settling and caking. In some embodiments, the formulation viscosity is from about 10 to about 200 cP (centipoise), from about 20 cP to about 200 cP, or from about 20 cP to about 150 cP. In some embodiments, the formulation viscosity is at least about 10 cP, 20 cP, 50 cP, 100 cP, or at least about 150 cP. Viscosity measurements for the formulations are measured using a Brookfield viscometer using spindle CP-42 at either 3 rpm or 60 rpm. Viscosity is typically measured at room temperature, i.e., 25° C.

In some embodiments, the formulation includes a tonicity agent. In some embodiments, the tonicity agent is a polyol. As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. In some embodiments, the tonicity agent is a polyol such as sugars, sugar alcohols and sugar acids, including, but not limited to: mannitol, glycerin, xylitol, sorbitol and propylene glycol, or combinations thereof. In particular embodiments, the composition includes mannitol, glycerin or a combination thereof. In some embodiments, the amount of polyol in the formulation is from about 0.05% w/v to about 10% w/v, from about 0.1% to about 8% w/v, from about 0.1% to about 7% w/v, from about 0.1% to about 5% w/v. In particular embodiments, the tonicity agent is mannitol or glycerin, which is present in the formulation in an amount of from 0.1% w/v to about 5% w/v, or about 0.2% w/v, about 0.3% w/v, about 0.4% w/v, about 0.5% w/v, about 1% w/v, about 2% w/v, about 2.5% w/v, about 3.0% w/v, about 3.5% w/v, about 4.0% w/v, about 4.5% w/v, or about 5% w/v. In particular embodiments, the tonicity agent is mannitol. In particular embodiments, the tonicity agent is glycerin.

In some embodiments, the formulation includes a buffer. Examples of buffer substances include acetate, ascorbate, borate, hydrogen carbonate, carbonate, citrate, edetate (EDTA) gluconate, lactate, phosphate, propionate and TRIS (tromethamine) buffers. In particular embodiments, the buffer is a phosphate buffering system. In particular embodiments, the buffer is a tromethamine buffer. The amount of buffer substance added is, typically, that necessary to ensure and maintain a physiologically tolerable pH range. In some embodiments, the pH range is in the range of from about 4 to about 9, from about 4.5 to about 8.5, from about 5.0 to about 8.0, from about 5.5 to about 8.0, from about 6.4 to about 8.4. In some embodiments, the pH is about 6.0. In particular embodiments, the pH is about 7.4.

In some embodiments, the formulation includes a salt. In some embodiments, salt is sodium chloride, potassium chloride, calcium chloride, or magnesium chloride. In particular embodiments, the salt is sodium chloride. In particular embodiments, the salt is present in an amount of at least about 0.01% w/v, at least about 0.02% w/v, at least about 0.03% w/v, at least about 0.04% w/v, and no more than about 0.5% w/v, no more than about 0.4% w/v, no more than about 0.3% w/v, no more than about 0.2% w/v, or no more than about 0.1% w/v. In particular embodiments, the salt is present in an amount of from about 0.01% w/v to about 0.5% w/v, from about 0.02% w/v to about 0.4% w/v, from about 0.03% w/v to about 0.3% w/v, from about 0.04% w/v to about 0.2% w/v, from about 0.05% w/v to about 0.1% w/v. In particular embodiments, the salt is sodium chloride and is present in the formulation in an amount of about 0.02% to about 0.07% w/v, or about 0.05% w/v.

In some embodiments, the formulations described herein have an osmolality of about 200 to about 450 milliosmoles per kilogram (mOsm/kg), about 200 to about 400 mOsm/kg, about 200 to about 300 mOsm/kg, or about 240 to about 360 mOsm/kg.

In some embodiments, the formulation may also be self-preserved and does not include a preservative. In other embodiments, the formulation includes a preservative. In some embodiments, the preservative includes, without limitation, polyhexylmethylene biguanidine (PHMB), polymeric quaternary ammonium compound (e.g., polyquaternium-1), chlorine containing preservatives such as benzalkonium chloride (BAK), chlorite preservatives or others.

In some embodiments, the preservative is polymeric quaternary ammonium compounds that are ophthalmically acceptable. Compounds of this type are described in U.S. Pat. Nos. 3,931,319; 4,027,020; 4,407,791; 4,525,346; 4,836,986; 5,037,647 and 5,300,287; and PCT application WO 91/09523 (Dziabo et al). In particular embodiments, the polymeric ammonium compound is polyquaternium 1, otherwise known as POLYQUAD® or ONAMERM® with a number average molecular weight between 2,000 to 30,000. In still particular embodiments, the number average molecular weight is between 3,000 to 14,000.

When used, the polymeric quaternary ammonium compound is generally used in an amount that is greater than about 0.00001 w/v %, greater than about 0.0003 w/v %, or greater than about 0.0007 w/v % of the formulation. Moreover, the polymeric quaternary ammonium compound, when used in the formulation, is generally used at a concentration that is less than about 0.03 w/v %, less than about 0.003 w/v %, or less than about 0.0015 w/v % of the formulation. In some embodiments, the concentration of polymeric quaternary ammonium compound in the formulation are as follows: greater than about 0.0003 w/v % but less than about 0.003 w/v %; greater than about 0.0003 w/v % but less than about 0.0015 w/v %; greater than about 0.0007 w/v % but less than about 0.003 w/v %; and greater than about 0.0007 w/v % but less than about 0.0015 w/v %. In particular embodiments, the formulation includes polyquarternium 1 at a concentration of about 0.001% w/v.

In some embodiments, the formulation includes BAK at a concentration that is at least about 0.0005 w/v %, about 0.001 w/v %, or greater than about 0.007 w/v % of the formulation, and at a concentration that is less than about 0.1 w/v %, less than about 0.02 w/v %, or less than about 0.0035 w/v % of the ophthalmic composition. It is specifically contemplated that any of the lower limits on the concentration of BAK may be used in conjunction with any of the upper limits on the concentrations of BAK. In particular embodiments, the concentration of BAK in the composition are as follows: greater than about 0.001 w/v % but less than about 0.02 w/v %; greater than about 0.001 w/v % but less than about 0.0035 w/v %; greater than about 0.007 w/v % but less than about 0.02 w/v %; and greater than about 0.007 w/v % but less than about 0.0035 w/v %.

In some embodiments, described herein is an aqueous formulation that includes:

4-(7-hydroxy-2-isopropyl-4-oxo-4H-quinazolin-3-yl)-benzonitrile (compound I) or a salt, co-crystal, or polymorph thereof, in an amount of about 0.5% w/v to about 3.5% w/v, and one or more excipients selected from the group consisting of a surfactant, a suspending agent, a tonicity agent, a buffer, a preservative, a salt, and a preservative.

In some embodiments, described herein is an aqueous formulation that includes:

4-(7-hydroxy-2-isopropyl-4-oxo-4H-quinazolin-3-yl)-benzonitrile (compound I) or a salt, co-crystal, or polymorph thereof, present as a suspension in the formulation, in an amount of about 0.5% w/v to about 3.5% w/v, and one or more excipients selected from the group consisting of a surfactant, a suspending agent, a tonicity agent, a buffer, a preservative, a salt, and a preservative.

In some embodiments, described herein is an aqueous formulation that includes:

4-(7-hydroxy-2-isopropyl-4-oxo-4H-quinazolin-3-yl)-benzonitrile (compound I) or a salt, co-crystal, or polymorph thereof, present as a suspension in the formulation, and one or more excipients selected from the group consisting of a surfactant, a suspending agent, a tonicity agent, a buffer, a preservative, a salt, and a preservative.

In some embodiments, described herein is an aqueous formulation that includes:

a suspension of 4-(7-hydroxy-2-isopropyl-4-oxo-4H-quinazolin-3-yl)-benzonitrile (compound I) or a salt, co-crystal, or polymorph thereof, and one or more excipients selected from the group consisting of a surfactant, a suspending agent, a tonicity agent, a buffer, a preservative, a salt, and a preservative.

In some embodiments, described herein is an aqueous formulation that includes:

4-(7-hydroxy-2-isopropyl-4-oxo-4H-quinazolin-3-yl)-benzonitrile (compound I) or a salt, co-crystal, or polymorph thereof, in an amount of about 0.5% w/v to about 3.5% w/v, present as a suspension in the formulation a surfactant, a suspending agent, and one or more excipients selected from the group consisting of a tonicity agent, a buffer, a preservative, a salt, and a preservative.

In some embodiments, the invention described herein is a formulation that includes:

4-(7-hydroxy-2-isopropyl-4-oxo-4H-quinazolin-3-yl)-benzonitrile (compound I) or a salt, co-crystal, or polymorph thereof, in an amount of about 0.5% w/v to about 3.5% w/v, present as a suspension in the formulation, a non-ionic surfactant;

a suspending agent;

a tonicity agent;

a buffer;

a salt; and optionally, a preservative.

In some embodiments, the invention described herein is a formulation that includes:

a suspension of 4-(7-Hydroxy-2-isopropyl-4-oxo-4H-quinazolin-3-yl)-benzonitrile (compound I) or a salt, co-crystal, or polymorph thereof, in an amount of about 0.5% w/v to about 3.5% w/v, a non-ionic surfactant;

a suspending agent;

a tonicity agent;

a buffer;

a salt;

optionally, a preservative; and water qs to 100%.

In some embodiments, the invention described herein is a formulation that includes:

a suspension of 4-(7-Hydroxy-2-isopropyl-4-oxo-4H-quinazolin-3-yl)-benzonitrile (compound I) or a salt, co-crystal, or polymorph thereof, in an amount of about 0.5% w/v to about 2.5% w/v, a non-ionic surfactant selected from tyloxapol, poloxamer, or combinations thereof in an amount of from about 0.01 to 0.2% w/v;

a suspending agent selected from hydroxypropyl methyl cellulose, polyethylene glycol or carbomer homopolymer Type B;

a tonicity agent selected from polyols in an amount of from about 0.05% w/v to about 10% w/v;

a buffer selected from edetate, phosphate, borate, or combinations thereof;

a salt; and water qs to 100%; and a pH in the range of from about 5.5 to about 8.0.

In some embodiments, the invention described herein is a formulation that includes:

a suspension of 4-(7-Hydroxy-2-isopropyl-4-oxo-4H-quinazolin-3-yl)-benzonitrile (compound I) or a salt, co-crystal, or polymorph thereof, in an amount of about 0.5% w/v, about 1.0% w/v, about 1.5% w/v, about 2.0% w/v, or about 2.5% w/v, a non-ionic surfactant selected from tyloxapol in an amount of about 0.04 w/v to about 0.06% w/v, poloxamer in an amount of about 0.005-0.12% w/v, or combinations thereof;

a suspending agent selected from hydroxypropyl methyl cellulose in an amount of from about 0.1% w/v to about 0.8 w/v %, polyethylene glycol in an amount of from about 2% w/v to about 8% w/v, carbomer homopolymer Type B in an amount from about 0.05% w/v to about 0.5% w/v, or combinations thereof;

a tonicity agent selected from mannitol or glycerin in an amount of from about 0.1% w/v to about 5% w/v;

a buffer selected from edetate, phosphate, borate, tromethamine, or combinations thereof;

sodium chloride in an amount of from 0.01% w/v to about 1% w/v;

water qs to 100% and a pH in the range of from about 5.5 to about 8.0.

In some embodiments, the invention described herein is a formulation that includes:

a suspension of 4-(7-Hydroxy-2-isopropyl-4-oxo-4H-quinazolin-3-yl)-benzonitrile (compound I) or a salt, co-crystal, or polymorph thereof, in an amount of about 0.5% w/v, about 1.0% w/v, about 1.5% w/v, about 2.0% w/v, or about 2.5% w/v, tyloxapol in an amount of about 0.04 w/v to about 0.06% w/v;

carbomer homopolymer Type B in an amount from about 0.05% w/v to about 0.4% w/v;

glycerin in an amount of from about 0.5% w/v to about 5% w/v;

a buffer selected from edetate, phosphate, borate, tomethamine, or combinations thereof;

sodium chloride in an amount of from 0.01% w/v to about 1% w/v;

water qs to 100% and a pH in the range of from about 5.5 to about 8.0.

In some embodiments, the invention described herein is a formulation that includes:

a suspension of polymorphic form B of 4-(7-Hydroxy-2-isopropyl-4-oxo-4H-quinazolin-3-yl)-benzonitrile (compound I), in an amount of about 0.5% w/v, about 1.0% w/v, about 1.5% w/v, about 2.0% w/v, or about 2.5% w/v, tyloxapol in an amount of about 0.04 w/v to about 0.06% w/v;

carbomer homopolymer Type B in an amount from about 0.05% w/v to about 0.4% w/v;

glycerin in an amount of from about 0.5% w/v to about 5% w/v;

a buffer selected from edetate, phosphate, borate, tomethamine, or combinations thereof;

sodium chloride in an amount of from 0.01% w/v to about 1% w/v;

water qs to 100% and a pH in the range of from about 5.5 to about 8.0.

In some embodiments, the invention described herein is a formulation that includes:

a suspension of polymorphic form B of 4-(7-Hydroxy-2-isopropyl-4-oxo-4H-quinazolin-3-yl)-benzonitrile (compound I), in an amount of about 0.5% w/v, about 1.0% w/v, about 1.5% w/v, about 2.0% w/v, or about 2.5% w/v, about 0.05% w/v of tyloxapol;

about 0.2% w/v of carbomer homopolymer Type B;

about 2.0% of glycerin;

a tromethamine buffer;

about 0.05% w/v of sodium chloride; and water qs to 100% and a pH in the range of from about 6.4 to about 8.4;

wherein the formulation does not include a preservative.

In some embodiments, acids or bases such as hydrochloric acid, sodium hydroxide, or combinations thereof are used to adjust pH of the formulation. In particular embodiments, hydrochloric acid is used to adjust pH to about 6.0, or about 7.4.

In some embodiments, the formulations described herein are aqueous, that is, they include at least about 90%, at least about 92%, or at least about 95% water.

Without being bound by theory, it is believed that the viscosity of formulations with carbomer homopolymer Type B increases as the pH is adjusted from acidic to neutral, but the viscosity decreases with increasing ionic strength. The present inventors found that using tromethamine as the buffer increases pH without substantial increases in ionic strength. Without further being bound by theory, the inventors also found that glycerin is able adjust the tonicity of the formulation without increasing its ionic strength. Glycerin is also well-tolerated and non-irritating and also serves as a humectant and an additional viscosity agent.

Without being bound by any particular theory, the present inventors also found that inclusion of a surfactant in the formulation acts as a wetting agent for the compound of formula I, thereby providing adequate wetting of the particles of compound I while decreasing the potential for irritation and foaming and aiding in redispersibility of the suspension.

In some embodiments, the formulations described herein further include additional components. In particular embodiments, the formulation includes a cyclodextrin derivative, for example, β-cyclodextrin derivative, γ-cyclodextrin derivative or a combination thereof. In particular embodiments, the cyclodextrin is a hydroxypropyl β-cyclodextrin or sulfoalkylether β-cyclodextrin. When present, the cyclodextrin derivative may be present in an amount of at least about 1.5 w/v %, at least about 3.0 w/v %, at least about 3.5 w/v % or at least about 4.5 w/v, but no greater than about 10.0 w/v %, no greater than about 8.0% w/v, no greater than about 6.5 w/v %, or no greater than about 5.5 w/v. In particular embodiments, the formulation includes about 5% w/v of either hydroxypropyl β-cyclodextrin or sulfoalkylether β-cyclodextrin.

In some embodiments, the formulations of the invention may include an additional therapeutic agent in addition to compound I. Further therapeutic agents may include, for instance, other compounds and antibodies useful for treating ocular surface disorders. A non-limiting list of such agents incudes nonsteroidal anti-inflammatory drugs such as ketorolac, nepafenac, bromfenac, corticosteroids; drugs for dry eye disease such as cyclosprine, lifitegrast, or other TRPV1 inhibitors. In particular embodiments, the additional therapeutic agent is an ophthalmic steroid such as dexamethasone, fluocinolone, loteprednol, difluprednate, fluorometholone, prednisolone, prednisone, medrysone, triamcinolone, betamethasone, rimexolone, or pharmaceutically acceptable salts thereof. Further non-limiting examples of such additional therapeutic agents that may be included in the pharmaceutical composition include Xiidra® (lifitegrast), Restasis® (cyclosporine), minocycline, doxycycline, or other tetracycline antibiotics. Other examples include keratolytic agents such as selenium disulfide, salicylic acid, glycolic acid etc., or pharmaceutically acceptable salts thereof.

In some embodiments, the formulation is stored at refrigerated temperatures (e.g., 4° C.). In some embodiments, the formulation is warmed to room temperature prior to administration.

In some embodiments, the suspension is packaged in a single dose container. In some embodiments, the formulation is packaged in a multi-dose container.

The formulations described herein are delivered to the surface of the eye one to six times a day, depending on the routine discretion of the skilled clinician. In some embodiments, the formulations are administered, one, two, three, or four times a day.

In some embodiments, the formulation exhibits settling of less than about 10% after storage at room temperature for six months. In some embodiments, the formulation exhibits settling of less than about 8%, less than about 7%, less than about 6%, less than about 5%, less than about 4%, less than about 3%, or less than about 2% after storage at room temperature for six months. Settling behavior is measured by methods commonly known to those of skill in the art, for example as described herein.

In some embodiments, the amount of compound I in the formulation is at least 90% of the initial amount after about 6 months of storage under refrigeration (e.g., about 4° C.). In some embodiments, the amount of compound I in the formulation is at least about 90% of the initial amount after about 8 months, about 10 months, about 12 months, about 15 months, or about 18 months of storage under refrigeration. In some embodiments, the amount of compound I in the formulation is at least about 91%, at least about 92%, at least about 93%, at least about 94%, at least about 95%, at least 96%, at least about 97% or at least about 98% of the initial amount after about 6 months of storage under refrigeration (e.g., about 4° C.). In some embodiments, the amount of compound I in the formulation at least about 91%, at least about 92%, at least about 93%, at least about 94%, at least about 95%, at least 96%, at least about 97% or at least about 98% of the initial amount after about 18 months of storage under refrigeration. The amount of compound I in the formulation is measured using methods commonly known to those of skill in the art, for example, HPLC, LC/MS, etc.

In some embodiments, the formulation comprises no more than about 10% of a degradation product after 6 months under refrigeration, wherein the degradation product has a relative retention time of 1.23, compared to compound I, when analyzed by HPMC using a gradient 0.1% trifluoroacetic acid (TFA) water/acetonitrile mobile phase. In some embodiments, the formulation comprises no more than about 9%, no more than about 8%, no more than about 7%, no more than about 6%, no more than about 5%, no more than about 4%, no more than about 3%, or no more than about 2% of a degradation product after 6 months under refrigeration.

In some embodiments, no more than about 10% of compound I in the formulation degrades upon storage for 12 weeks at 40° C. In particular embodiments, no more than about 9%, no more than about 8%, no more than about 7%, no more than about 6%, no more than about 6%, no more than about 5%, no more than about 4%, no more than about 3%, no more than about 2% of compound I in the formulation degrades upon storage for 12 weeks at 40° C.

In some embodiments, the pharmaceutical formulations of the invention may include an additional therapeutic agent in addition to Compound (I). Further therapeutic agents may include, for instance, other compounds and antibodies useful for treating ocular surface disorders. A non-limiting list of such agents incudes nonsteroidal anti-inflammatory drugs such as ketorolac, nepafenac, bromfenac, corticosteroids; drugs for dry eye disease such as cyclosporine, lifitegrast, or other TRPV1 inhibitors. In particular embodiments, the additional therapeutic agent is an ophthalmic steroid such as dexamethasone, fluocinolone, loteprednol, difluprednate, fluorometholone, prednisolone, prednisone, medrysone, triamcinolone, betamethasone, rimexolone, or pharmaceutically acceptable salts thereof. Further non-limiting examples of such additional therapeutic agents that may be included in the pharmaceutical composition include Xiidra® (lifitegrast), Restasis® (cyclosporine), minocycline, doxycycline, or other tetracycline antibiotics. Other examples include keratolytic agents such as selenium disulfide, salicylic acid, glycolic acid etc., or pharmaceutically acceptable salts thereof.

Methods of Making

In some embodiments, the formulation is prepared by mixing an amount of 4-(7-hydroxy-2-isopropyl-4-oxo-4H-quinazolin-3-yl)-benzonitrile (compound I) or a salt, co-crystal, or polymorph thereof, and one or more excipients selected from the group consisting of a surfactant, a suspending agent, a tonicity agent, a buffer, a preservative, a salt, and a preservative.

In some embodiments, the present invention provides a method of making the pharmaceutical formulations of compound I. In some embodiments, the formulation is prepared by mixing an amount of 4-(7-Hydroxy-2-isopropyl-4-oxo-4H-quinazolin-3-yl)-benzonitrile (compound I) or a salt, co-crystal, or polymorph thereof, a non-ionic surfactant;
a suspending agent;
a tonicity agent;
a buffer;
a salt;
optionally, a preservative; and
water qs to 100%, and
adjusting the pH to a range of from about 5.5 to about 8.0.

In some embodiments, the compound I is added as a stock suspension in water, optionally with the surfactant. In some embodiments, the compound I is present in an amount of 10% in the stock suspension. In alternative or additional embodiments, the stock suspension of compound I further includes 0.2% tyloxapol. In some embodiments, the stock suspension of compound I is milled to achieve a desired particle size of compound I. In some embodiments, the $D_{90}$ of compound I in the formulation (diameter at which 90% of compound I is comprised of smaller particles) is below about 10 μm, below about 8 μm, below about 6 μm, below about 4 μm, below about 3 μm, or about 2 μm. In some embodiments, the $D_{50}$ of compound I in the formulation (diameter at which 50% of compound I is comprised of smaller particles) is below about 10 μm, below about 8 μm, below about 6 μm, below about 4 μm, below about 3 μm, below about 2 μm, or about 1 μm. In some embodiments, the $D_{10}$ of compound I in the formulation (diameter at which 10% of compound I is comprised of smaller particles) is below about 5 μm, below about 4 μm, below about 3 μm, below about 2 μm, below about 1 μm, or about 0.3 μm.

In particular embodiments, the non-ionic surfactant, the suspending agent, the tonicity agent, buffer, and salt are as noted supra. In some embodiments, the formulation does not include a preservative.

An exemplary method of manufacture of a 1.5% w/v compound I suspension is described below:

1. Tare a clean, dry glass Schott bottle with a polybutylene terephthalate, PTFE-lined cap and a magnetic stir bar.
2. Add the batch quantity of compound I vehicle (including suspending agent, tonicity agent, surfactant, and salt, and pH adjusted to final pH) to the bottle. Seal and steam sterilize the compounding vessel ($F_0 \geq 30$).
3. Transfer the vessel to a horizontal laminar flow workbench and allow to cool.
4. Aseptically weigh and add the batch quantity of sterile 10% compound I/0.2% surfactant to the compounding vessel. Adjust to final batch weight, if necessary, with sterile (either steam sterilized or aseptically filtered) Purified Water qs and stir until uniform.

5. Aseptically fill the 1.5% suspension into sterile dispensing bottles. Insert suspension tips and tighten screw-on closures to seat tips and seal.
6. Remove filled units from laminar flow workbench and label. Measure the final pH and osmolality values.

Methods of Use

Without being bound by theory, it is hypothesized that blockers of the Transient Receptor Potential Vanilloid 1 (TRPV1) receptor may be useful in the treatment of pain, e.g., chronic pain.

Accordingly, in some embodiments, the invention provides a method of treating ocular surface pain in a subject, said method includes administering to the subject an effective amount of compound (I), or a pharmaceutically acceptable salt, solvate, or co-crystal thereof. In some embodiments, the invention provides a method of reducing ocular surface pain in a subject in need thereof, said method includes administering to the subject an effective amount of compound (I), or a pharmaceutically acceptable salt, solvate, or co-crystal thereof. In some embodiments, the invention provides for the use of the compound of formula I, or a pharmaceutically acceptable salt, solvate, or co-crystal thereof, in the treatment or reduction of ocular surface pain. In some embodiments, the compound of formula I is in polymorphic form B. In particular embodiments, the methods described herein are carried out by administering the formulations of compound I described supra. Thus, the invention provides a method of treating ocular surface pain by administering a formulation of compound I as described herein. In some embodiments, the method results in a reduction in ocular surface pain.

In some embodiments, the subject suffers from episodic or acute ocular pain. In some embodiments, the subject suffers from chronic ocular surface pain, which lasts for at least three months. In some embodiments, the subject suffers from chronic ocular surface pain, which lasts for at least two months. In some embodiments, the subject suffers from chronic ocular surface pain, which lasts for at least one month. In some embodiments, the subject suffers from chronic ocular surface pain, which lasts for at least four months. In some embodiments, the subject suffers from chronic ocular surface pain, which lasts for at least five months. Thus, in some embodiments, the invention provides a method of treating chronic ocular surface pain in a subject by administering to the subject an effective amount of compound of formula I, or a salt, solvate, polymorph, or co-crystal thereof. In some embodiments, the invention provides a method of reducing chronic ocular surface pain in a subject by administering to the subject an effective amount of compound of formula I, or a salt, solvate, polymorph, or co-crystal thereof. The invention provides for the use of the compound of formula I, or a pharmaceutically acceptable salt, solvate, polymorph, or co-crystal thereof, in the treatment of chronic ocular surface pain. In some embodiments, the compound of formula I is in a formulation as described herein.

In some embodiments, the formulation is administered to the ocular surface of the subject, e.g., any part of the cornea, conjunctiva, or to the cul de sac of the eye.

In some embodiments, the invention provides for the administration of the compound of formula I to a subject in need thereof in a ophthalmically compatible formulation at a concentration of about 0.5% w/v to about 3.5% w/v. In some embodiments, concentrations for administration range from about 0.5% to about 3.5% w/v, about 0.5% to about 2.5% w/v, about 0.5% to about 1.5% w/v, about 0.5% to about 3.0% w/v, about 1.0% to about 2.5% w/v, about 1.5% to about 3.0% w/v, about 0.5% to about 2.5% w/v. In some embodiments, the concentration of the compound I in an ophthalmically compatible formulation is at least about 0.5% w/v, at least about 1.0% w/v, at least about 1.5% w/v, at least about 2.0% w/v, or at least about 2.5% w/v. In some embodiments, the concentration of the compound of formula I in a formulation for topical use is no more than about 5.0% w/v, no more than about 4.5% w/v, no more than about 4.0% w/v, no more than about 3.5% w/v, or no more than about 3.0% w/v. In particular embodiments, the concentration of the compound of formula I in a formulation for topical use is about 0.5% w/v, about 1.0% w/v, about 1.5% w/v, about 2.0% w/v, about 2.5% w/v, about 3.0% w/v, or about 3.5% w/v. In some embodiments, the dose per administration per eye is from about 0.15 to about 1.15 mg, or about 0.15 mg, 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, about 1.0 mg, about 1.05 mg, about 1.1 mg, or about 1.15 mg. In some embodiments, the dose per administration per eye is about 0.18 mg, about 0.37 mg, about 0.55 mg, about 0.74 mg, or about 0.92 mg. In some embodiments, the total daily dose per eye is about 0.5 to about 3.5 mg, or about 0.5 mg, about 1.0 mg, about 1.5 mg, about 2.0 mg, about 2.5 mg, about 3.0 mg, or about 3.5 mg. In some embodiments, the compound of formula I is administered to the subject one to six times a day, e.g., one, two, three, or four times a day. In some embodiments, the compound of formula I is administered to the subject for a period of at least about one month, at least about two months, or at least about three months. In some embodiments, the compound of formula I is administered to the subject for a period of at least about 12 weeks.

In some embodiments, the ocular surface pain or the chronic ocular surface pain is associated with one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis. In some embodiments of the methods described herein, the subject suffers from ocular pain persisting for at least three months after photorefractive keratectomy (PRK) surgery or laser-assisted in situ keratomileusis (LASIK) surgery.

In particular embodiments, the ocular surface pain or the chronic ocular surface pain is associated with dry eye disease or Sjogren's Syndrome. In some embodiments, the subject suffers from conjunctivitis, subconjunctival hemorrhage, subconjunctival scarring, conjunctival membranes, conjunctival ulceration, superficial punctate epithelial erosions, epithelial defects, lid margin ulceration, lid margin keratinization, symblepharon, ankyloblepharon, trichiasis, anterior blepharitis, punctal auto-occlusion, meibomian gland disease, corneal opacification, dry eye, districhiasis, limbal stem cell failure, or corneal vascularization.

In some embodiments, the administration of compound of formula I results in a reduction in the subject's ocular pain, compared to a placebo. In some embodiments, the reduction in the subjects ocular pain is at least about 3 when measured on the VAS score, compared to a placebo. In some embodiments, the administration results in a reduction in the subject's ocular pain of at least about 4, at least about 5, at least about 6, at least about 7, at least about 8, at least about 9, or at least about 10, when measured on the VAS score, compared to a placebo. In some embodiments, the administration results in a reduction in the subject's pain of at least about 10%, at least about 15%, at least about 20%, or at least about 25%, compared to a placebo.

In some embodiments, the administration of the compound of formula I results in a reduction in the subject's pain of at least about 2 compared to a placebo, as measured by the VAS score, about half hour after the administration, about one hour, about 2 hours, or about 2-4 hours after the administration. In some embodiments, the administration results in a reduction in the subject's pain, when measured after 7 days of administration of the compound of formula I. In some embodiments, the administration results in a reduction in the subject's pain, when measured after 14 days of administration of the compound of formula I.

In some embodiments, the reduction in pain score arises from the difference in pain scores prior to and after administration of compound I to the subject. In some embodiments, the reduction in pain score as measured by the VAS, arises from the difference in pain scores prior to and after administration of compound I to the subject. In some embodiments, the reduction in pain score occurs within about half hour after administration of compound I to the subject. In some embodiments, the reduction in pain score occurs within about 1 hour, about 2 hours, about 3 hours, about 4 hours, about 5 hours, or about 6 hours after administration of compound I to the subject. In some embodiments, the administration results in a reduction in the subject's pain, when measured after 7 days of administration of the compound of formula I. In some embodiments, the administration results in a reduction in the subject's pain, when measured after 14 days of administration of the compound of formula I.

In some embodiments, the administration of the compound of formula I results in an improved score on at least one question of the OPAS of at least about 10%, at least about 20%, or at least about 30%.

In some embodiments, the administration of the compound of formula I results in an improved score on at least one question of the Visual Tasking Questionnaire of at least about 10%, at least about 20%, or at least about 30%.

In some embodiments, the administration of the compound of formula I results in reduced ocular hyperemia (redness of the eye), compared to placebo. In particular embodiments, the administration of the compound of formula I results in reduced grade 1, grade 2, grade 3, or grade 4 hyperemia compared to placebo.

In some embodiments, the administration results in a reduction in ocular hyperemia score of at least about 1, at least about 2, at least about 3, at least about 4, or at least about 5, on the McMonnies scale.

Thus, in some embodiments, the present invention relates to a method of treating or reducing ocular hyperemia in a subject in need thereof, comprising administering to the subject an effective amount of compound of formula I, or a salt, solvate, polymorph, or co-crystal thereof. In some embodiments, the invention provides for the use of the compound of formula I, or a pharmaceutically acceptable salt, solvate, or co-crystal thereof, in the treatment of ocular hyperemia. In some embodiments, the administration results in a reduction in ocular hyperemia score of at least about 1, at least about 2, at least about 3, at least about 4, or at least about 5, on the McMonnies scale. In some embodiments, the invention provides for the administration of the compound of formula I to a subject in need thereof in a ophthalmically compatible formulation at a concentration of about 0.5% w/v to about 3.5% w/v. In some embodiments, concentrations for administration range from about 0.5% to about 3.5% w/v, about 0.5% to about 2.5% w/v, about 0.5% to about 1.5% w/v, about 0.5% to about 3.0% w/v, about 1.0% to about 2.5% w/v, about 1.5% to about 3.0% w/v, about 0.5% to about 2.5% w/v. In particular embodiments, the concentration of the compound of formula I in a formulation for topical use is about 0.5% w/v, about 1.0% w/v, about 1.5% w/v, about 2.0% w/v, about 2.5% w/v, about 3.0% w/v, or about 3.5% w/v. In some embodiments, the dose per administration per eye is from about 0.15 to about 1.15 mg, or about 0.15 mg, 0.2 mg, about 0.25 mg, 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, about 1.0 mg, about 1.05 mg, about 1.1 mg, or about 1.15 mg. In some embodiments, the dose per administration per eye is about 0.18 mg, about 0.37 mg, about 0.55 mg, about 0.74 mg, or about 0.92 mg. In some embodiments, the total daily dose per eye is about 0.5 to about 3.5 mg, or about 0.5 mg, about 1.0 mg, about 1.5 mg, about 2.0 mg, about 2.5 mg, about 3.0 mg, or about 3.5 mg. In some embodiments, the compound of formula I is administered to the subject one to six times a day, e.g., one, two, three, or four times a day. In some embodiments, the compound of formula I is administered to the subject for a period of at least about one month, at least about two months, or at least about three months. In particular embodiments, the compound of formula I is administered in a formulation described herein.

In some embodiments, the ocular hyperemia is associated with one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis. In some embodiments of the methods described herein, the ocular hyperemia persists for at least three months after photorefractive keratectomy (PRK) surgery or laser-assisted in situ keratomileusis (LASIK) surgery.

In some embodiments, the ocular surface pain or chronic ocular surface pain is associated with dry eye disease. In some embodiments, the administration of the compound of formula I results in a decrease in the symptoms of dry eye disease. Dry eye disease is generally understood to be a complex, multifactorial condition characterized by inflammation of the ocular surface and lacrimal glands and reductions in the quality and/or quantity of tears. It is believed that up to 30% of dry eye disease patients suffer from ocular surface pain that may be chronic. Thus, in some embodiments, the invention results in a decrease of at least about 10%, at least about 15%, at least about 20%, or at least about 30% in the symptoms of dry eye disease, including one or more of ocular dryness, ocular discomfort, ocular hyperemia, ocular burning or stinging, grittiness or foreign body sensation, or photophobia.

In some embodiments, the invention relates to a method of treating dry eye disease in a subject in need thereof, comprising administering to the subject an effective amount of compound of formula I, or a salt, solvate, polymorph, or co-crystal thereof. In some embodiments, the invention relates to a method of treating dry eye disease in a subject in need thereof, comprising administering to the subject an effective amount of compound of formula I, or a salt, solvate, polymorph, or co-crystal thereof, wherein the compound of formula I is safe for administration over a period of at least 2 months, at least 3 months, at least 4 months, or at least 5 months. In particular embodiments, the invention provides for the use of the compound of formula I, or a pharmaceutically acceptable salt, solvate, or co-crystal thereof, in the treatment of dry eye disease. In some embodiments, the invention results in a decrease of at least about 10% in the symptoms of dry eye disease, including one or more of ocular dryness, ocular discomfort, ocular hyperemia, ocular burning or stinging, grittiness or foreign body sensation, or photophobia. In some embodiments, the invention provides for the administration of the compound of formula I to a subject in need thereof in a ophthalmically compatible formulation at a concentration of about 0.5% w/v to about 3.5% w/v. In some embodiments, concentrations for administration range from about 0.5% to about 3.5% w/v, about 0.5% to about 2.5% w/v, about 0.5% to about 1.5% w/v, about 0.5% to about 3.0% w/v, about 1.0% to about 2.5% w/v, about 1.5% to about 3.0% w/v, about 0.5% to about 2.5% w/v. In particular embodiments, the concentration of the compound of formula I in a formulation for topical use is about 0.5% w/v, about 1.0% w/v, about 1.5% w/v, about 2.0% w/v, about 2.5% w/v, about 3.0% w/v, or about 3.5% w/v. In some embodiments, the dose per administration per eye is from about 0.15 to about 1.15 mg, or about 0.15 mg, 0.2 mg, about 0.25 mg, 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, about 1.0 mg, about 1.05 mg, about 1.1 mg, or about 1.15 mg. In some embodiments, the dose per administration per eye is about 0.18 mg, about 0.37 mg, about 0.55 mg, about 0.74 mg, or about 0.92 mg. In some embodiments, the total daily dose per eye is about 0.5 to about 3.5 mg, or about 0.5 mg, about 1.0 mg, about 1.5 mg, about 2.0 mg, about 2.5 mg, about 3.0 mg, or about 3.5 mg. In some embodiments, the compound of formula I is administered to the subject one to six times a day, e.g., one, two, three, or four times a day. In some embodiments, the compound of formula I is administered to the subject for a period of at least about one month, at least about two months, or at least about three months. In some embodiments, the compound of formula I is administered as a formulation described herein.

In some embodiments of the methods described herein, the administration of the compound of formula I does not result in a change (e.g., of less than 5% difference, less than 4% difference, or less than 3% difference) in one or more of best corrected visual acuity, slit-lamp biomicroscopy, dilated eye exam, blink rate, tear production, intraocular pressure or corneal staining, compared to a placebo. In some embodiments of the methods described herein, the administration of compound of formula I does not result in a delay in wound healing compared to a placebo in a patient in need thereof.

Patient Population

In specific embodiments, a subject to be treated by methods provided herein suffers from an ocular surface disorder. Non-limiting examples of ocular surface disorders include chronic ocular surface pain (COSP), dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis. In some embodiments, the subject suffers from ocular pain persisting for at least three months after photorefractive keratectomy (PRK) surgery or laser-assisted in situ keratomileusis (LASIK) surgery.

In certain embodiments, methods provided herein is for treating, or reducing, ocular surface pain, such as acute ocular surface pain.

In certain embodiments, methods provided herein is for treating, or reducing, ocular surface pain, such as chronic ocular surface pain (COSP). In particular aspects, COSP is characterized as persistent ocular surface pain (e.g., persistent severe ocular surface pain) that can distract from, or can interfere with, regular daily activities. In specific aspects, COSP can result in poor quality of life, and can persist for at least 1 month, at least 2 months, at least 3 months, at least 4 months, at least 5 months, or at least 6 months. In some aspects, COSP can persist for at least about 2 months or at least about 3 months. In other aspects, COSP can persist for at least 3 months or at least 4 months. In particular aspects, subject with COSP remain symptomatic despite adherence to other therapies indicated for their underlying disease (e.g., an ocular surface disorder such as dry eye disease or Sjogren's Syndrome).

In some embodiments, the subject to be treated suffers from ocular neuropathic pain (ONP). ONP is a spectrum of disorders of ocular pain that may be caused by damage or disease affecting the nerves, e.g., corneal nerves. Symptoms of ONP may include one or more of eye pain, sensitivity to light, hyperalgesia or dysesthesia (abnormal sensations) such as a sensation of dryness, stinging, or foreign body, pain from normally non-painful stimuli (allodynia). Gabapentin and other neuropathic pain medications may be used to blunt sensory nerve stimulation or the perception of nerve stimulation.

In some embodiments, the subject to be treated suffers from exposure keratopathy. EK is damage to the cornea that occurs primarily from prolonged exposure of the ocular surface to the outside environment. EK can lead to ulceration, microbial keratitis, and permanent vision loss from scarring. Patients at risk for EK include those who suffer from conditions that interfere with the ability to protect the cornea; either by incomplete eyelid closure (e.g., lagophthalmos, proptosis, lid malposition), inadequate blink reflex, inadequate blink rate (for example, caused by a neurologic disease, e.g., Parkinson disease, a neuromuscular disease) and/or decreased protective lubrication of the cornea. Symptoms of EK include foreign body sensation, burning, increased tearing, and intermittent blurry vision (from an unstable tear film), pain and photophobia. Standard treatments include the use of frequent artificial tears with nightly lubricating ointment, punctal plugs.

In some embodiments, the subject to be treated suffers from keratoconjunctivitis. Keratoconjuctivitis is an inflammatory process that involves both the conjunctiva and the cornea. Superficial inflammation of the cornea (keratitis) occurs commonly in association with viral and bacterial conjunctivitis, for example in adults. The following types of keratoconjuctivitis are distinguished based on the potential cause of inflammation:

- Keratoconjunctivitis sicca is cause by the inflammation due to dryness;
- Vernal keratoconjunctivitis (VKC) occurs seasonally, considered to be due to allergens;
- Atopic keratoconjunctivitis is one manifestation of atopy;
- Epidemic keratoconjunctivitis or adenoviral keratoconjunctivitis is caused by an adenovirus infection;
- Infectious bovine keratoconjunctivitis (IBK) is a disease affecting cattle caused by the bacteria *Moraxella bovis;*
- Pink eye in sheep and goat is mostly caused by *Chlamydophila pecorum;*
- Superior limbic keratoconjunctivitis is thought to be caused by mechanical trauma;
- Keratoconjunctivitis photoelectrica (arc eye) means inflammation caused by photoelectric UV light.

In some embodiments, the subject to be treated suffers from dry eye. The term "dry eye" as used herein, refers to inadequate tear production and/or abnormal tear composition. Dry eye syndrome disease (DEDS), also known as dry eye syndrome, keratoconjunctivitis sicca or keratitis sicca, or tear dysfunction syndrome, or burning eye syndrome results from deficiency of any of the tear film layers. Dry eye is a multifactorial disease of the tears and ocular surface that results in symptoms of discomfort, visual disturbance, and tear ¬film instability with potential damage to the ocular surfaceocular surface characterized by loss of homeostasis of the tear film, and accompanied by ocular symptoms, in which tear film instability and hyperosmolarity, ocular surface inflammatoin and damage, and neuro-sensory abnormalities play etiological roles (Craig J P, et al., The Ocular Surface 2017; 15:276-83). It may be accompanied by increased osmolarity of the tear film and inflammation of the ocular surface. Dry eye disorder may range from mild to moderate to severe forms. Symptoms of dry eye syndrome disease include gritty, foreign body sensations, burning, photophobia, and decreased visual acuity, tearing, stinging, itching, sandy or gritty feeling, discharge, frequent blinking, mattering or caking of the eyelashes (usually worse upon waking), redness, blurry or fluctuating vision (made worse when reading, computer, watching television, driving, or playing video games), light-sensitivity, eye pain and/or headache, heavy eye lids, eye fatigue. Causes of dry eye disease include, but are not limited to, the following: idiopathic, congenital alacrima, xerophthalmia, lacrimal gland ablation, and sensory denervation; collagen vascular diseases, including rheumatoid arthritis, Wegener's granulomatosis, and systemic lupus erythematosus; Sjögren's Syndrome and autoimmune diseases associated with Sjögren's syndrome; abnormalities of the lipid tear layer caused by blepharitis or rosacea; abnormalities of the mucin tear layer caused by vitamin A deficiency; trachoma, diphtheric keratoconjunctivitis; mucocutaneous disorders; aging; menopause; and diabetes. Dry eye signs and/or symptoms as defined herein may also be provoked by other circumstances, including but not limited to the following: prolonged visual tasking; working on a computer; being in a dry environment; warm or cold wind or air flow; seasonal changes; ocular irritation; contact lenses, LASIK and other refractive surgeries; fatigue; and medications such as isotretinoin, sedatives, diuretics, tricyclic antidepressants, antihypertensives, oral contraceptives, antihistamines, nasal decongestants, beta-blockers, phenothiazines, atropine, and pain relieving opiates such as morphine.

Diagnostic testing for dry eye includes evaluation of cornea sensation (corneal hyperesthesia and/or reduced sensation may be present in severe and chronic dry eye disease) using, for example, a cotton tip applicator or more precisely with a Cochet-Bonnet esthesiometer; measuring tear break up time using, for example, a fluorescein-impregnated strip wet with non-preserved saline solution or more objective computerized methods without the need for fluorescein instillation; performing ocular surface staining, e.g., fluorescein sodium, rose bengal, lissamine green; performing Schirmer test (relatively insensitive for patients with mild dry eye), testing delayed tear clearance; tear meniscus height; measuring level of MMP-9 (MMP-9 has been shown to be elevated in the tears of patient with dry eye disease, and levels correlate with examination findings in patients with moderate to severe dry eye); measuring tear osmolarity and tear film interferometry; performing Sjo test (detection of SS-A (anti-Ro) and SS-B (anti-La) autoantibodies in serum, salivary gland protein 1 (SP-1), carbonic anhydrase 6 (CA6), and parotid secretory protein (PSP). SP-1, CA6, and PSP).

Artificial tears, lubricating ointments, corticosteroids (e.g., loteprednol 0.5% eyedrops four times a day) are used as an initial treatment. Prescription medicines include cyclosporine, lifitegrast, diquafosol, rebamepide, corticosteroids (e.g., loteprednol 0.5% eyedrops four times a day).

The term "tear film dysfunction" refers to a state when the tear film breaks down in different places on the cornea and conjunctiva, leading not only to symptoms of irritation, but also to unstable and intermittently changing vision. For example, dry eye syndrome disease is characterized by tear film dysfunction. The symptoms of tear film dysfunction include tearing, burning, stinging, itching, sandy or gritty feeling, scratchy or foreign-body sensation, discharge, frequent blinking, mattering or caking of the eyelashes (usually worse upon waking), redness, blurry or fluctuating vision (made worse when reading, computer, watching television, driving, or playing video games), light-sensitivity, eye pain and/or headache, heavy eye lids, eye fatigue.

Adenoviral keratoconjunctivitis, also known as Keratoconjunctivitis epidemica is a common and highly contagious viral infection of the eye. The clinical course of Adenoviral keratoconjunctivitis is divided into an acute phase with conjunctival inflammation of varying intensity with or without corneal involvement and a chronic phase with corneal opacities.

Vernal keratoconjunctivitis (VKC) is an atopic condition of the external ocular surface characterized by symptoms consisting of severe itching, photophobia, foreign body sensation, mucous discharge (often described as "ropy"), blepharospasm, and blurring of vision (Buckley, R. J., *Int Ophthalmol Clin,* 1988 28(4): p. 303-8; Kumar, S., *Acta Ophthalmologica,* 2009. 87(2): p. 133-147). It is typically bilateral but may be asymmetric in nature. It characteristically affects young males in hot dry climates in a seasonal manner; in 23% of patients may have a perennial form (Kumar, S., *Acta Ophthalmologica,* 2009. 87(2): p. 133-147; Bonini, S., et al., *Ophthalmology,* 2000. 107(6): p. 1157-63).

The signs of VKC can be divided into conjunctival, limbal and corneal signs:

- Conjunctival signs include diffuse conjunctival injection and upper tarsal giant papillae that are discrete >1 mm in diameter;
- Limbal signs include thickening and opacification of the limbal conjunctiva as well as gelatinous appearing and sometime confluent limbal papillae. Peri-limbal Horner-Trantas dots are focal white limbal dots consisting of degenerated epithelial cells and eosinophils (Buckley, R. J., *Int Ophthalmol Clin,* 1988. 28(4): p. 303-8);
- Corneal signs vary according to the severity of the disease process and include macro-erosions, cornal ulcers and scars (Buckley, R. J., *Int Ophthalmol Clin,* 1988. 28(4): p. 303-8).

Active VKC patients (defined as moderate to severe ocular discomfort including photophobia, papillae on the upper tarsal conjunctiva, or limbal Horner-Trantas dots clearly recognizable at the time of the examination) showed significantly increased symptoms and signs of ocular surface disease. Inactive VKC patients (defined as no symptoms or mild discomfort, and absence of corneal abnormalities at the time of the examination) showed increased photophobia, conjunctival lissamine green staining and Schirmer test values, and reduced fluorescein break-up time (BUT) and corneal sensitivity. This syndrome seems to affect the ocular surface in all phases (active and quiescent), determining abnormalities in tear film stability, epithelial cells integrity, and corneal nerves function (Villani E. et al., *Medicine* (Baltimore). 2015 October; 94(42): e1648).

The following factors are thought to play a role in VKC: IgE mediate reaction via mast cell release; activated eosinophils, mononuclear cells and neutrophils as well as the CD4 T-helper-2 driven type IV hypersensitivity with immunomodulators such as IL-4, IL-5, and bFGF (Buckley, R. J., *Int Ophthalmol Clin,* 1988. 28(4): p. 303-8; Kumar, S., *Acta Ophthalmologica,* 2009. 87(2): p. 133-147; La Rosa, M., et al., *Ital J Pediatr,* 2013. 39: p. 18).

Treatment consists of cool compresses and lid scrubs, saline eyedrops, which may help to relieve symptoms, along with topical antihistamines, nonsteroidal anti-inflammatory drugs or corticosteroids, e.g., low-absorptions corticosteroids (fluoromethelone, loteprednol, remexolone, etc.), optical mast cell stabilizers (cromolyn sodium, nedocromil sodium, and lodoxamide), topical cyclosporin-A, or tacrolimus. See e.g., Oray, M. and E. Toker, Cornea, 2013. 32(8): p. 1149-54: Vichyanond, P. and P. Kosrirukvongs, *Curr Allergy Asthma Rep,* 2013. 13(3): p. 308-14; Barot, R K et al., *J Clin Diagn Res.* 2016 June; 10(6):NC05-9; Wan Q et al., *Ophthalmic Res.* 2018; 59(3):126-134.

Atopic keratoconjunctivitis (AKC) typically has an older age of onset in the 2nd to 5th decade, as opposed to onset prior to age 10 with VKC. Conjunctival involvement is classically on the upper tarsus in VKC and on the lower tarsus in AKC. AKC is typically more chronic in nature and more commonly results in scarring of the cornea and conjunctival cicatrization.

Sjogren's Syndrome (Sjogren's syndrome associated with dry eye) is a chronic inflammatory disorder characterized by exocrine gland dysfunction including the salivary and lacrimal glands that in many cases results in a severe dry eye. Primary symptoms are dry eyes (keratitis sicca or keratoconjunctivitis sicca) and dry mouth (xerostomia). Severe dry eyes can cause corneal pain, corneal scarring, ulceration, infection, and even perforation. The differential diagnosis includes conditions such as adult blepharitis, dry eye disease, and juvenile idiopathic arthritis uveitis, as well keratopathies, e.g., superficial punctate, filamentary, neurotrophic, exposure). Treatment of Sjogren's syndrome is aimed at maintaining the integrity of the tear film through preservation, augmentation, and/or replacement of the deficient tear secretion. Treatment of Sjogren's syndrome thus includes artificial tears and lubricating ointments; autologous serum eyedrops; oral omega-6 essential fatty acids; fluid-ventilated, gas permeable scleral lenses; topical corticosteroids; punctal occlusion to decrease tear drainage; a small lateral tarsorrhaphy; humidification of the environment; hydrophilic bandage lenses; bromhexine and 3-isobutyl 1-methylxanthine (IBMX) (augmentation of tear production/secretion); agents to stimulate muscarinic receptors (pilocarpine and cevimeline); immunosuppressive agents, e.g., methotrexate, antimalarials, cyclophosphamide, leflunomide, or tumor necrosis factor (TNF), e.g., infliximab, a monoclonal antibody to TNF-alpha; Cyclosporin A; the bandage contact lens.

Steven-Johnson's syndrome (SJS) is a dermatologic emergency or a type of severe skin reaction characterized by the presence of epidermal and mucosal bullous lesions involving less than 10% of the total body surface area. Early symptoms of SJS include fever and flu-like symptoms, which may precede or occur concurrently with the development of a macular rash involving the trunk and face. As the disease progresses, the macular rash coalesces, the involved areas develop bullae, and the epidermal layer eventually sloughs off. During the acute phase of SJS-TEN, 80% of patients will have ocular involvement.

The constellation of high fever (>102.2), malaise, arthralgia, a macular rash involving the trunk, neck and face, and recent history of new medication exposure or recently increased dosage of an existing medication are indicators used for diagnosis of SJS. A skin biopsy of an effected area can be performed for a confirmation of the diagnosis. Granulysin can be used as a marker for the diagnosis of SJS. The concentration of granulysin within bullous fluid correlates with the severity of the acute phase of SJS (Chung W H, et al. *Nat Med.* 2008; 14(12):1343-50).

Ocular manifestations in SJS include conjunctivitis, subconjunctival hemorrhage, subconjunctival scarring, conjunctival membranes, conjunctival ulceration, superficial punctate epithelial erosions, epithelial defects, lid margin ulceration, lid margin keratinization, symblepharon, ankyloblepharon, trichiasis, anterior blepharitis, punctal autoocclusion, meibomian gland disease, corneal opacification, dry eye, districhiasis, limbal stem cell failure, corneal vascularization. Eye treatment in SJS consists of saline eyedrops, preservative-free artificial tears and ointments to provide adequate lubrication and reduce epithelial injury.

Patients with any corneal or conjunctival epithelial defects are treated with prophylactic topical antibiotics, e.g., a fourth generation fluoroquinolone. Patients having mild or moderate ocular involvement (less than one-third lid margin involvement, conjunctival defects less than 1 cm at greatest diameter, and no corneal epithelial defects) are typically treated with topical moxifloxacin 0.5% four times a day, cyclosporine 0.05% twice daily, and topical steroids (prednisolone acetate 1% four to eight times a day or dexamethasone 0.1% twice daily). Patients having severe or extremely severe ocular involvement (greater than one-third lid margin involvement, conjunctival defects greater than 1 cm, and corneal epithelial defects) undergo an amniotic membrane (AM) grafting in addition to the treatments listed above.

In some embodiments, the subject to be treated suffers from corneal epithelipathy. Corneal epitheliopathy is a disease involving corneal epithelium, e.g., manifested in altered corneal epithelial barrier function.

In some embodiments, the subject to be treated suffers from corneal neuropathy or corneal neuralgia. Corneal neuropathy or corneal neuralgia is a disorder associated with corneal pain caused by the damaged nerve fibers in the cornea, the sensory fibers. One of the examples of corneal neuropathy is a LASIK induced corneal neuropathy. Corneal neuropathy generally could be identified and diagnosed through dry eye investigations. Though the causes and risk factors are unclear yet, patients with dry eye-like symptoms, increased corneal sensitivity and changes of corneal nerve morphology, but no signs of dryness may suffer from corneal neuropathy.

In some embodiments, the subject to be treated suffers from ocular surface disease or disorder. The term "ocular surface diseases" or "ocular surface disorders" encompasses disease entities as well as related symptoms that result from a variety of abnormalities, including abnormal lid anatomy or function, abnormal or altered tear production or composition, and related subclinical signs. Many diseases can cause ocular surface disorders. Patients with ocular surface disorders may exhibit clinical signs common to several diseases, and include chronic punctate keratopathy, filamentary keratopathy, recurrent corneal erosion, bacterial conjunctivitis, culture-negative conjunctivitis, cicatrising (scarring) conjunctivitis, persistent epithelial defect, infectious keratitis, corneal melt and ocular surface failure. The most common ocular surface disorders stem from tear-film abnormalities and/or lid-gland dysfuntion ("blepharitis").

In some embodiments, the subject to be treated suffers from neurotrophic keratitis or neurotrophic keratopathy. Neurotrophic keratitis or neurootrophic keratopathy (NK) is a corneal degenerative disease characterized by a reduction or absence of corneal sensitivity. In NK, corneal innervation by trigeminal nerve is impaired. Since corneal sensory innervation is impaired in NK, patients do not commonly complain of ocular surface symptoms. However, blurred vision can be reported due to irregular epithelium or epithelial defects (PED), scarring, or edema. NK is usually graded in three different stages in accordance to the "Mackie classification". Stage II NK is defined by a recurrent or persistent epithelial defects, most commonly in the superior half of the cornea. One of the treatments that may be used in Stage II NK includes topical Nerve Growth Factor. Patients typically experience pain during treatment with NGF due to reforming of the nerves.

In some embodiments, the subject to be treated suffers from blepharitis. Blepharitis is an inflammatory condition of the eyelid margin, which can lead to permanent alterations in the eyelid margin or vision loss from superficial keratopathy, corneal neovascularization, and ulceration. According to anatomic location, blepharitis can be divided into anterior and posterior. Anterior blepharitis affects the eyelid skin, base of the eyelashes, and the eyelash follicles and includes the traditional classifications of staphylococcal and seborrheic blepharitis. Posterior blepharitis affects the meibomian glands and gland orifices, the primary cause being meibomian gland dysfunction. Symptoms of chronic blepharitis may include redness, burning sensation, irritation, tearing, eyelid crusting and sticking, and visual problems such as photophobia and blurred vision. Long-term management of symptoms may include daily eyelid cleansing routines and the use of therapeutic agents that reduce infection and inflammation. Treatment includes topical or systemic antibiotics e.g., bacitracin or erythromycin; oral antibiotics, e.g., tetracyclines (tetracycline, doxycycline, minocycline) or macrolides (erythromycin, azithromycin); topical steroids, e.g., corticosteroid, e.g., loteprednol etabonate, fluorometholone; topical combinations of an antibiotic and corticosteroid such as tobramycin/dexamethasone or tobramycin/loteprednol; topical cyclosporine 0.05%.

In some embodiments, the subject to be treated suffers from Meibomian gland dysfunction. The meibomian gland is a holocrine type of exocrine gland, at the rim of the eyelid inside the tarsal plate, responsible for the supply of meibum, an oily substance that prevents evaporation of the eye's tear film. Meibomian gland dysfunction (MGD), also known as meibomitis, posterior blepharitis or inflammation of the meibomian glands, is a chronic, diffuse abnormality of the meibomian glands, commonly characterized by terminal duct obstruction and/or qualitative/quantitative changes in the glandular secretion (Nelson J D, et al., *Invest Ophthalmol Vis Sci* 2011; 52:1930-7). It may result in alteration of the tear film, symptoms of eye irritation, clinically apparent inflammation, and ocular surface disease. MGD often causes dry eye, and may contribute to blepharitis. In some cases topical steroids and topical/oral antibiotics are also prescribed reduce inflammation. Intense pulsed light (IPL) treatments or other mechanical treatments that apply heat and pressure to express the glands (eg, LipiFlow) have also been shown to reduce inflammation and improve the gland function in patients.

In some embodiments, the subject to be treated suffers from graft-versus-host disease. Graft-versus-host disease (GVHD) is an inflammatory disease that is unique to allogeneic transplantation. It is an attack by transplanted leukocytes against the recipient's tissues that can occur even if the donor and recipient are HLA-identical. Acute graft-versus-host disease typically occurs in the first 3 months after transplantation and may involve the skin, intestine, or the liver. Corticosteroids such as prednisone are a standard treatment. Chronic graft-versus-host disease may also develop after allogeneic transplant and is the major source of late complications. In addition to inflammation, chronic graft-versus-host disease may lead to the development of fibrosis, or scar tissue, similar to scleroderma or other autoimmune diseases and may cause functional disability, and the need for prolonged immunosuppressive therapy.

In some embodiments, the subject to be treated suffers from ocular graft versus host disease. GVHD occurs in patients who have undergone allogenic hematological stem cell transplantation. It can occur in patients who have acute or chronic GVHD, though it is more common in patients with the chronic form. Approximately 40-90% of patients with chronic GVHD will develop ocular symptoms. Ocular manifestations can include moderate to severe keratoconjuncitvitis sicca, bilateral marginal keratitis, anterior uveitis, corneal ulceration or neovascularization. Treatment includes topical lubricants including preservative free artificial tears, autologous serum tears and other topical and systemic immunosuppressive treatments; systemic steroids; topical cyclosporine 0.5%.

EXAMPLES

The following examples are included to demonstrate non-limiting embodiments of the present invention.

General Test Conditions

The following procedures were employed under each test condition.

Equilibration with Solvent at 25° C.

For equilibration at 25° C., about 50 mg of compound I was equilibrated with 1 ml solvent for 24 h in a water bath at 25° C.±0.1. The solutions were filtered and dried for 10 minutes in the air. The solid part was investigated by XRPD (X-ray powder diffraction). If differences were observed additional investigations were performed as appropriate (e.g. DSC, TG, IR, SEM).

Equilibration with Solvent at 50° C.

For equilibration with solvent at 50° C., about 50 mg of compound I was equilibrated with 1 ml solvent for 24 h in a water bath at 50° C.±0.1. The filtrate was used as noted in the particular example.

Crystallization from Hot Saturated Solutions

In order to crystallize compound I from hot saturated solutions, approximately 300 mg of drug substance was dissolved in the minimal amount of solvent at 60° C. and hot filtrated. No remaining crystals were visible. The solutions were put in an ice bath and agitated. The precipitates were collected on a filter, dried and investigated as described as noted. The temperature may be changed as noted in the specific examples.

Precipitation by Addition of Solvent

For precipitation of compound I by addition of solvent, compound I was dissolved in a solvent where the solubility is high, and a solvent in which compound I is highly insoluble was added. The precipitate was treated as described in the specific examples.

X-Ray Diffraction

The X-ray powder diffraction (XRPD) patterns described herein were recorded on a Bruker® D8 Advance diffractometer using $CuK_{\alpha}$ radiation. The XRPD pattern was recorded between 2° and 40° (2-theta).

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and wavelength of X-ray radiation used. The agreement in the 2-theta-diffraction angles between specimen and reference is within 0.2° for the same crystal form and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

Thermogravimetric Method

The TGA instruments used to test the crystalline forms was a Mettler Toledo® TGA851e TGA850. Samples of 10 to 20 milligrams were analyzed at a heating rate of 20° C. per minute in the temperature range between 30° C. and about 300° C.

Differential Scanning Calorimetry (DSC)

The DSC instrument used to test the crystalline forms was a Mettler Toledo® DSC822e or a Perkin Elmer® DSC7. The DSC cell/sample chamber was purged with 20-50 ml/min of ultra-high purity nitrogen gas. The instrument was calibrated with high purity indium. The sample was placed into an open aluminum DSC pan and measured against an empty reference pan. About 1-3 mg of sample powder was placed into the bottom of the pan and lightly tapped down to make contact with the pan. The weight of the sample was measured accurately and recorded to a hundredth of a milligram. The instrument was programmed to heat at 10° C. per minute in the temperature range between 30° C. and 300° C.

Example 1. Preparation of Crystal Form A

Crystal form A was obtained by converting the hydrochloride salt of compound I to free base. The final crystallization was done by cooling from hot methanol to 0° C., where the compound crystallized as crystal form A.

Figure 2:
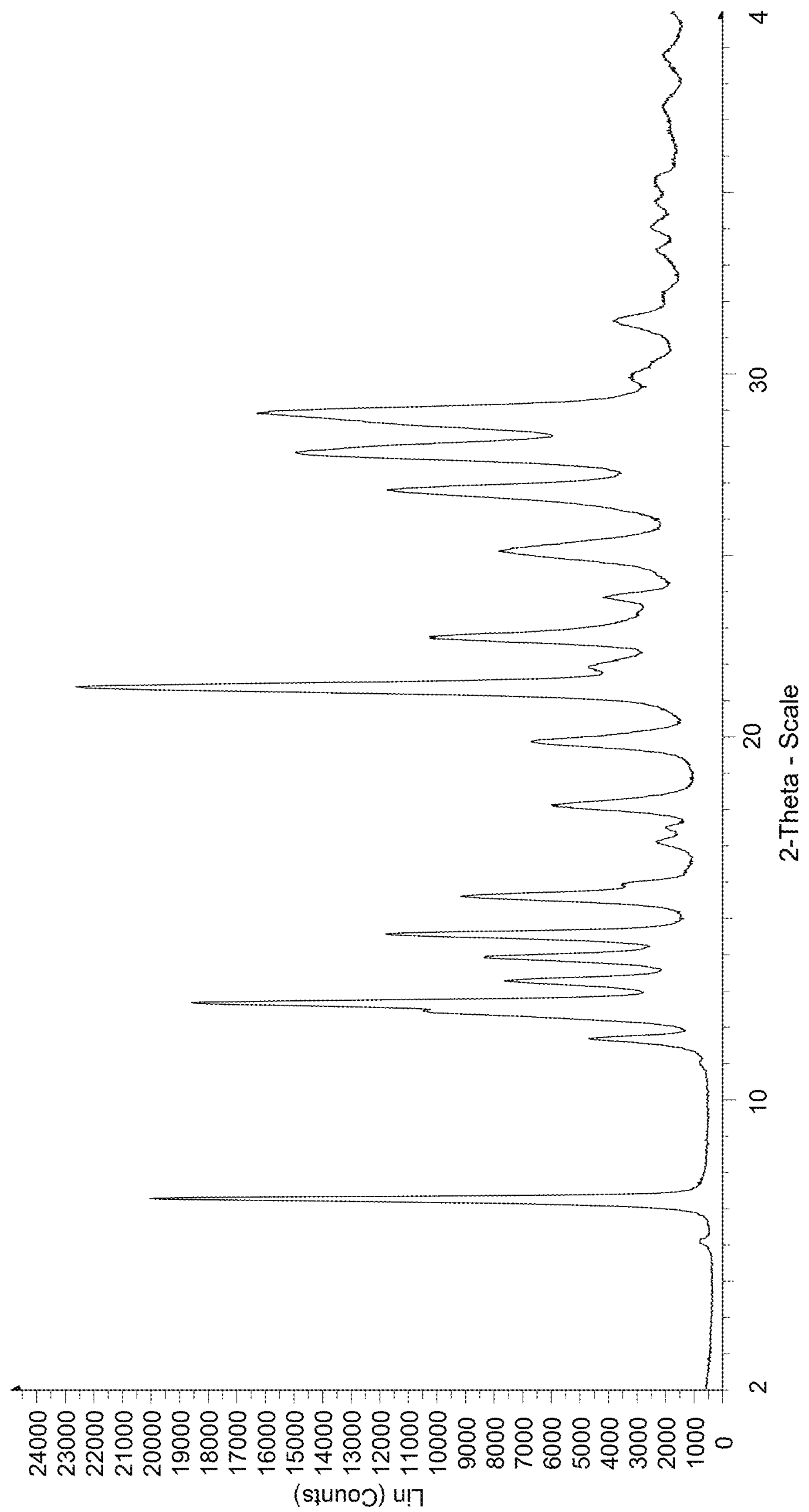
FIG. 2 provides the X-ray powder diffraction pattern of crystal form A of compound I.

The differential scanning calorimetry curve of crystal form A showed a small endothermic event at about 264° C. followed by melting at about 269° C. FIG. 1 shows the superposition of the simulated and actual X-ray diffraction patterns of crystal form A. The X-ray powder diffraction pattern of crystal form A is shown in FIG. 2 and the peak listing is as shown in Table 1. The single crystal data for crystal form A of compound I is as follows:

| | |
|---|---|
| Molecular formula: | $C_{18}H_{15}N_3O_2$ |
| Molecular weight (free acid): | 305.34 |
| Lattice parameters: | |
| Space symmetry | monoclinic |
| Spacegroup | P21/n |
| Cell Volume (Å$^3$) | 3157.2 |
| Crystal Density (g/cm$^3$) | 1.285 |
| a (Å) | 16.285 |
| b (Å) | 7.977 |
| c (Å) | 24.640 |
| beta (°) | 99.046 |
| z | 8 |

TABLE 1

Powder X-Ray Diffraction Peaks compound I Crystal form A

| ° deg 2 θ | d-space | Relative intensity (%) |
|---|---|---|
| 7.23 | 12.211 | 89 |
| 12.65 | 6.994 | 82 |
| 13.26 | 6.673 | 34 |
| 13.91 | 6.362 | 37 |
| 14.54 | 6.087 | 52 |
| 15.59 | 5.679 | 40 |
| 18.11 | 4.896 | 26 |
| 19.86 | 4.466 | 30 |
| 21.37 | 4.155 | 100 |
| 22.75 | 3.906 | 45 |
| 25.13 | 3.540 | 35 |
| 26.81 | 3.323 | 52 |

TABLE 1-continued

| Powder X-Ray Diffraction Peaks compound I Crystal form A | | |
|---|---|---|
| ° deg 2 θ | d-space | Relative intensity (%) |
| 27.84 | 3.202 | 66 |
| 28.95 | 3.082 | 72 |

Example 2. Preparation of Crystal Form C

Crystal form C was obtained by heating crystal form A in thermogravimetric analyzer to about 250° C. or by heating crystal form B for 80 minutes at 250° C. In a 1:1 mixture with crystal form B, crystal form C converted in isopropanol to crystal form B. In a 1:1 mixture with crystal form A, crystal form C converted in methanol to Solvate $S_B$ (crystal form G).

Figure 3:
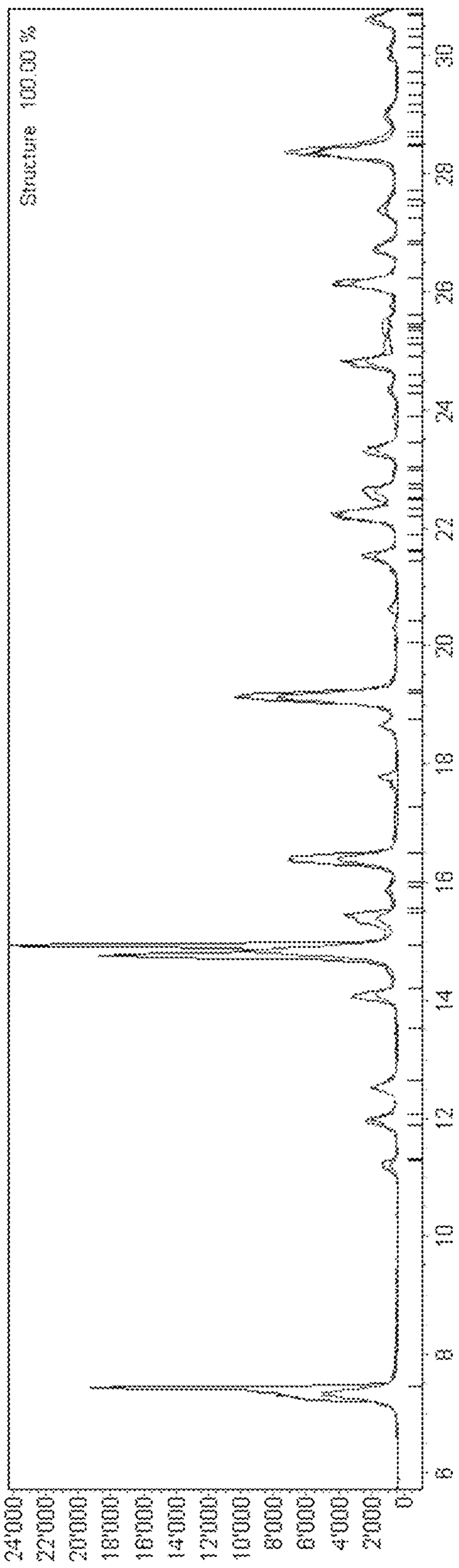
FIG. 3 provides a superposition of experimental and calculated XRPD patterns of crystal form C of compound I.
Figure 4:
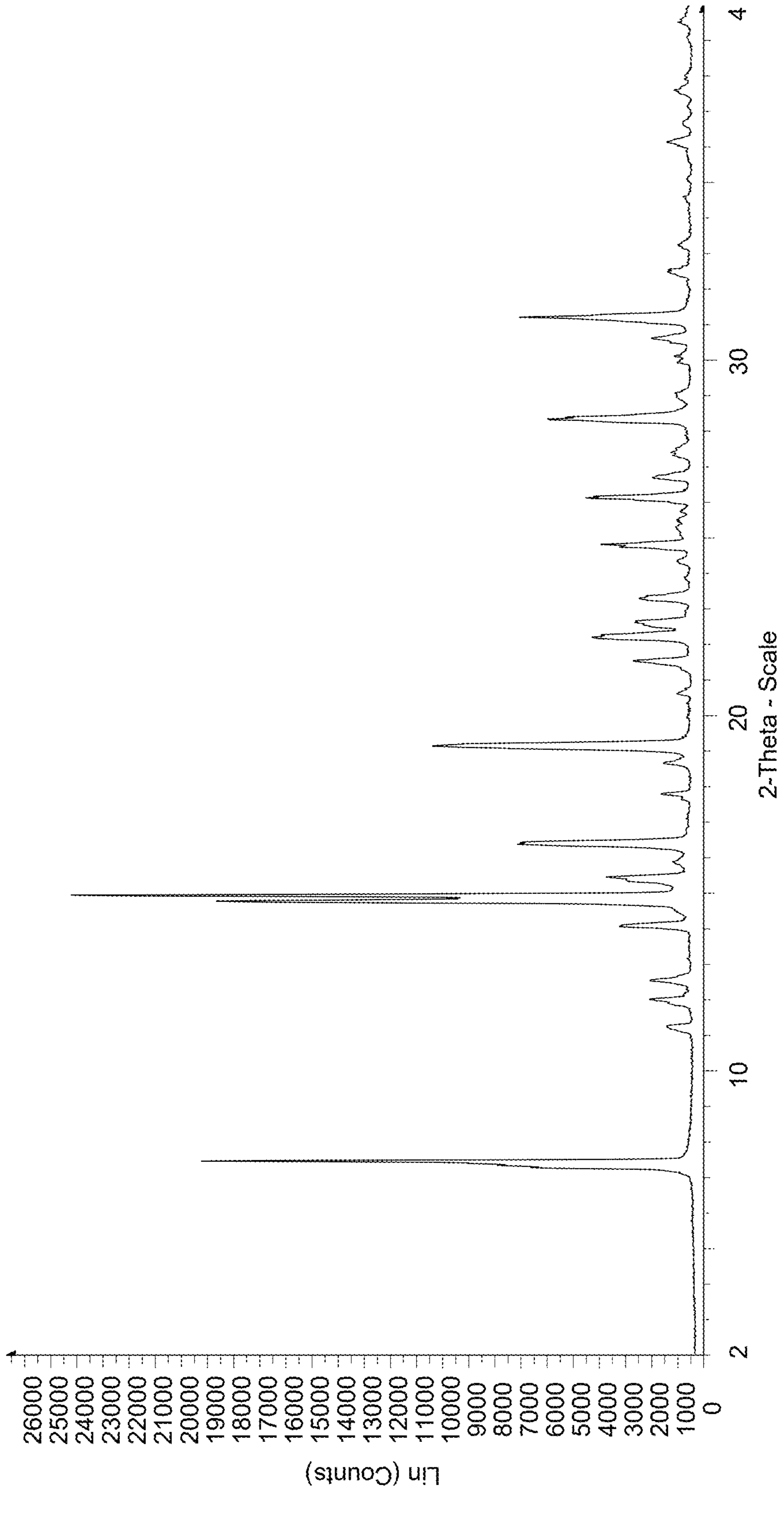
FIG. 4 provides the X-ray powder diffraction pattern of crystal form C of compound I.

FIG. 3 shows the superposition of the simulated and actual X-ray diffraction patterns of crystal form C. The X-ray powder diffraction pattern of crystal form C is shown in FIG. 4 and the peak listing is as shown in Table 2. The lattice parameters for crystal form C is as follows:

| | |
|---|---|
| Space symmetry | orthorhombic |
| Spacegroup | Pna21 |
| Cell Volume (Å$^3$) | 3078.3 |
| Crystal Density (g/cm$^3$) | 1.318 |
| a (Å) | 15.685 |
| b (Å) | 8.281 |
| c (Å) | 23.697 |
| z | 8 |

TABLE 2

| Powder X-Ray Diffraction Peaks Crystal form C | | |
|---|---|---|
| ° deg 2 θ | d-space | Relative intensity (%) |
| 7.42 | 11.912 | 79 |
| 14.07 | 6.290 | 13 |
| 14.91 | 5.937 | 100 |
| 16.38 | 5.406 | 29 |
| 19.14 | 4.634 | 43 |
| 24.80 | 3.588 | 16 |
| 26.14 | 3.406 | 18 |
| 28.36 | 3.144 | 25 |
| 31.22 | 2.862 | 29 |

Example 3. Preparation of Crystal Form E

Approximately 1000 mg of compound I in polymorphic form B was equilibrated in 20 ml of a mixture acetone/water (1:1) for 1 week at 25° C. and then filtrated. XRPD analysis of the recovered solid showed the pattern of Modification $H_A$ (hydrate form). Approximately 1000 mg of the hydrate $H_A$ was heated in an oven at 260° C. for about 16 minutes to obtain crystal form E.

TABLE 3

| Equilibration of solvents at 25° C. of Crystal form E | | |
|---|---|---|
| Solvent | XRDP | Comments |
| Acetone | // | too soluble |
| Ethanol abs. | – | |
| Ethyl acetate | – | |

TABLE 3-continued

| Equilibration of solvents at 25° C. of Crystal form E | | |
|---|---|---|
| Solvent | XRDP | Comments |
| Water | – | |
| Cyclohexane | – | |
| t-butylmethylether | + | amorphous |

Explanation
"–": no change detected
"+": change detected
"//": not carried out because substance too soluble in the solvent

TABLE 4

| Equilibration with solvents at 25 degree C. of Crystal form E mixed with Crystal form B | | |
|---|---|---|
| Solvent | XRDP | Comments |
| Acetone/water | + | mix form B, form E and form $H_A$ |
| Ethanol abs. | + | crystal form B |
| Ethyl acetate | + | practically amorphous |
| Water | – | |
| Cyclohexane | – | |

Explanation
"–": no change detected
"+": change detected
"//": not carried out because substance too soluble in the solvent Crystal form E was found to be non-hygroscopic. The maximum water uptake is less than 0.1% at 25° C. up to 92% relative humidity.

Crystal form E demonstrated a melting onset temperature of about 281° C., as measured by DSC. As seen in Table 4, crystal form E converts into crystal form B when equilibrated in ethanol. Solubility of crystal form E was measured at 25° C. Analysis was done by HPLC and the results are shown in Table 5.

TABLE 5

| Solubility and dissolution rate parameters of Crystal form E at 25° C. and 37° C. | | |
|---|---|---|
| Parameter | Buffer | Crystal form E |
| Solubility at 25° C. | pH 1 (0.1N HCl) | 0.345 mg/ml |
| | pH 4.5 (acetate) | 0.010 mg/ml |
| | pH 6.88 (phosphate) | 0.011 mg/ml |
| Intrinsic dissolution | HCl 0.1 N | 0.0194 mg min$^{-1}$ cm$^{-2}$ |
| rate (IDR) at 37° C. | pH 3 | 0.0025 mg min$^{-1}$ cm$^{-2}$ |

Figure 5:
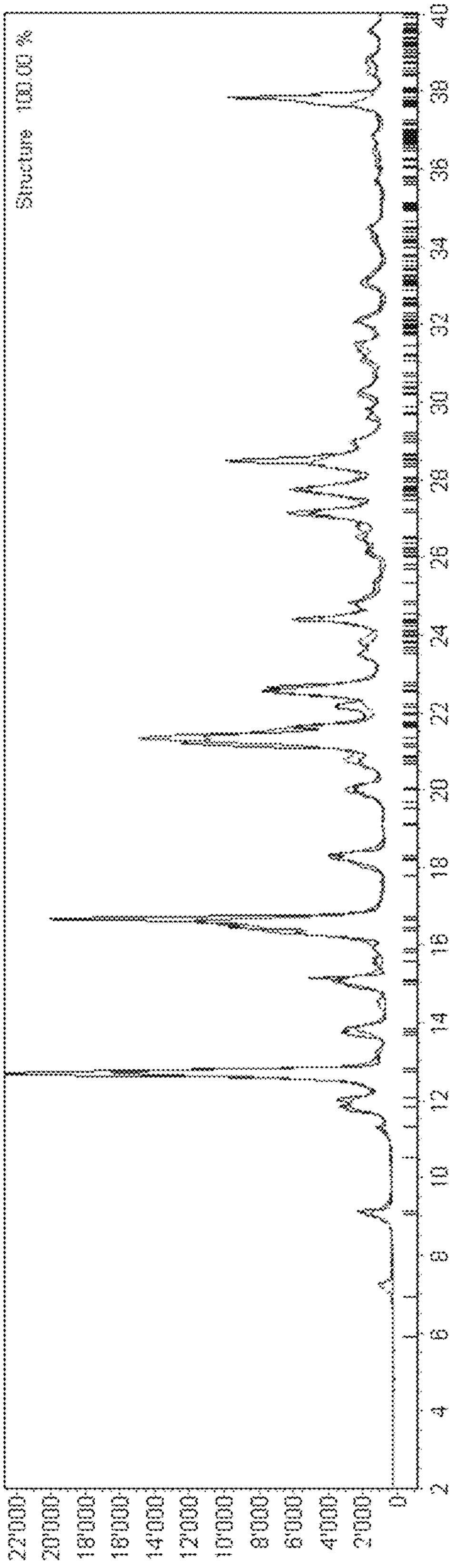
FIG. 5 provides a superposition of experimental and calculated XRPD patterns of crystal form E of compound I.
Figure 6:
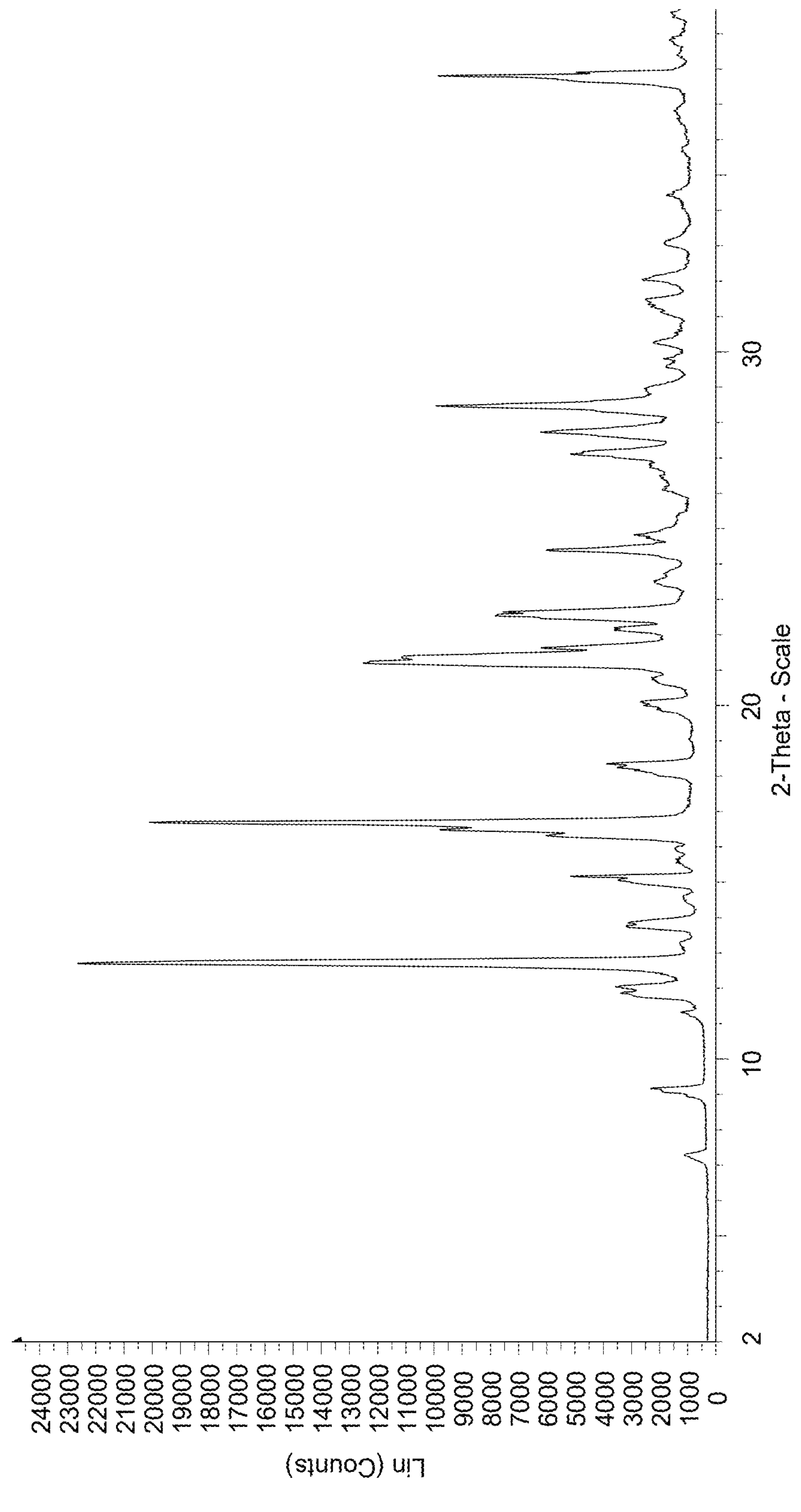
FIG. 6 provides the X-ray powder diffraction pattern of crystal form E of compound I.

FIG. 5 shows the superposition of the simulated and actual X-ray diffraction patterns of crystal form E. The X-ray powder diffraction pattern of crystal form E is shown in FIG. 6 and the peak listing is as shown in Table 6. The lattice parameters for crystal form E is as follows:

| | |
|---|---|
| Space symmetry | triclinic |
| Spacegroup | P-1 |
| Cell Volume (Å$^3$) | 1637.8 |
| Crystal Density (g/cm$^3$) | 1.238 |
| a (Å) | 8.592 |
| b (Å) | 13.046 |
| c (Å) | 14.935 |
| α (Å) | 90.34 |
| β (Å) | 90.23 |
| γ (Å) | 78.03 |
| z | 4 |

TABLE 6

| Powder X-Ray Diffraction Peaks Crystal form E of compound I | | |
|---|---|---|
| ° deg 2 θ | d-space | Relative intensity (%) |
| 9.09 | 9.724 | 8 |
| 11.93 | 7.414 | 13 |
| 12.69 | 6.969 | 100 |
| 13.80 | 6.413 | 13 |
| 15.09 | 5.869 | 15 |
| 16.65 | 5.321 | 87 |
| 18.28 | 4.850 | 15 |
| 21.27 | 4.174 | 54 |
| 22.58 | 3.935 | 34 |
| 24.42 | 3.642 | 27 |
| 27.14 | 3.283 | 23 |
| 27.74 | 3.213 | 27 |
| 28.50 | 3.130 | 44 |
| 37.82 | 2.377 | 43 |

Example 4. Preparation of Crystal Form F (Hydrate $H_A$)

Hydrate $H_A$ (crystal form F) was obtained by equilibration of a slurry of crystal form A or crystal form B in acetone/water (1:1) at 25° C. The DSC curve shows a broad endotherm at about 89° C. due to evaporation of water, followed by several endothermic transitions above 264° C. Single crystal analysis confirmed the presence of one mole of water in the crystal structure (calculated water content is 5.6%).

Figure 7:
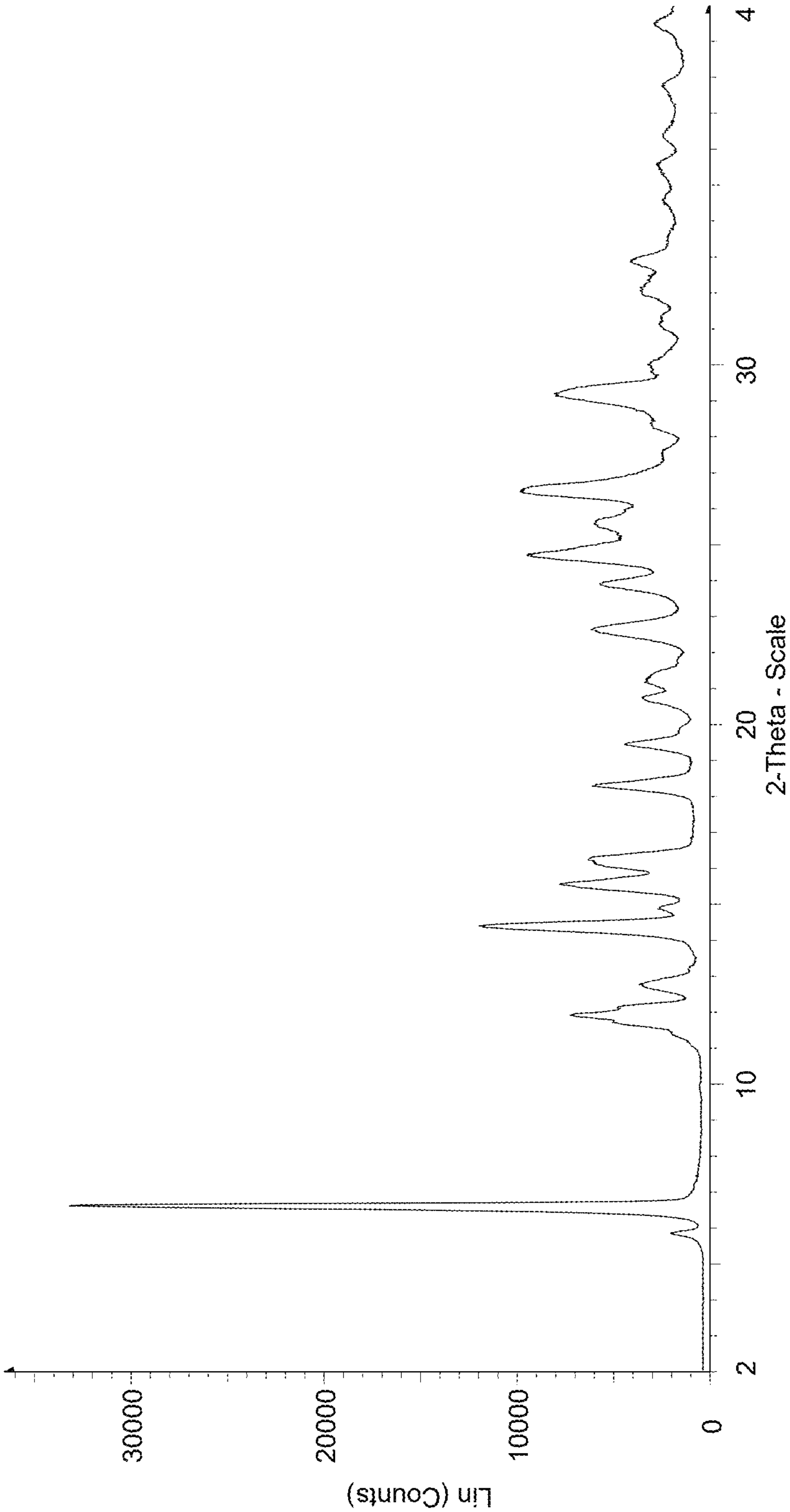
FIG. 7 provides the X-ray powder diffraction pattern of Crystal form F (Hydrate $H_A$) of compound I.

The X-ray powder diffraction pattern of crystal form F is shown in FIG. 7 and the peak listing is as shown in Table 7.

TABLE 7

| Powder X-Ray Diffraction Peaks Crystal form F (Hydrate $H_A$) | | |
|---|---|---|
| ° deg 2 θ | d-space | Relative intensity (%) |
| 6.58 | 13.417 | 100 |
| 11.90 | 7.432 | 22 |
| 12.75 | 6.938 | 11 |
| 14.38 | 6.153 | 36 |
| 15.55 | 5.694 | 23 |
| 16.25 | 5.450 | 19 |
| 18.30 | 4.843 | 18 |
| 19.46 | 4.558 | 13 |
| 22.66 | 3.922 | 18 |
| 23.92 | 3.717 | 17 |
| 24.73 | 3.598 | 28 |
| 25.63 | 3.472 | 18 |
| 26.52 | 3.358 | 30 |
| 29.21 | 3.055 | 24 |

Example 5. Preparation of Crystal Form G (Methanol Solvate $S_B$) of Compound I Methanol solvate $S_B$ (crystal form G) of compound I was obtained by equilibration of a slurry of crystal form A in methanol at 25° C. Single crystal structure analysis which was performed at 100K showed the presence of one mole of methanol. The solvents evaporates easily as TGA analysis of the samples showed only small amounts of residual solvents of up to 0.2% (calculated methanol content is 9.5% for a mono-solvate).

Figure 8:
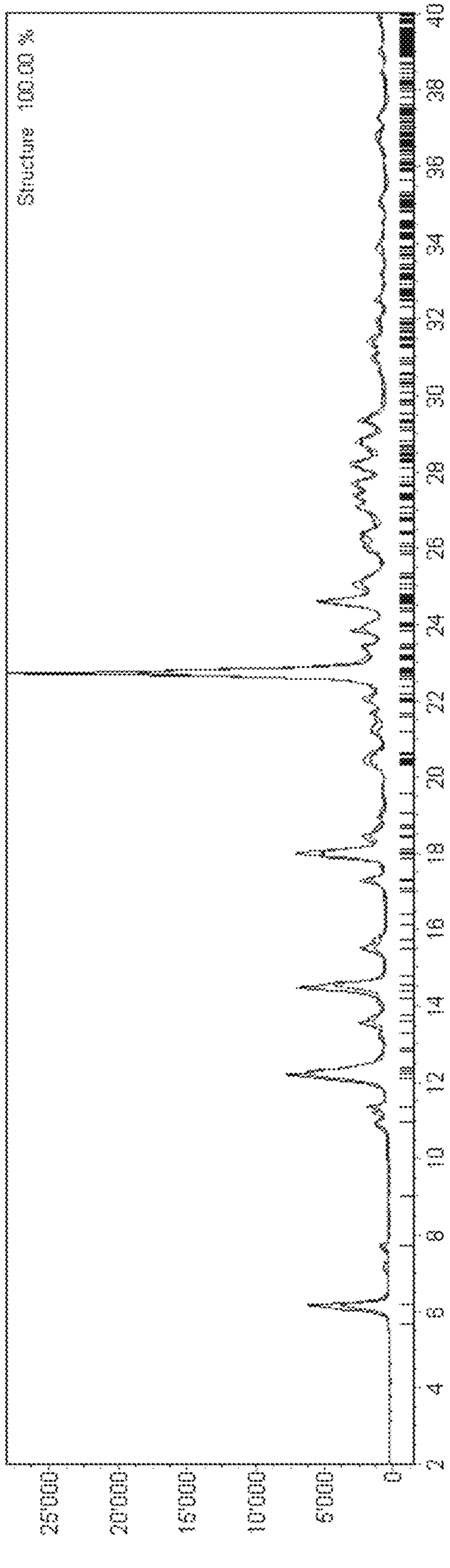
FIG. 8 provides a superposition of experimental and calculated XRPD patterns of crystal form G (methanol solvate $S_B$) of compound I.
Figure 9:
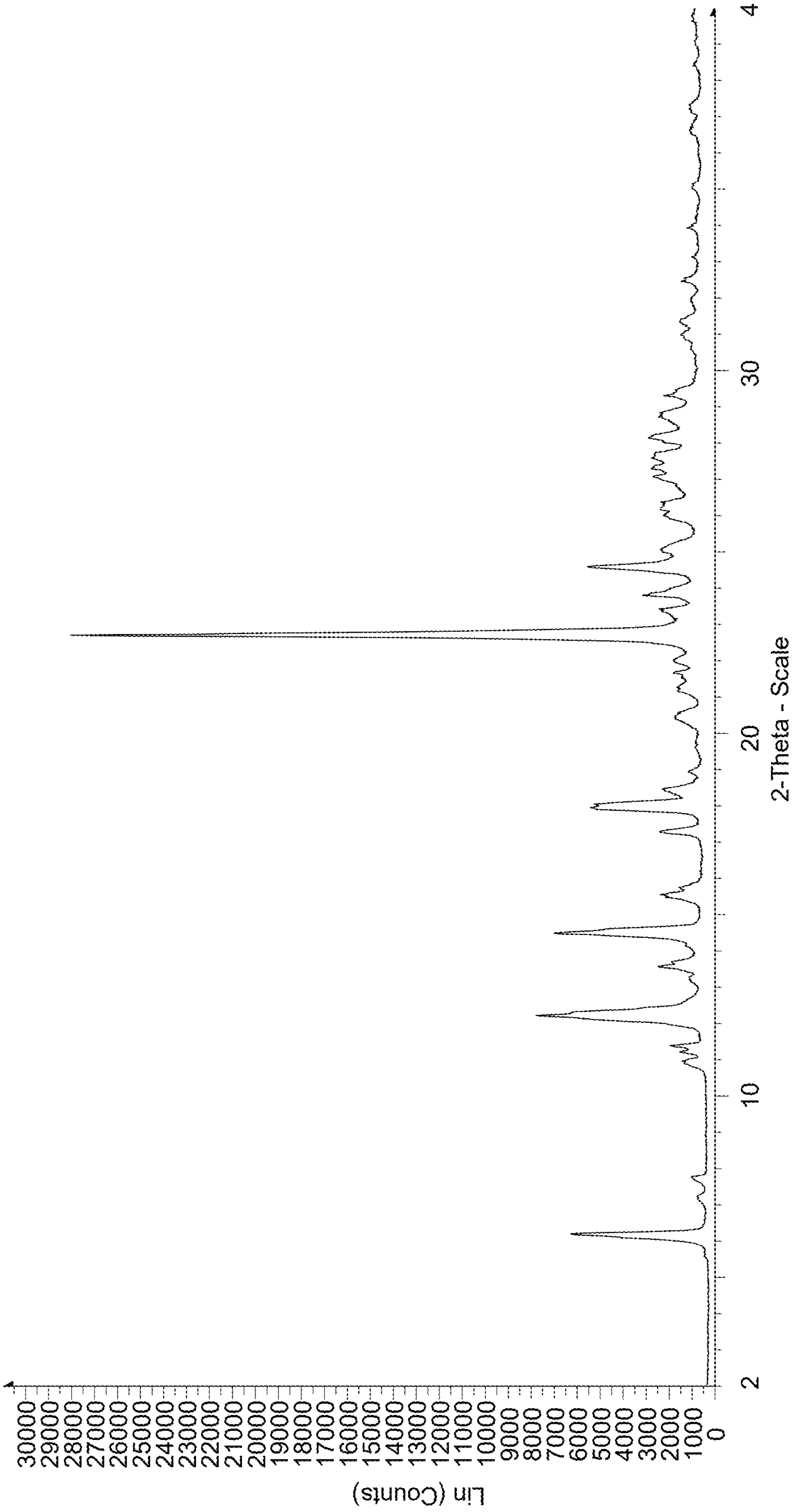
FIG. 9 provides the X-ray powder diffraction pattern of crystal form G (methanol solvate $S_B$) of compound I.

FIG. 8 shows the superposition of the simulated and actual X-ray diffraction patterns of crystal form G. The X-ray powder diffraction pattern of crystal form G is shown in FIG. 9 and the peak listing is as shown in Table 8. The lattice parameters for crystal form G is as follows:

| | |
|---|---|
| Space symmetry | triclinic |
| Spacegroup | P-1 |
| Cell Volume (Å$^3$) | 1849.3 |
| Crystal Density (g/cm$^3$) | 1.212 |
| a (Å) | 8.242 |
| b (Å) | 14.478 |
| c (Å) | 16.064 |
| α (°) | 80.49 |
| β (°) | 78.33 |
| γ (°) | 85.18 |
| z | 4 |

TABLE 8

| Powder X-Ray Diffraction Peaks methanol solvate $S_B$ (Crystal form G) | | |
|---|---|---|
| Angle 2-Theta ° | d value Angstrom | Intensity % % |
| 6.14 | 14.378 | 22 |
| 12.22 | 7.239 | 28 |
| 14.50 | 6.106 | 25 |
| 17.98 | 4.931 | 19 |
| 22.72 | 3.910 | 100 |
| 24.61 | 3.615 | 20 |

Example 6. Preparation of Crystal Form J (Acetonitrile Solvate $S_A$) of Compound I Acetonitrile solvate $S_A$ (crystal form J) of compound I was obtained by equilibration a slurry of crystal form A in acetonitrile at 25° C. Single crystal analysis showed the presence of one mole of acetonitrile in the crystal structure (calculated acetonitrile content is 11.9%).

Figure 10:
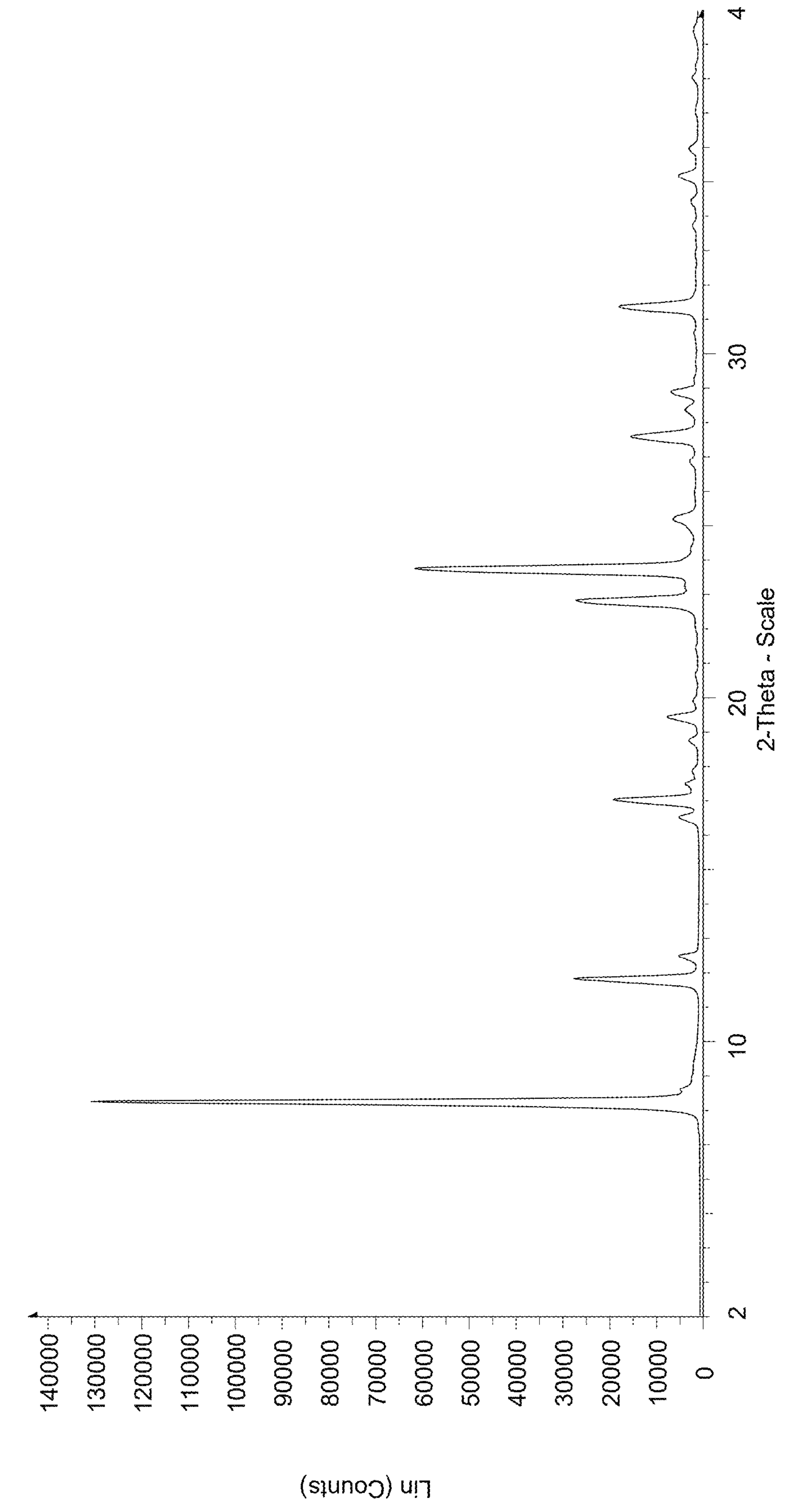
FIG. 10 provides the X-ray powder diffraction pattern of crystal form J (acetonitrile solvate $S_A$) of compound I.

The X-ray powder diffraction pattern of crystal form J is shown in FIG. 10 and the peak listing is as shown in Table 9. The lattice parameters for crystal form J is as follows:

| Space symmetry | monoclinic |
|---|---|
| Spacegroup | P21/n |
| Cell Volume(Å3) | 1833.5 |
| Crystal Density (g/cm$^3$) | 1.255 |
| a (Å) | 15.545 |
| b (Å) | 5.770 |
| c (Å) | 21.348 |
| beta (°) | 106.75 |
| z | 4 |

TABLE 9

| Powder X-Ray Diffraction Peaks acetonitrile solvate $S_A$ (Crystal form J) of compound I | | |
|---|---|---|
| ° deg 2 θ | d-space | Relative intensity (%) |
| 8.20 | 10.773 | 100 |
| 11.79 | 7.502 | 21 |
| 17.01 | 5.208 | 15 |
| 22.81 | 3.896 | 21 |
| 23.75 | 3.743 | 48 |
| 27.61 | 3.228 | 12 |
| 31.40 | 2.847 | 14 |

Example 7. Preparation of Crystal Form K

Figure 11:
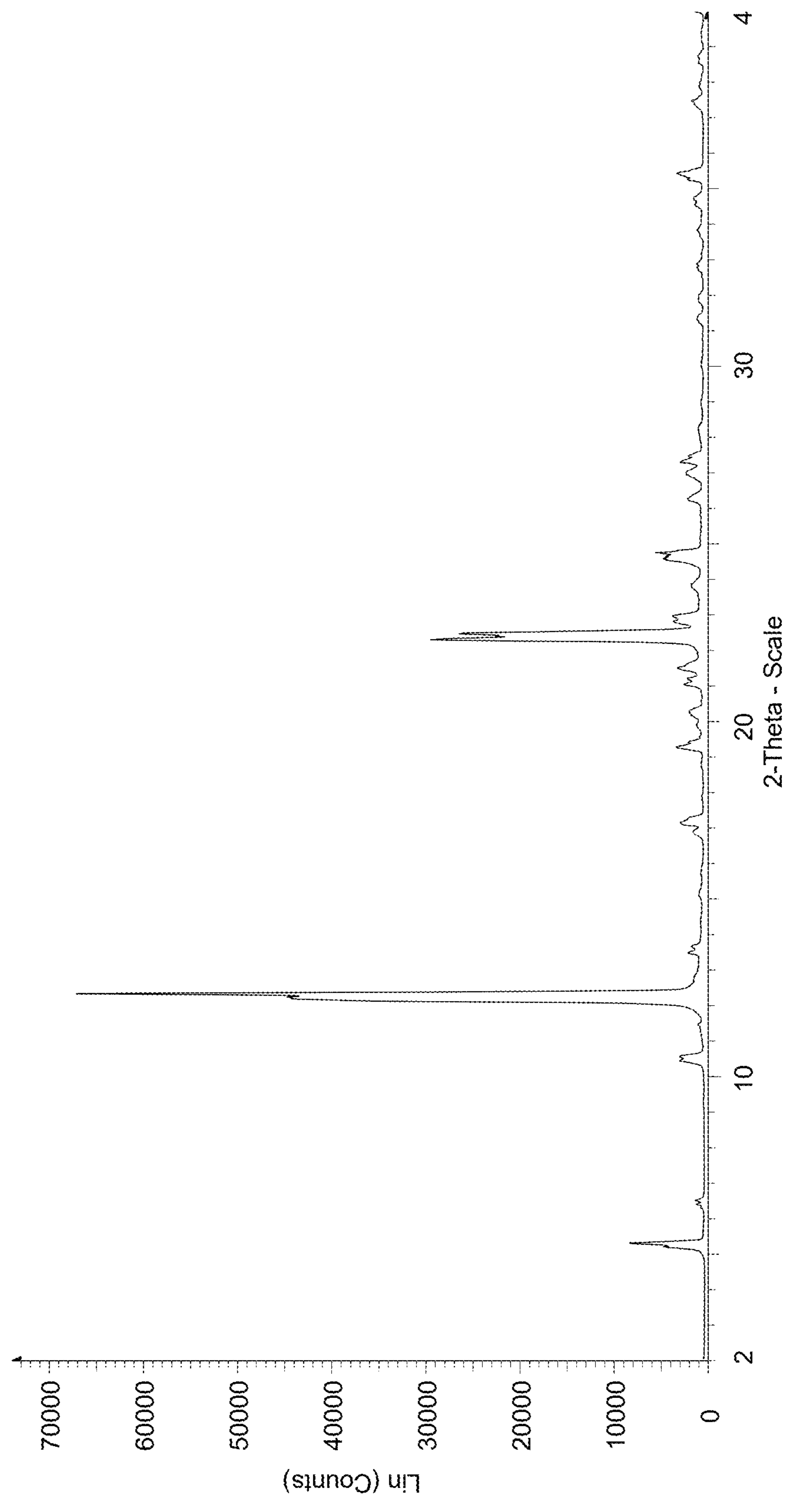
FIG. 11 provides the X-ray powder diffraction pattern of crystal form K of compound I.

Crystal form K was obtained by evaporation crystallization of compound I in acetone at 25° C. Specifically, crystal form A was dissolved in sufficient acetone at room temperature and the solvent was allowed to evaporate at ambient conditions to obtain crystal form K. The X-ray powder diffraction pattern of crystal form K is shown in FIG. 11 and the peak listing is as shown in Table 9.

TABLE 10

Powder X-Ray Diffraction Peaks crystal form K

| ° deg 2 θ | d-space | Relative intensity (%) |
|---|---|---|
| 5.25 | 16.812 | 14 |
| 6.45 | 13.690 | 2 |
| 10.50 | 8.422 | 5 |
| 12.28 | 7.199 | 100 |
| 17.15 | 5.167 | 5 |
| 19.27 | 4.602 | 6 |
| 22.44 | 3.960 | 43 |

Example 8. Preparation of Crystal Form L

About 60 mg of compound I as crystal form B were dissolved in 4 ml of acetone. Subsequently about 20 ml of hexane was added to the solution until crystallization of compound I occurred in the form of crystal form L. The suspension was filtrated and the isolated powder was characterized by X-powder diffraction. The DSC curve shows a broad endotherm at about 65° C. followed by further small endo- and exothermic event. This suggests that crystal form L is actually a solvated form.

Figure 12:
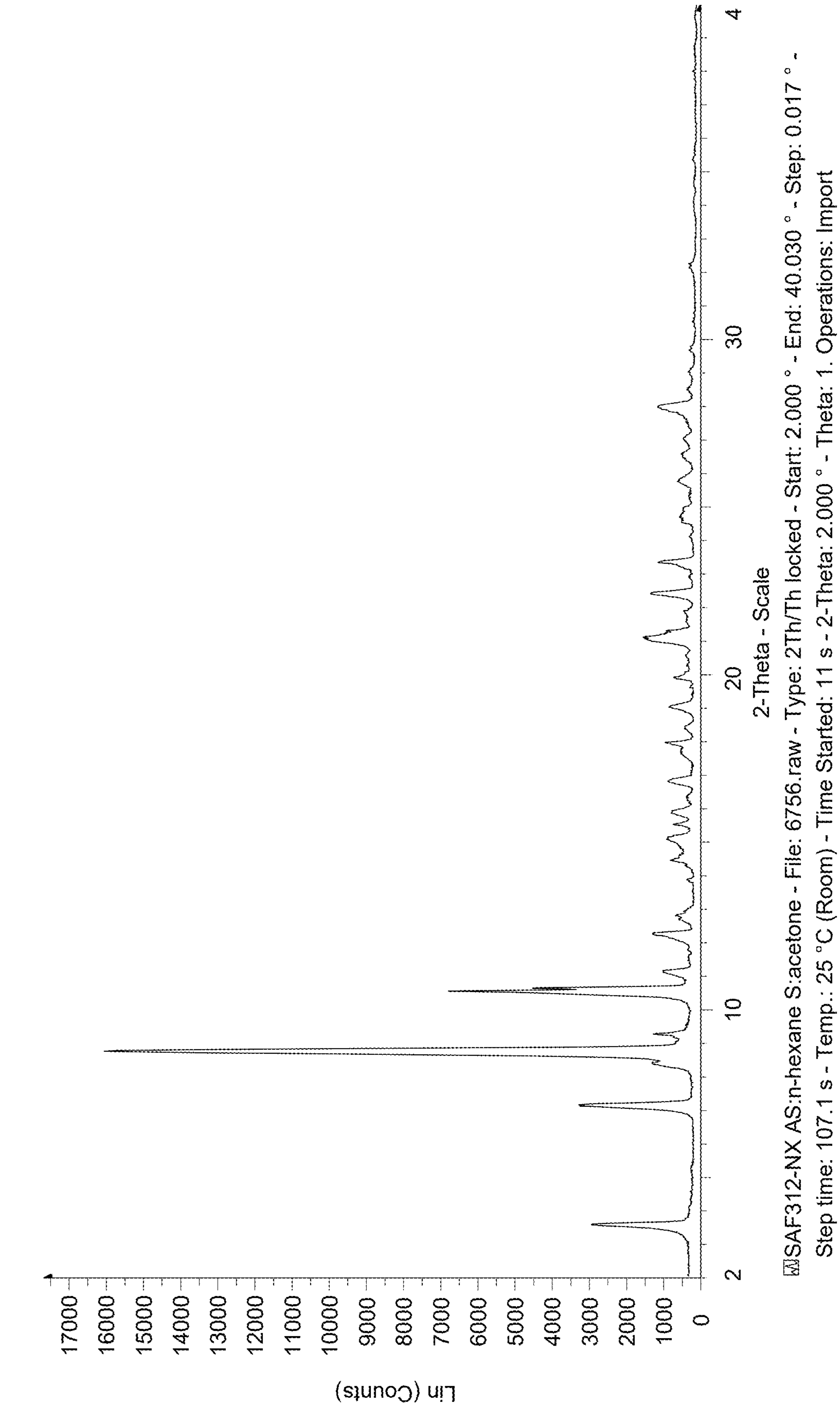
FIG. 12 provides the X-ray powder diffraction pattern of crystal form L of compound I.
Figure 13:
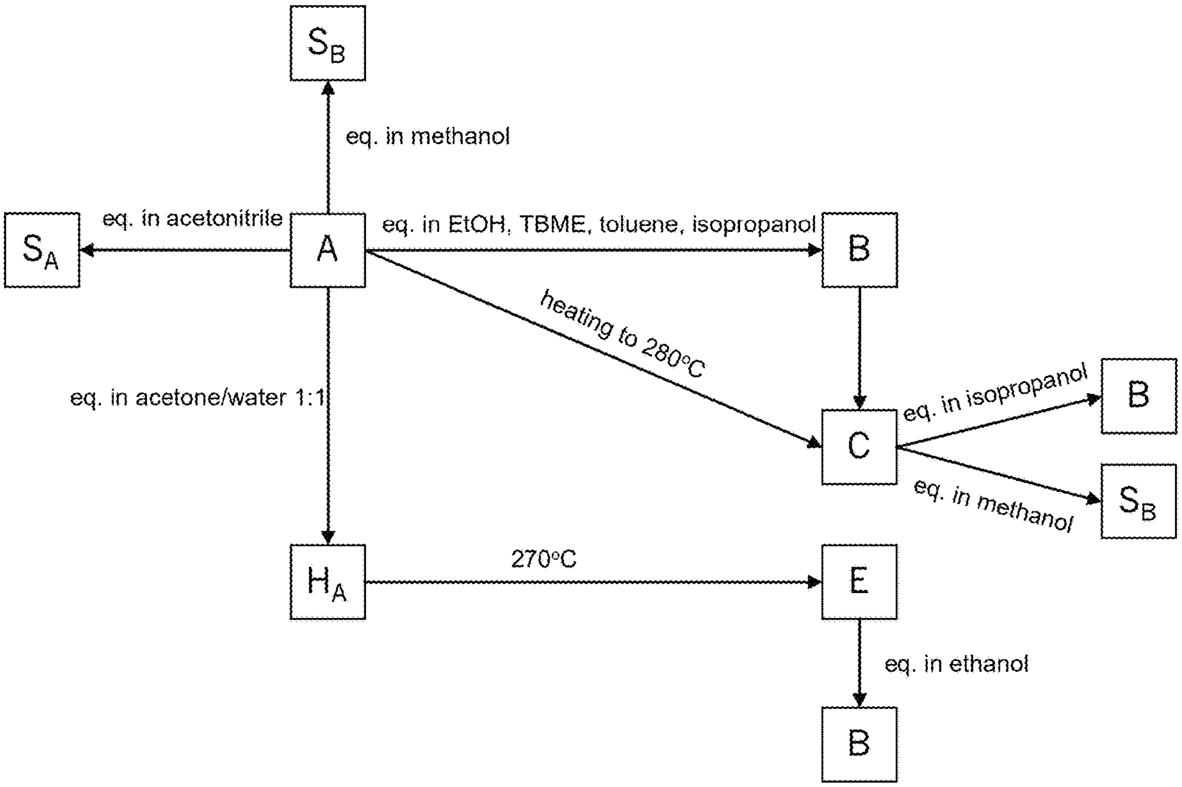
FIG. 13 demonstrates the relationship of polymorphic and solvated/hydrated forms of compound I free base and exemplary methods for their conversion.

The X-ray powder diffraction pattern of crystal form L is shown in FIG. 12 and the peak listing is as shown in Table 11.

TABLE 11

Powder X-Ray Diffraction Peaks of Crystal form L of compound I

| ° deg 2 θ | d-space | Relative intensity (%) |
|---|---|---|
| 3.54 | 24.939 | 18 |
| 7.12 | 12.413 | 20 |
| 8.74 | 10.111 | 100 |
| 10.55 | 8.381 | 42 |
| 11.11 | 7.956 | 6 |
| 12.23 | 7.229 | 8 |
| 19.06 | 4.653 | 5 |
| 21.09 | 4.210 | 9 |
| 22.44 | 3.959 | 8 |
| 23.37 | 3.803 | 7 |

Example 9. Solubility of Compound I

As noted above, compound I is sparingly soluble in various media. The solubility of compound I in various solvents is shown in Table 12.

TABLE 12

Solubility of compound I in Solvents

| Solvent | Solubility in |
|---|---|
| Water | 0.01 |
| Ethanol | 0.79 |

TABLE 12-continued

Solubility of compound I in Solvents

| Solvent | Solubility in |
|---|---|
| Polyethylene Glycol 200 | 1.62 |
| Polyethylene Glycol 300 | 2.04 |
| Polyethylene Glycol 400 | 1.66 |
| Propylene Glycol | 1.68 |
| Isosorbide | 0.34 |
| Propylene Carbonate | 0.40 |
| Hexylene Glycol | 0.28 |
| Isopropanol | 0.33 |
| Isopropyl Myrisate | 0.09 |
| Diisopropyl Adipate | 0.16 |
| Oleyl Alcohol | 0.12 |
| Mineral Oil | 0.03 |
| Medium-Chain Triglycerides (Miglyol 812) | 0.10 |

Example 10. Exploratory Formulations for Stability Testing

Based on the limited solubility of compound I in various solvents and in water, a suspension formulation was explored for development. The following five formulations were prepared and tested for stability. Formulations were stored in crimp-sealed glass vials at room temperature and at 40° C. At 6, 8 and 12 weeks, samples were evaluated for compound I stability.

TABLE 13

Compound I Formulations for Exploratory Stability

| | Percent w/w | | | | |
|---|---|---|---|---|---|
| Component | FID 121522 | FID 121511 | FID 121512 | FID 121513[a] | Lot 17307:087B |
| Compound I | 0.5 | 0.5 | 0.5 | 0.00135 | 0.5 |
| Tyloxapol | 0.1 | 0.1 | 0.1 | 0.1 | 0.1 |
| Poloxamer 407 | 17.5 | — | — | — | — |
| Hypromellose | — | 0.5 | 0.5 | — | — |
| Carbomer Homopolymer Type B | — | — | — | — | 0.4 |
| Polyethylene Glycol 6000 | 2 | — | — | — | — |
| Polyethylene Glycol 400 | — | — | 7 | 7 | — |
| Benzalkonium Chloride | 0.02 | 0.02 | 0.02 | 0.02 | 0.02 |
| Edetate Disodium | 0.02 | 0.02 | 0.02 | 0.02 | 0.02 |
| Boric Acid | 0.3 | 0.3 | 0.3 | 0.3 | 0.3 |
| Mannitol | 0.3 | 4.5 | 0.3 | 0.3 | 4.5 |
| Monobasic Sodium Phosphate monohydrate | 0.13 | 0.13 | 0.13 | 0.13 | 0.13 |
| Dibasic sodium phosphate anhydrous | 0.01 | 0.01 | 0.01 | 0.01 | 0.01 |
| Sodium Hydroxide | qs pH 6 | qs pH 6 | qs pH 6 | qs pH 6 | qs pH 6 |
| Hydrochloric Acid | qs pH 6 | qs pH 6 | qs pH 6 | qs pH 6 | qs pH 6 |
| Purified Water | qs 100 | qs 100 | qs 100 | qs 100 | qs 100 |

[a]FID 121513 is the filtered supernatant of FID 121512 and is a solution. The other four formulations in the table are suspensions.

The formulations prepared in Table 13 were assayed using an exploratory UPLC method developed for the assay of compound I as shown in Table 14.

TABLE 14

| Exploratory Compound I UPLC Method | | | | | |
|---|---|---|---|---|---|
| Column | ACQUITY ® UPLC BEH Shield RP18, 1.7 μm, 2.1 × 100 mm | | | | |
| Column temperature | 65° C. UV detector wavelength 254 nm | | | | |
| Injection volume | 2 μL | | | | |
| Mobile phase | A 0.1% Formic Acid B Acetonitrile | | | | |
| Gradient | Tim (min | Flow Rate (mL/min | % A | % B | Curve |
| | 0 | 0.8 | 70 | 30 | |
| | 1.0 | 0.8 | 30 | 70 | 6 |
| | 1.5 | 0.8 | 20 | 80 | 6 |
| | 2 | 0.8 | 70 | 30 | 6 |
| Run time | 3 | | | | |
| Relative retention | 0.9 | | | | |

Figure 14A:
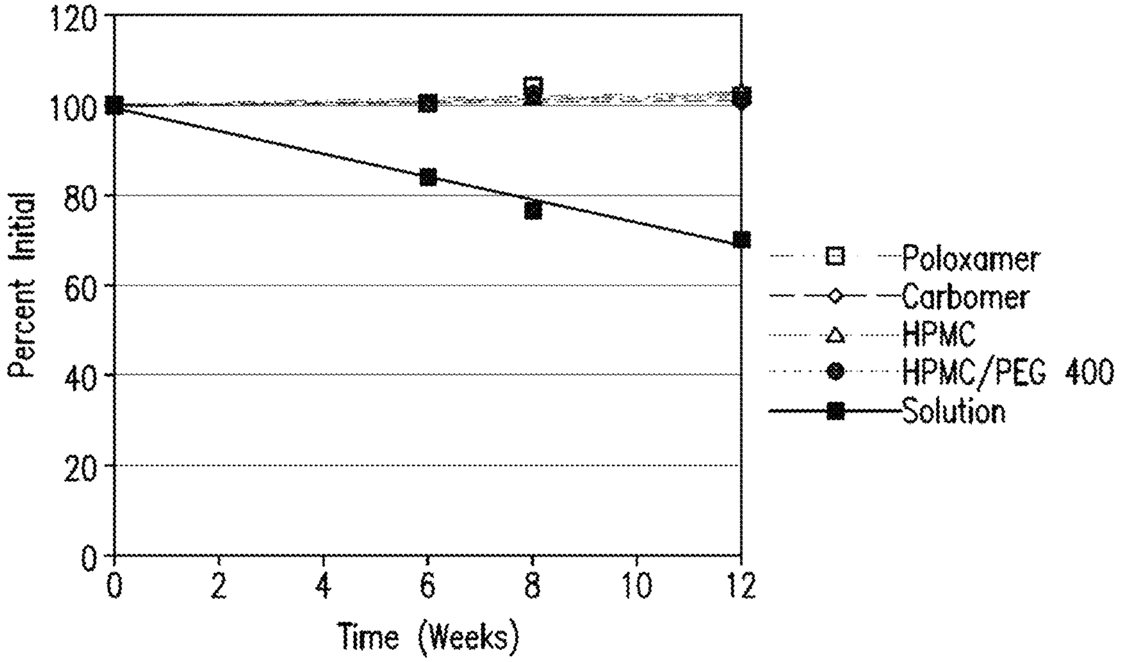
FIG. 14A shows the percent of compound I in the exploratory formulations described in Table 13 through 12 weeks at room temperature.
Figure 14B:
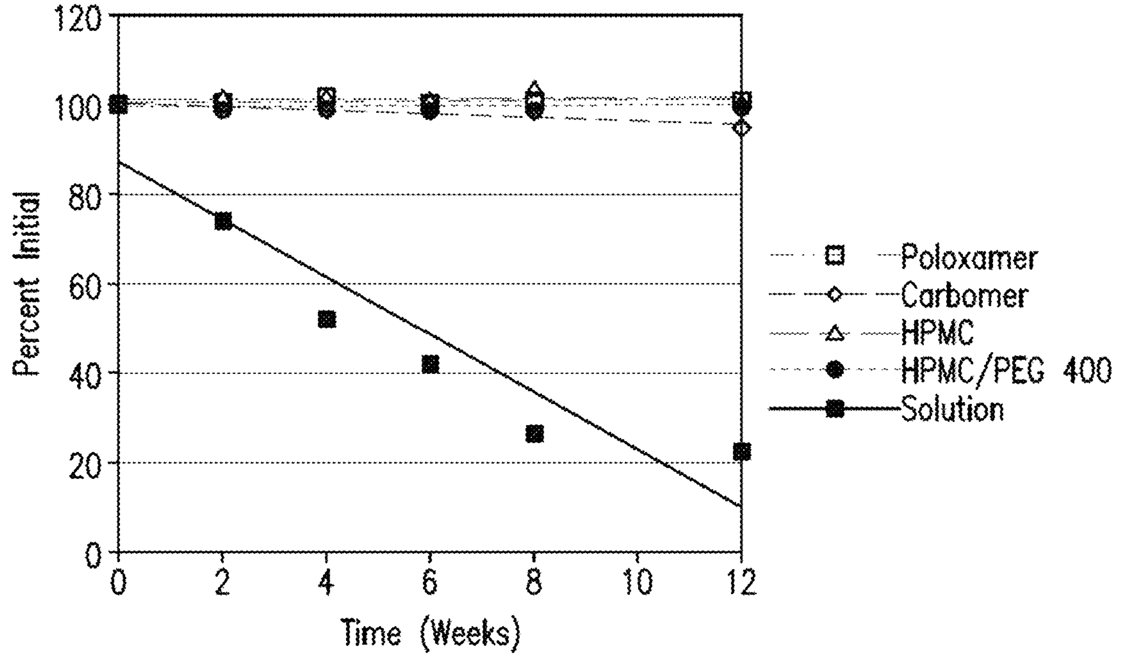
In FIG. 14B, the formulation with percent of compound I at about 20% of original at 12 weeks is the formulation of compound I as a solution.

Results from the testing for compound I stability at room temperature and 40° C. are shown in FIG. 14A and FIG. 14B, respectively. In FIG. 14A, the formulation with percent of compound I at about 70% of original at 12 weeks is the formulation of compound I as a solution. In FIG. 14B, the formulation with percent of compound I at about 20% of original at 12 weeks is the formulation of compound I as a solution. As seen in FIGS. 1A and 1B compound I remains in stable form in the suspensions, without significant degradation even at 12 weeks at 40° C. In contrast, the part of compound I in solution in the supernatant degrades to about 20% of initial amount after 12 weeks at 40° C.

Figure 15:
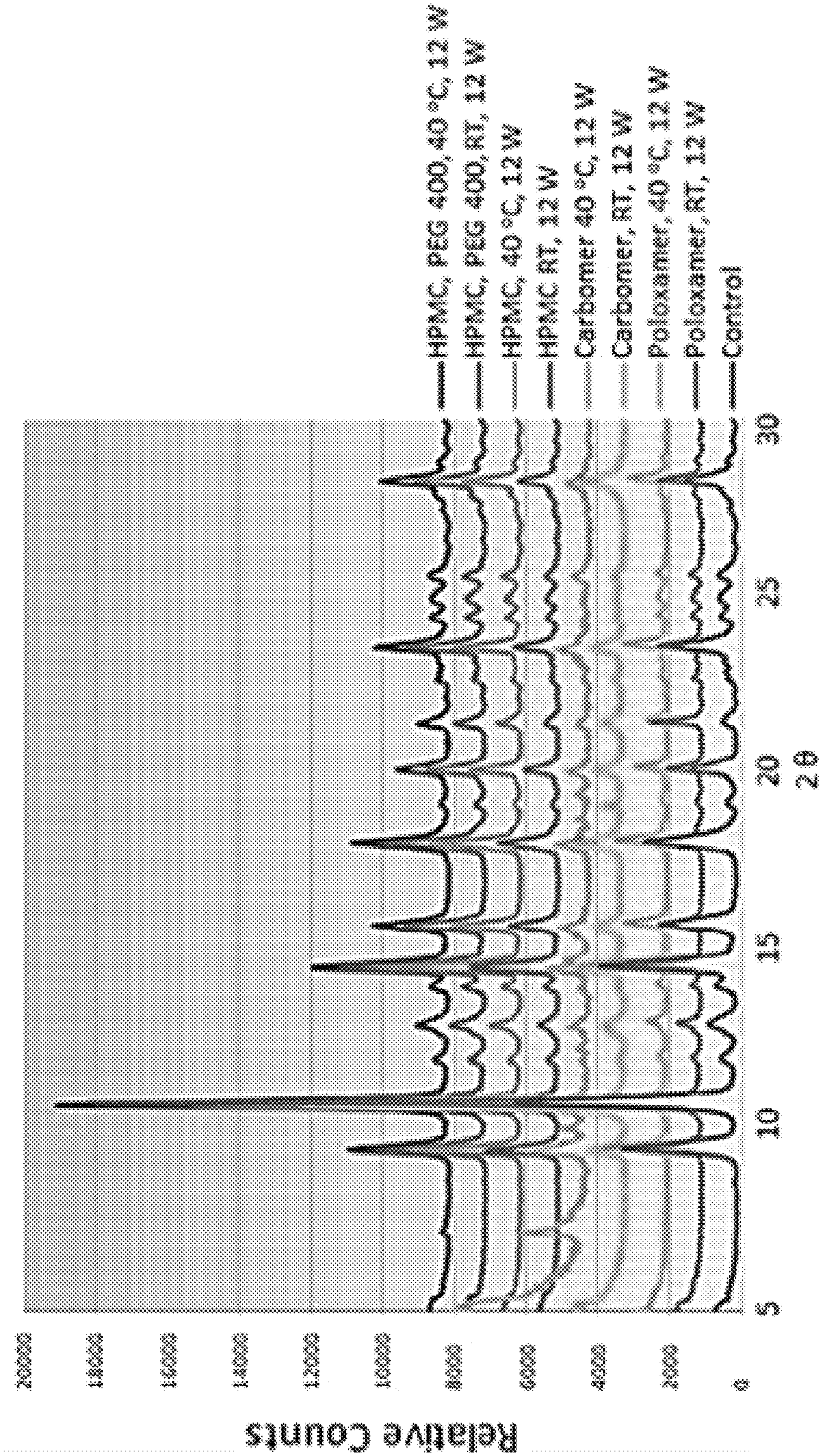
FIG. 15 shows the X-ray Powder Diffraction Patterns of compound I Recovered from 12-Week Stability Samples versus Control.

At the end of the study, compound I was recovered from the four suspensions and evaluated for changes in crystalline form by x-ray powder diffraction. The x-ray diffraction patterns of compound I recovered from the 12-week stability samples and that of compound I stored at room temperature (control) are presented in FIG. 15. As seen in FIG. 15, compound I in each of the four exploratory formulations maintains its polymorphic form even after storage at room temperature or 40° C. for 12 weeks.

The suspension FID 121744 (shown below in Table 17) and a 10% compound I slurry in 1% tyloxapol were subjected to heat sterilization 171° C. for 1 hour. The X-ray diffraction pattern of compound I after sterilization was identical to an untreated sample.

Example 1.1. Viscosity Range Finding Studies of Compound I Suspensions

Various suspension formulations of compound I were evaluated for viscosity and settling of compound I. A series of unpreserved compound I suspensions were prepared containing varying amounts of carbopol (Carbomer homopolymer Type B) and varying amounts of sodium chloride. The compositions of the formulations are shown in Table 15.

TABLE 15

| Compositions of compound I unpreserved suspensions of compound I for viscosity range finding studies | | | | | |
|---|---|---|---|---|---|
| FID: | 121845 | 121724 | 121846 | 121847 | 121848 |
| Component | Percent w/w | | | | |
| Compound I | 0.5 | 0.5 | 0.5 | 0.5 | 0.5 |
| Tyloxapol | 0.05 | 0.05 | 0.05 | 0.05 | 0.05 |
| Carbopol 974P [a] | 0.1 | 0.2 | 0.3 | 0.4 | 0.5 |
| Glycerin | 2.0 | 2.0 | 2.0 | 2.0 | 2.0 |
| Sodium Chloride | — | — | — | — | — |
| Tromethamine | qs pH 7.4 | qs pH 7.4 | qs pH 7.4 | qs pH 7.4 | qs pH 7.4 |
| Hydrochloric Acid | qs pH 7.4 | qs pH 7.4 | qs pH 7.4 | qs pH 7.4 | qs pH 7.4 |
| Purified Water | qs 100 | qs 100 | qs 100 | qs 100 | qs 100 |

[a] Carbomer homopolymer Type B

The suspensions were evaluated visually for uniformity. The suspension which contained only 0.1% Carbomer, FID 121845, was not uniform and therefore was not evaluated further. Sodium chloride is known to reduce the viscosity of Carbomer-containing suspensions, so sodium chloride was added to aliquots of the remaining four suspensions to obtain a total of 28 suspensions with concentrations of 0.2, 0.3, 0.4 and 0.5% Carbomer and 0, 0.05, 0.1, 0.15, 0.2, 0.25 and 0.3% sodium chloride.

Results from the viscosity testing of 28 suspensions are shown in Table 16.

TABLE 16

| Viscosities (cP) of compound I unpreserved suspensions from Table 15 (CP52, 60 RPM @ 25° C.) | | | | | | | |
|---|---|---|---|---|---|---|---|
| FID (% | Sodium chloride (% w/w) | | | | | | |
| carbomer) | 0 | 0.05 | 0.1 | 0.15 | 0.2 | 0.25 | 0.3 |
| 121724 (0.2) | Out of range | 64.5 | 23.9 | 14.6 | 10.4 | 7.59 | 7.44 |
| 121846 (0.3) | Out of range | Out of range | 101.2 | 59.8 | 38.0 | 25.6 | 18.9 |
| 121847 (0.4) | Out of range | Out of range | Out of range | Out of range | 121.1 | 84.0 | 63.7 |
| 121848 (0.5) | Out of range | Out of range | Out of range | Out of range | Out of range | Out of range | 150.8 |

As seen from Table 16, the relationship between the amounts of carbomer and sodium chloride affect the viscosity of the suspension.

A further set of unpreserved suspensions of compound I containing carbopol as a suspending agent were prepared for viscosity range finding and settling studies. The compositions, their viscosities and settling times of 10 ml of suspension after 6 months are shown in Table 17.

TABLE 17

Unpreserved suspensions of compound I and their viscosities and settling properties

| FID: Component | 121744 | 121896 | 121897 | 121898 | 121899 |
|---|---|---|---|---|---|
| | Percent w/w | | | | |
| Compound I | 0.5 | 0.5 | 0.5 | 0.5 | 0.5 |
| Tyloxapol | 0.05 | 0.05 | 0.05 | 0.05 | 0.05 |
| Carbopol 974P [a] | 0.2 | 0.2 | 0.2 | 0.2 | 0.2 |
| Glycerin | 2.0 | 2.0 | 2.0 | 2.0 | 2.0 |
| Sodium Chloride | 0.05 | 0.06 | 0.07 | 0.08 | 0.09 |
| Tromethamine | qs pH 7.4 | qs pH 7.4 | qs pH 7.4 | qs pH 7.4 | qs pH 7.4 |
| Hydrochloric Acid | qs pH 7.4 | qs pH 7.4 | qs pH 7.4 | qs pH 7.4 | qs pH 7.4 |
| Purified Water | qs 100 | qs 100 | qs 100 | qs 100 | qs 100 |
| Viscosity (cP) | 153.4 | 113.2 | 84.8 | 66.4 | 49.8 |
| Settling, ml (%) | <0.2 (<2%) | <0.2 (<2%) | <0.2 (<2%) | — | <0.2 (<2%) |

[a] Carbomer Homopolymer Type B

A further series of preserved suspensions containing hypromellose as the suspending agent were prepared and their viscosities measured. The settling properties were measured as follows: well mixed aliquots of the suspensions were filled into 10 ml glass graduated cylinders. The graduated cylinders were sealed with ground glass stoppers and Parafilm® and allowed to sit undisturbed for six months at room temperature. The settled suspension was estimated by visual inspection. The compositions, their viscosities and settling times of 10 ml of suspension after 6 months are shown in Table 18.

TABLE 18

Preserved suspensions of compound I and their viscosities and settling properties

| FID: Component | 121801 | 121901 | 121902 | 121903 |
|---|---|---|---|---|
| | Percent w/w | | | |
| Compound I | 0.5 | 0.5 | 0.5 | 0.5 |
| Tyloxapol | 0.05 | 0.05 | 0.05 | 0.05 |
| Hypromellose | 0.5 | 0.6 | 0.7 | 0.8 |
| Boric Acid | 0.3 | 0.3 | 0.3 | 0.3 |
| Mannitol | 0.3 | 0.3 | 0.3 | 0.3 |
| Propylene Glycol | 1.5 | 1.5 | 1.5 | 1.5 |
| Polyquaternium-1 | 0.001 | 0.001 | 0.001 | 0.001 |
| Sodium Hydroxide | qs pH 7.4 | qs pH 7.4 | qs pH 7.4 | qs pH 7.4 |
| Hydrochloric Acid | qs pH 7.4 | qs pH 7.4 | qs pH 7.4 | qs pH 7.4 |
| Purified Water | qs 100 | qs 100 | qs 100 | qs 100 |
| Viscosity (cP) | 20.0. | 32.0 | 50.2 | 76.4 |
| Settling, ml (%) | 0.6 (6%) | 0.4 (4%) | 0.2 (2%) | — |

Based on the results shown in Tables 9-12, compound I suspensions that are preserved or unpreserved and that have either carbomer or hypromellose as a suspending agent were able to achieve acceptable viscosities and settling properties.

Example 12. PH Dependent Stability Screening of Compound I Suspensions

In order to test the pH stability of compound I suspensions, the formulations listed in Table 19 below were prepared. All samples contain 0.1% compound I in order to keep drug concentration consistent. As this amount of drug was not soluble in any of the samples, 0.1% tyloxapol was used as a surfactant to aid in re-suspending the material in the samples. All samples (except the TRIS sample) contain an equivalent amount of phosphate buffer. All samples were placed in 20 mL glass vials and put on condition at 60° C. At each assay time point, samples were allowed to equilibrate to room temperature, vortexed to resuspend the drug, and samples were diluted to concentrations that fell within the linear range of the standard curve.

TABLE 19

Compound I stability sample compositions

| Component | pH 5 | pH 6 | pH 7 | pH 8 | Carbopol | HPMC | TRIS |
|---|---|---|---|---|---|---|---|
| | Percent w/w | | | | | | |
| Compound I | 0.1 | 0.1 | 0.1 | 0.1 | 0.1 | 0.1 | 0.1 |
| Tyloxapol | 0.1 | 0.1 | 0.1 | 0.1 | 0.1 | 0.1 | 0.1 |
| Hypromellose | — | — | — | — | — | 0.5 | — |
| Carbopol | — | — | — | — | 0.4 | — | — |
| Monobasic sodium phosphate | 0.13 | 0.13 | 0.13 | 0.13 | 0.13 | 0.13 | — |
| Dibasic sodium phosphate | 0.01 | 0.01 | 0.01 | 0.01 | 0.01 | 0.01 | — |
| Tromethamine | — | — | — | — | — | — | 0.03 |
| Sodium hydroxide | pH 5.0 | pH 6.0 | pH 7.0 | pH 8.0 | pH 7.4 | pH 7.4 | pH 7.4 |
| Hydrochloric acid | pH 5.0 | pH 6.0 | pH 7.0 | pH 8.0 | pH 7.4 | pH 7.4 | pH 7.4 |
| Purified water | Qs 100 | Qs 100 | Qs 100 | Qs 100 | Qs 100 | Qs 100 | Qs 100 |

The amount of compound I in the stability samples was tested at 0, 4, 7, and 11 days by high performance liquid chromatography (HPMC), using a Waters® XBridge®Shield RP18 Column (3.5 3.0×150 mm, 30° C.), using a gradient of mobile phase A 0.1% TFA in water and mobile phase B 0.1% TFA in acetonitrile, with an injection volume of 10 µl and a flow rate of 0.8 ml/min. In addition, the major degradant appearing at a relative retention time (RRT) of 1.23 was tracked. Results from the stability testing are shown in Table 20.

TABLE 20

| Stability of compound I and degradant growth at 60° C. | | | | | | | | |
|---|---|---|---|---|---|---|---|---|
| | Compound I stability (% initial) | | | | % Degradant @ RRT 1.23 | | | |
| Condition | Initial | Day 4 | Day 7 | Day 11 | Initial | Day 4 | Day 7 | Day 11 |
| pH 5 | 100 | 95.5 | 91.2 | 85.6 | 0 | 2.3 | 2.8 | 3.9 |
| pH 6 | 100 | 97.5 | 95.3 | 93.0 | 0 | 1.2 | 2.1 | 2.2 |
| pH 7 | 100 | 95.7 | 92.3 | 87.8 | 0 | 2.0 | 2.2 | 4.0 |
| pH 8 | 100 | 79.9 | 63.4 | 40.9 | 0 | 5.7 | 13.5 | 29.1 |
| Carbopol (pH 7.4) | 100 | 93.2 | 86.2 | 75.4 | 0 | 3.3 | 6.5 | 11.0 |
| HPMC (pH 7.4) | 100 | 94.4 | 89.8 | 83.3 | 0 | 2.9 | 5.1 | 8.2 |
| TRIS (pH 7.4) | 100 | 98.6 | 96.2 | 94.4 | 0 | 1.1 | 2.0 | 2.6 |

The major degradant shown in Table 20 was observed to crystallize out to form large crystals as its concentration increases. The following formulations shown in Table 21 were therefore prepared and analyzed for degradant formation.

TABLE 21

| Compound I stability sample compositions | | | | | | | |
|---|---|---|---|---|---|---|---|
| | 2% PVP | 5% HPβCD | 5% SBE-CD | 0.1% $CaCl_2$ | $CaCl_2$/ HPMC | 0.5% HPMC | 1% TRIS |
| Component | Percent w/v | | | | | | |
| Compound I | 0.1 | 0.1 | 0.1 | 0.1 | 0.1 | 0.1 | 0.1 |
| Tyloxapol | 0.1 | 0.1 | 0.1 | 0.1 | 0.1 | 0.1 | 0.1 |
| Povidone K30 | 2 | — | — | — | — | — | — |
| Hypromellose | — | — | — | — | 0.5 | 0.5 | — |
| HP-β-cyclodextrin | — | 5 | — | — | — | — | — |
| Sulfobutyl-cyclodextrin | — | — | 5 | — | — | — | — |
| Calcium chloride | — | — | — | 0.1 | 0.1 | — | — |
| Sodium citrate | 0.05 | 0.05 | 0.05 | 0.05 | 0.05 | 0.05 | 0.05 |
| Tromethamine | pH 6.0 | pH 6.0 | pH 6.0 | pH 6.0 | pH 6.0 | pH 6.0 | 1.0 |
| HCl | pH 6.0 | pH 6.0 | pH 6.0 | pH 6.0 | pH 6.0 | pH 6.0 | pH 6.0 |
| Purified water | Qs 100 | Qs 100 | Qs 100 | Qs 100 | Qs 100 | Qs 100 | Qs 100 |

Data on the stability of compound I in compositions shown in Table 21 is shown below in Table 22.

TABLE 22

| Stability of Compound I in Suspension at 40° C. and 60° C. | | | | | | | |
|---|---|---|---|---|---|---|---|
| | % Initial of compound I at 40° C. | | | | % Initial of compound I at 60° C. | | |
| 0.1% Compound I | Initial | Day 15 | Day 35 | Day 56 | Initial | Day 7 | Day 15 |
| 2% PVP | 100 | 98.5 | 97.0 | 95.4 | 100 | 94.5 | 87.6 |
| 5% HP-β-CD | 100 | 97.3 | 95.2 | 92.9 | 100 | 91.4 | 82.0 |
| 5% SBE—CD | 100 | 92.4 | 87.1 | 84.0 | 100 | 83.3 | 66.9 |
| 0.1% $CaCl_2$ | 100 | 98.4 | 97.6 | 96.3 | 100 | 94.7 | 87.3 |
| $CaCl_2$/HPMC | 100 | 97.7 | 97.0 | 94.7 | 100 | 93.4 | 87.4 |
| 0.5% HPMC | 100 | 97.7 | 96.4 | 95.7 | 100 | 93.1 | 89.9 |
| 1% TRIS | 100 | 97.4 | 95.9 | 93.7 | 100 | 89.8 | 79.5 |

Data on the degradant growth is shown in Table 23.

TABLE 23

| Compound I degradant growth in suspension at 40° C. and 60° C. | | | | | | | |
|---|---|---|---|---|---|---|---|
| 0.1% | % Deg @ RRT 1.23 at 40° C. | | | | % Deg @ RRT 1.23 at 60° C. | | |
| Compound I | Initial | Day 15 | Day 35 | Day 56 | Initial | Day 7 | Day 15 |
| 2% PVP | 0 | 0.6 | 1.4 | 1.7 | 0 | 2.5 | 2.4 |
| 5% HP-β-CD | 0 | 0.9 | 2.0 | 2.9 | 0 | 3.6 | 7.7 |
| 5% SBE—CD | 0 | 2.5 | 5.5 | 7.1 | 0 | 7.4 | 12.5 |
| 0.1% $CaCl_2$ | 0 | 0.4 | 0.9 | 1.5 | 0 | 2.2 | 2.4 |
| $CaCl_2$/HPMC | 0 | 0.6 | 1.4 | 1.9 | 0 | 2.5 | 5.5 |
| 0.5% HPMC | 0 | 0.5 | 1.1 | 1.5 | 0 | 2.0 | 4.1 |
| 1% TRIS | 0 | 0.7 | 1.6 | 1.7 | 0 | 3.0 | 7.8 |

Based on the stability data in the above Tables, it was concluded that the stability of compound I varies greatly over the pH range of 5-8. Further, increasing the solubility of compound I in SBE-cyclodextrin resulted in a decrease in the stability.

Example 13. Stability of 2.5%, 1.5%, 0.5% and 1.5% Ophthalmic Suspensions of Compound I The stability of a number of lots of compound I ophthalmic suspensions 0.15%, 0.5%, 1.5% and 2.5% (initial pH of 7.34-7.7) as described below in Table 29 were evaluated by monitoring the chemical, physical and microbiological stability characteristics of the product over time. The chemical stability was evaluated by monitoring compound I and its impurities. The physical stability was evaluated by monitoring the pH, osmolality, viscosity, appearance, identity by X-ray Powder Diffraction (XRPD), and particle size. The microbiological stability was evaluated by conducting sterility tests. A summary of the results (in ranges from different lots and various sampling times over the testing period) from the tests and stability monitoring limits for compound I ophthalmic suspensions are presented in Table 24.

TABLE 24

Stability testing data for ophthalmic suspensions of compound I

| Storage condition | Compound I suspension (w/v) | Condition monitored: % compound I of label | Total impurities (No more than 6.0%) | Impurity at RRT of 1.2 (No more than 4.5%) | pH Range: 6.8-8.0 | Osmolality Range: 200-350 mOsm/kg (initial 231-251) |
|---|---|---|---|---|---|---|
| 25 ± 2° C./ 40% ± 5% RH (up to 26 weeks) | 2.5% | 98-100 | 0.0-0.2 | <0.1-0.2 | 7.53-7.61 | 231-247 |
| | 1.5% | 99-100 | 0.1-0.2 | 0.1-0.2 | 7.52-7.63 | 243-244 |
| | 0.5% | 96-98 | 0.2-0.5 | 0.2-0.5 | 7.49-7.51 | 242-243 |
| | 0.15% | 95-99 | 0.3-1.6 | 0.3-1.6 | 7.54-7.60 | 236-244 |
| 40 ± 2° C./ <25% ± 5% RH (up to 26 weeks) | 2.5% | 98-103 | 0.2-0.6 | 0.2-0.6 | 7.52-7.58 | 235-240 |
| | 1.5% | 100-102 | 0.3-0.9 | 0.3-0.9 | 7.52-7.59 | 244-255 |
| | 0.5% | 97-97 | 0.7-2.4 | 0.7-2.4 | 7.48-7.52 | 246-251 |
| | 0.15% | 85-95 | 1.2-8.6 | 1.2-8.6 | 7.45-7.56 | 239-252 |
| 5 ± 2° C./ 35% ± 5% RH (up to 104 weeks) | 2.5% | 96-102 | 0.1-0.4 | <0.1-0.2 | 7.45-7.59 | 230-245 |
| | 1.5% | 98-102 | 0.2-0.2 | 0.0-2.2 | 7.46-7.60 | 241-244 |
| | 0.5% | 97-98 | 0.2-0.2 | 0.2-0.2 | 7.54 | 240 |
| | 0.15% | 96-102 | 0.1-0.4 | 0.2-0.4 | 7.54-7.62 | 238-242 |

In addition to the above parameters, viscosity was monitored and found to be within 10% of the initial viscosity at each tested time point under each storage condition. Particle size measurements and sterility were also within stability monitoring limits.

Example 14. Acute Toxicology Study of Exploratory Formulations

The four formulations from the exploratory stability studies in Table 13, FID 121522, FID 121511, FID 121512, FID 121513 were dosed male NZW rabbits 5 times in one day, using a sterile irrigating solution as a control. No toxicity was observed for the four exploratory formulations or the control.

Example 15. Pharmacokinetic Study of Exploratory Formulations

A pharmacokinetics study was conducted to determine the ocular uptake of compound I following single bilateral topical ocular dosing of male NZW rabbits with the same four exploratory formulations provided in Table 13: FID 121522, FID 121511, FID 121512, FID 121513. Results are shown in Table 25.

TABLE 25

Summary of compound I $C_{max}$ and $C_{min}$ Results from pharmacokinetic study

| FID: Matrix | | 121522 | 121511 | 121512 | 121513 |
|---|---|---|---|---|---|
| | | Concentration (nM) | | | |
| Cornea | $C_{max}$ | 34700 | 15760 | 16400 | 901 |
| | $C_{min}$ | 3900 | 4520 | 1470 | BLQ* |
| Conjunctiva | $C_{max}$ | 24500 | 4680 | 5270 | 165 |
| | $C_{min}$ | 1570 | 1420 | 2770 | BLQ |
| Aqueous Humor | $C_{max}$ | 3730 | 1780 | 1940 | 185 |
| | $C_{min}$ | 98.9 | 55.4 | 20.1 | BLQ |
| Iris-Ciliary Body | $C_{max}$ | 3640 | 1480 | 1800 | 153 |
| | $C_{min}$ | 223 | 169 | 65 | BLQ |
| Plasma | $C_{max}$ | 63 | 30.2 | 43.5 | 0.834 |
| | $C_{min}$ | 2.18 | 1.00 | 0.741 | BLQ |
| | $IC_{50}$ | 30 | 30 | 30 | 30 |

*BLQ = Below Limit of Quantitation Cmin determined at 4 hours after administration.

As seen in Table 25, the highest exposures of compound I was in the cornea, which was approximately 1.5 to 3 times the levels observed in the conjunctiva, and approximately 10 times the levels observed in the aqueous humor and iris-ciliary body and approximately 500 times the levels observed in plasma. In the cornea, $C_{max}$ for the suspension with Poloxamer 407 was approximately 2 times the $C_{max}$ for the two suspensions with hypromellose and approximately 38 times the $C_{max}$ for the solution formulation. For the three suspensions, $C_{max}$ in the cornea ranged from approximately 500 to 1200 times the $IC_{50}$ of 30 nM, while $C_{min}$ ranged from approximately 50 to 130 times the $IC_{50}$.

Example 16. Pharmacokinetic Study of Further Formulations

Based on the results from the exploratory formulations, further formulations were prepared for additional determine the corneal and aqueous humor concentrations of compound I following single bilateral topical ocular dosing in male pigmented rabbits. These formulations are shown in Table 26.

TABLE 26

Unpreserved Suspension Formulations of Compound I for PK Study

| FID: Component | 121746 | 121745 | 121744 |
|---|---|---|---|
| | Percent w/w | | |
| Compound I | 0.01 | 0.05 | 0.5 |
| Tyloxapol | 0.05 | 0.05 | 0.05 |
| Carbomer Homopolymer Type B | 0.2 | 0.2 | 0.2 |
| Glycerin | 2.0 | 2.0 | 2.0 |
| Sodium Chloride | 0.05 | 0.05 | 0.05 |
| Tromethamine | qs pH 7.4 | qs pH 7.4 | qs pH 7.4 |
| Hydrochloric Acid | qs pH 7.4 | qs pH 7.4 | qs pH 7.4 |
| Purified Water | qs 100 | qs 100 | qs 100 |

Results from the pharmacokinetic study are shown in Table 27.

TABLE 27

Summary of Cmax and Cmin Results from PK Study

| Matrix | FID: | 121746 | 121745 | 121744 |
|---|---|---|---|---|
| | | Concentration (nM) | | |
| Cornea | $C_{max}$ | 1150 | 5550 | 18500 |
| | $C_{min}$ | 14 | 20 | 223 |
| Aqueous Humor | $C_{max}$ | 314 | 950 | 2990 |
| | $C_{min}$ | BLQ* | BLQ | 11.1 |
| | $IC_{50}$ | 30 | 30 | 30 |

*Below limit of quantitation Cmin results obtained at 8 hours after dosing

As seen in Table 27, $C_{max}$ and $C_{min}$ for compound I show that the highest exposures of compound I were in the cornea, with levels approximately 3 to 6 times the levels observed in the aqueous humor. In the cornea, $C_{max}$ for the 0.5% suspension was approximately 3 times that of the 0.05% suspension and approximately 16 times that of the 0.01% suspension. In the aqueous humor, $C_{max}$ for the 0.5% suspension was approximately 3 times that of the 0.05% suspension and approximately 9 times that of the 0.01% suspension. For the three suspensions, $C_{max}$ the cornea ranged from approximately 38 to 600 times the $IC_{50}$ of 30 nM, while $C_{min}$ ranged from approximately 0.5 to 7 times the $IC_{50}$.

A pharmacokinetics study was conducted to determine the corneal and aqueous humor concentrations of compound I following single bilateral topical ocular dosing in intact eyes and following anterior keratectomy with and without bandage contact lenses in male pigmented rabbits using the formulations described in Table 26, FID121746, FID121745, and FID121744.

Results from the pharmacokinetic study are shown in Table 28.

TABLE 28

Summary of $C_{max}$ and $AUC_{0-8\ h}$ Results from PK Study of rabbits following anterior keratectomy

| | | FID: | | | | |
|---|---|---|---|---|---|---|
| | | 121746 | 121745 | | 121744 | |
| Corneas | | w/o CL [a] | w/o CL [a] | w/CL [b] | w/o CL [a] | w/CL [b] |
| | | Concentration (nM; AUC: nM · h) | | | | |
| Intact | $C_{max}$ | 1147 | 5550 | | 18500 | |
| | $AUC_{0-8\ h}$ | 1433 | 4550 | | 31700 | |
| Anterior | $C_{max}$ | | 1910 | 1490 | | 10700 |
| Keratectomy | $AUC_{0-8\ h}$ | | 1770 | 4400 | | 26700 |
| | $IC_{50}$ [c] | 27 | 27 | 27 | 27 | 27 |

[a] Without bandage contact lenses
[b] With bandage contact lenses
[c] IC50 for N-arachidonoyl dopamine (NADA)

Example 17. Toxicology Wound Healing Study with Compound I Suspension Formulations A toxicology wound healing study was conducted to evaluate corneal wound healing following QID bilateral topical ocular dosing of compound I after unilateral laser photorefractive keratectomy in rabbits with and without bandage contact lenses. The compound I formulations used in the study are described in Table 29. For comparator purposes, ketorolac tromethamine (ACULAR LS®) and dexamethasone (MAXIDEX®) formulations were used.

TABLE 29

Compositions of Compound I Vehicle and Suspensions for Wound Healing Study

| FID: Component | 121830 | 121744 | 121816 | 121814 |
|---|---|---|---|---|
| | Percent w/w | | | |
| Compound I | | 0.5 | 1.5 | 2.5 |
| Tyloxapol | 0.05 | 0.05 | 0.05 | 0.05 |
| Carbomer Homopolymer Type B | 0.2 | 0.2 | 0.2 | 0.2 |
| Glycerin | 2.0 | 2.0 | 2.0 | 2.0 |
| Sodium Chloride | 0.05 | 0.05 | 0.05 | 0.05 |
| Tromethamine | qs pH 7.4 | qs pH 7.4 | qs pH 7.4 | qs pH 7.4 |
| Hydrochloric Acid | qs pH 7.4 | qs pH 7.4 | qs pH 7.4 | qs pH 7.4 |
| Purified Water | qs 100 | qs 100 | qs 100 | qs 100 |

The study results demonstrated that after 3 days, the mean wound areas for the corneas treated with 0.5, 1.5 and 2.5% compound I suspensions with bandage contact lenses were smaller than those for the corneas treated with ACULAR LS® and MAXIDEX® with bandage contact lenses, vehicle without bandage contact lenses and for untreated corneas. The mean wound areas for the corneas treated with 0.5, 1.5 and 2.5% compound I suspensions with bandage contact lenses were comparable to those for the corneas treated with vehicle with bandage contact lenses and 2.5% compound I without bandage contact lenses.

Example 18. Bacteriostasis/Stability Studies of Exemplary Compound I Suspensions A series of five prototype sterile suspension formulations containing 0.5% compound I were prepared and screened for bacteriostasis/fungistasis with five compendial organisms: *S. aureus, P. aeruginosa, E. coli, C. albicans* and *A. brasiliensis*. The criterion for stasis was no more than 0.5 log increase in microbial counts (CFU/mL). All the tested formulations demonstrated an acceptable level of bacteriostasis/fungistasis. In addition, a 2.5% compound I suspension (otherwise identical to FID 121744), and suspension vehicle were also prepared and screened for bacteriostasis/fungistasis screening. Bacteriostasis/fungistasis was observed through 3 days with an inoculum of ~$10^6$ and/or an inoculum of ~$10^5$.

All publications and patent documents cited herein are incorporated herein by reference as if each such publication or document was specifically and individually indicated to be incorporated herein by reference. The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the invention that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein. The claims should not be read as limited to the described order or elements unless stated to that effect. It should be understood that various changes in form and detail may be made without departing from the scope of the appended claims.

What is claimed is:

1. A crystal form A of 4-(7-Hydroxy-2-isopropyl-4-oxo-4H-quinazolin-3-yl)benzonitrile (compound I) having structure

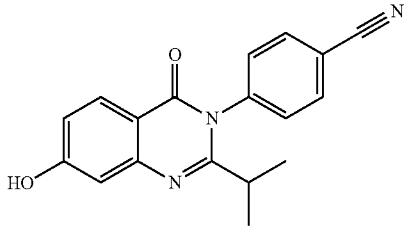

characterized by an X ray diffraction pattern comprising peaks at 2θ values of 7.2, 12.7, and 21.4±0.2 °2θ.

2. The crystal form A of compound I according to claim 1, characterized by an X ray diffraction pattern comprising three or more peaks at 2θ values selected from 7.2, 12.7, 13.9, 18.1, 21.4, 25.1, and 26.8±0.2 °2θ.

3. A method of preparing a crystal form A of compound I according to claim 1, comprising cooling a hot solution of the free base of compound I in methanol and cooling to about 0° C., to crystallize compound I as crystal form A.

4. A crystal form C of 4-(7-Hydroxy-2-isopropyl-4-oxo-4H-quinazolin-3-yl)benzonitrile (compound I) having structure

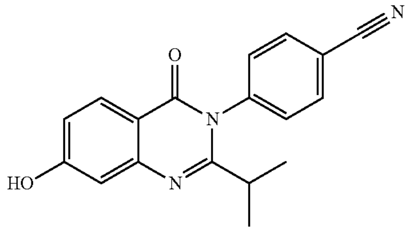 [SMILES: CC(C)c1nc2cc(O)ccc2c(=O)n1-c1ccc(C#N)cc1]

characterized by an X ray diffraction pattern comprising peaks at 2θ values of 7.4, 14.9, and 19.1±0.2 °2θ.

5. The crystal form C of compound I according to claim 4, characterized by an X ray diffraction pattern comprising three or more peaks at 2θ values selected from 7.4, 14.1, 14.9, 16.4, 19.1, 26.1, and 31.2±0.2 °2θ.

6. A method of preparing a crystal form C of compound I according to claim 4, comprising heating compound I in crystal form A to a temperature of at least about 250° C., or at least about 270° C., or about 280° C.

7. A crystal form E of 4-(7-Hydroxy-2-isopropyl-4-oxo-4H-quinazolin-3-yl)benzonitrile (compound I) having structure

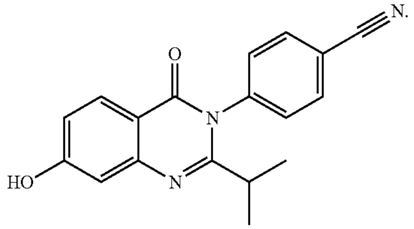 [SMILES: CC(C)c1nc2cc(O)ccc2c(=O)n1-c1ccc(C#N)cc1]

characterized by an X ray diffraction pattern comprising peaks at 2θ values of 12.7, 16.7, and 22.6±0.2 °2θ.

8. The crystal form E of compound I according to claim 7, characterized by an X ray diffraction pattern comprising three or more peaks at 2θ values selected from 12.7, 15.1, 16.7, 22.6, 27.1, 27.7, and 28.5±0.2 °2θ.

9. A method of preparing a crystal form E of compound I according to claim 7, comprising heating a hydrate form of compound I to temperatures greater than about 250° C. or about 260° C. to provide compound I as crystal form E.

10. A crystalline hydrate of 4-(7-Hydroxy-2-isopropyl-4-oxo-4H-quinazolin-3-yl)-benzonitrile (compound I) having structure

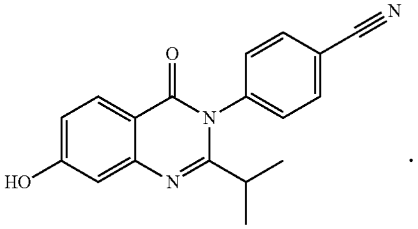 [SMILES: CC(C)c1nc2cc(O)ccc2c(=O)n1-c1ccc(C#N)cc1 ; "."]

11. The crystalline hydrate of compound I according to claim 10, characterized by an X ray diffraction pattern comprising peaks at 2θ values of 6.6, 14.4, and 18.3±0.2 °2θ.

12. The crystalline hydrate of compound I according to claim 10, characterized by an X ray diffraction pattern comprising three or more peaks at 2θ values selected from 6.6, 11.9, 14.4, 18.3, 23.9, 26.5, and 29.2±0.2 °2θ.

13. A method of preparing the crystalline hydrate of compound I according to claim 10, comprising equilibrating a slurry of compound I in a mixture of water and a water miscible solvent, to crystallize compound I as the crystalline hydrate.

14. The method according to claim 13, wherein the water miscible solvent is acetone.

15. The method according to claim 13, wherein the equilibration is carried out for about 12 hours, about 18 hours, or about 24 hours, or about 48 hours.

16. A pharmaceutical formulation, comprising an effective amount of a crystal form of compound I selected from the group consisting of: crystal form A, crystal form C, crystal form D, crystal form E, and combinations thereof, and a pharmaceutically acceptable excipient.

* * * * *